United States Patent
Riebel et al.

(10) Patent No.: US 6,638,979 B1
(45) Date of Patent: Oct. 28, 2003

(54) IMIDAMIDE DERIVATIVES

(75) Inventors: Hans-Jochem Riebel, Selters (DE); Peter Gerdes, Aachen (DE); Ernst-Rudolf F. Gesing, Erkrath-Hochdahl (DE); Achim Hense, Leichlingen (DE); Johannes Kanellakopulos, Dormagen (DE); Kristian Kather, Köln (DE); Rolf Kirsten, Monheim (DE); Stefan Lehr, Langenfeld (DE); Lothar Rohe, Wuppertal (DE); Katharina Voigt, Monheim (DE); Detleff Wollweber, Wuppertal (DE); Wolfram Andersch, Bergisch Gladbach (DE)

(73) Assignee: Bayer Aktiengesellschaft, Leverkusen (DE)

(*) Notice: Subject to any disclaimer, the term of this patent is extended or adjusted under 35 U.S.C. 154(b) by 0 days.

(21) Appl. No.: 09/743,588

(22) PCT Filed: Jul. 7, 1999

(86) PCT No.: PCT/EP99/04747

§ 371 (c)(1),
(2), (4) Date: Feb. 5, 2001

(87) PCT Pub. No.: WO00/03976

PCT Pub. Date: Jan. 27, 2000

(30) Foreign Application Priority Data

Jul. 18, 1998 (DE) .......................... 198 32 447
May 27, 1999 (DE) .......................... 199 24 273

(51) Int. Cl.⁷ .................. A01N 37/53; A01N 43/34; C07C 257/10; C07C 257/22; C07C 261/04
(52) U.S. Cl. .................. 514/609; 514/610; 564/103; 564/105; 564/106; 564/108
(58) Field of Search .................. 564/103, 105, 564/106, 108; 514/609, 610

(56) References Cited

FOREIGN PATENT DOCUMENTS

| | | |
|---|---|---|
| DE | 19 548 783 | 7/1997 |
| EP | 314 852 | 5/1989 |
| EP | 0 403 159 | 3/2000 |
| WO | 91/04965 | 4/1991 |
| WO | 93/04032 | 3/1993 |

OTHER PUBLICATIONS

Kishimoto et al., Chemical Abstracts, vol. 119:72239, 1993.*
Kreutzberger, Chemical Abstracts, vol. 84:121773, 1976.*
Kreutzberger et al., Chemical Abstracts, vol. 80:141179, 1974.*
J. Organomet. Chem., 97 (month unavailable) 1975, pp. 39–44, Kupchik et al, Reactions of Thioamides with Bis-(Triphenylstannyl)–Carbodiimide and (Triphenylstannyl)Cyanamide.
Bull. Soc. Chim. Belg., vol. 90(1), (month unavailable) 1981, pp. 89–98, L'abbé et al, Synthesis of Symmetrical 1,6–Dihetero–6aλ.aa⁴–Thia–3,4–Diazapentalenes from 5–Amino–1,2,3,4–Thiatriazole.
**Patent Abstracts of Janpan, vol. 199, No. 711, Nov. 28, 1997 JP 09 194451 A (Nippon Soda Co Ltd), Jul. 29, 1997.

* cited by examiner

Primary Examiner—Richard L. Raymond
(74) Attorney, Agent, or Firm—Richard E. L. Henderson; Joseph C. Gil

(57) ABSTRACT

The present invention relates to novel imidamide derivatives of the formula (I)

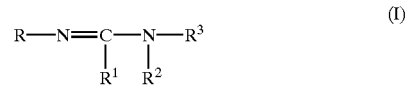

in which

R, $R^1$, $R^2$ and $R^3$ are each as defined in the description, to a process for their preparation and to their use for controlling animal pests, such as insects, arachnids and, in particular, nematodes.

7 Claims, No Drawings

IMIDAMIDE DERIVATIVES

This application is a 371 of PCT/EP99/04747, filed Jul. 7, 1999.

The present invention relates to novel imidamide derivatives, to a process for their preparation and to their use for controlling animal pests.

Certain imidamide derivatives are already known (cf. WO 91 04 965, WO 93 04 032, EP 0 403 159; J. Organomet. Chem. (1975), 97 (1), pp. 39–44; Bull. Soc. Chim. Belg. (1981), 90 (1), pp. 89–98). The insecticidal properties of some of these compounds have also been known.

This invention provides novel imidamide derivatives of the general formula (I)

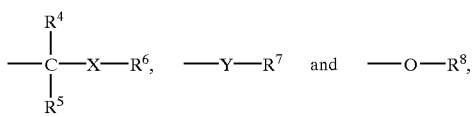

in which
R represents cyano or nitro,
$R^1$ represents hydrogen, optionally substituted alkyl, optionally substituted cycloalkyl or optionally substituted phenyl,
$R^2$ represents hydrogen, optionally substituted alkyl or optionally substituted cycloalkyl and
$R^3$ represents the groupings

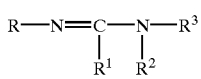

where
$R^4$ and $R^5$ independently of one another each represent hydrogen, optionally substituted alkyl or optionally substituted cycloalkyl,
$R^6$ and $R^7$ independently of one another represent optionally substituted aryl, optionally substituted cycloalkyl or represent an optionally substituted mono- or bicyclic, nitrogen-free heterocycle.
$R^8$ represents alkyl or optionally substituted aryl,
X represents a single bond, represents in each case straight-chain or branched alkanediyl, alkenediyl, alkinediyl and also represents the groupings —A—O—, —A—S—, —A—O—A'-, —A—S—A'—, —A—N(Alk)- or —A—N(Alk)-A'—, where the moiety A is attached to the C atom of the grouping —C($R^4R^5$)—X—$R^6$;
Alk represents alkyl and
A and A' independently of one another each represent straight-chain or branched alkanediyl and
Y represents a single bond and also the groupings —O—A—, —O—A"—O—, —O—A"—S—, —O—A"—SO—, —O—A"—$SO_2$—, —O—A"—O—A'— or —O—A"—S—A'—, where the O atom of these groupings is always attached to the N atom of the skeleton of the formula (I):
A and A' are each as defined above and
A" represents straight-chain or branched alkanediyl having it least 2 carbon atoms between the heteroatoms.
with the proviso that for R=CN and $R^2$=H the compounds in which

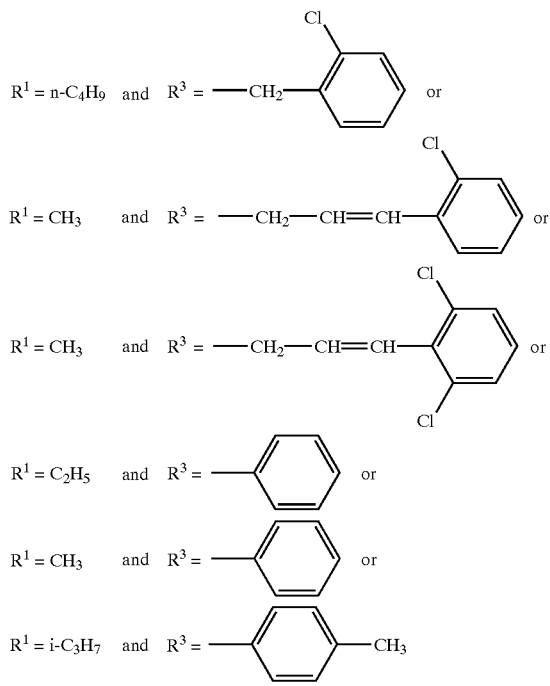

are excluded.

Depending, inter alia, on the substituents, the imidamide derivatives of the formula (I) may be present as optical and/or geometrical isomers. The present invention relates both to the various isomer mixtures and to the pure isomers.

The novel imidamide derivatives of the general formula (I) are obtained when ethaneimido esters of the formula (II)

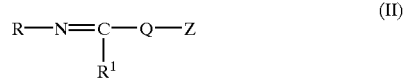

in which
R and $R^1$ are each as defined above,
Q represents oxygen or sulphur and
Z represents alkyl
are reacted with amines of the formula (III)

in which
$R^2$ and $R^3$ are each as defined above
in the presence of a diluent.

The novel imidamide derivatives of the general formula (I) have pronounced biological properties and are suitable in particular for controlling animal pests, such as insects, arachnids and, in particular, nematodes encountered in agriculture, in forests, in the protection of stored products and materials and in the hygiene sector.

The formula (I) provides a general definition of the compounds according to the invention. Preferred substituents or ranges of the radicals listed in the formulae mentioned above and below are illustrated below.

R preferably represents cyano or nitro.
$R^1$ preferably represents hydrogen, represents optionally halogen-, cyano- or $C_1$–$C_4$-alkoxy-substituted $C_1$–$C_4$- alkyl, represents $C_3$–$C_6$-cycloalkyl which is optionally mono- to trisubstituted by identical or different substituents selected from the group consisting of halogen $C_1$–$C_4$-alkyl or represents phenol which is optionally mono- to trisubstitued by identical or different substituents, possible substituents being the phenyl substituents mentioned under $R^6$.

$R^2$ preferably represents hydrogen, represents optionally halogen-, cyano- or $C_1$–$C_4$-alkoxy-substituted $C_1$–$C_4$-alkyl or represents $C_3$–$C_6$-cycloalkyl which is optionally mono- to trisubstituted by identical or different substituents selected from the group consisting of halogen or $C_1$–$C_4$-alkyl;

$R^3$ preferably represents the groupings

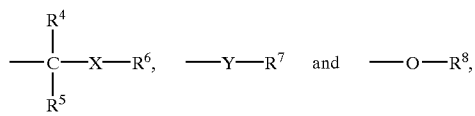

where $R^4$ and $R^5$ independently of one another each preferably represent hydrogen, represent optionally halogen-, cyano- or $C_1$–$C_4$-alkoxy-substituted $C_1$–$C_4$-alkyl or represent $C_3$–$C_6$-cycloalkyl which is optionally mono- to trisubstituted by identical or different substituents selected from the group consisting of halogen or $C_1$–$C_4$-alkyl.

$R^6$ and $R^7$ independently of one another each preferably represent phenyl, naphthyl, dihydronaphthyl and tetrahydronaphthyl, each of which is optionally mono- to pentasubstituted by identical or different substituents, possible substituents being those below:

hydroxyl, amino, cyano, nitro, halogen; in each case optionally hydroxyl-, cyano- or halogen-substituted $C_1$–$C_4$-alkyl, $C_1$–$C_4$-alkoxy, $C_1$–$C_4$-alkylamino and di-($C_1$–$C_4$-alkyl)amino; in each case optionally halogen-substituted $C_1$–$C_4$-alkylcarbonyl, $C_1$–$C_4$-alkoxy-carbonyl, $C_1$–$C_4$-alkyl-carbonyl-amino, $C_1$–$C_4$-alkylthio, $C_1$–$C_4$-alkylsulphinyl and $C_1$–$C_4$-alkylsulphonyl, aminocarbonyl, aminothiocarbonyl, $C_1$–$C_4$-alkylaminocarbonyl, di-($C_1$–$C_4$-alkyl)aminocarbonyl, amino-sulphonyl, $C_1$–$C_4$-alkylaminosulphonyl and di-($C_1$–$C_4$-alkyl)aminosulphonyl; and also phenyl, phenoxy, phenylthio, phenylsulphinyl, phenylsulphonyl, benzyl and phenylamino, each of which is optionally substituted by hydroxyl, cyano, nitro, halogen, $C_1$–$C_4$-alkyl, $C_1$–$C_4$-alkoxy, $C_1$–$C_4$-alkylthio, $C_1$–$C_4$-alkylsulphinyl, $C_1$–$C_4$-alkylsulphonyl and $C_1$–$C_4$-halogenoalkyl, $C_1$–$C_4$-halogenoalkoxy, $C_1$–$C_4$-halogenalkylthio, $C_1$–$C_4$-halogenalkylsulphinyl and $C_1$–$C_4$-halogenoalkylsulphonyl having in each case 1 to 5 identical or different halogen atoms from the series consisting of chlorine, fluorine and bromine;

furthermore represent $C_3$–$C_{12}$-cycloalkyl or $C_5$–$C_{12}$-cycloalkenyl, each of which is optionally mono- to pentasubstituted by identical or different substituents, possible substituents being:

Halogen, optionally substituted $C_1$–$C_4$-alkyl, preferred substituents being: halogen, such as fluorine, chlorine, bromine, optionally substituted $C_2$–$C_6$-cycloalkyl and optionally substituted phenyl;

furthermore $C_1$–$C_4$-alkyl, $C_1$–$C_4$-alkoxy and also $C_1$–$C_4$-halogenoalkyl and $C_1$–$C_4$-halogenoalkoxy having in each case 1to 5 identical or different halogen atoms selected from the series consisting of fluorine, chlorine and bromine;

and also represent a saturated or partially unsaturated or unsaturated mono-, bi- or tricyclic nitrogen-free heterocycle having 4 to 10 C atoms and 1to 3 identical or different heteroatoms, such as O and S atoms, which is optionally mono- to pentasubstituted by identical or different substituents, possible substituents being the phenyl substituents mentioned under $R^6$.

$R^8$ preferably represents $C_1$–$C_4$-alkyl or represents phenyl and naphthyl, each of which is optionally mono- to pentasubstituted by identical or different substituents, possible substituents being the phenyl substituents mentioned under $R^6$.

X preferably represents a single bond, represents in each case straight-chain or branched $C_1$–$C_6$-alkanediyl, $C_2$–$C_6$-alkenediyl or $C_2$–$C_6$-alkinediyl and also represents the groupings —A—O—, —A—S—, —A—O—A'—, —A—S—A'—, —A—N(Alk)- or —A—N(Alk)-A'—, where Alk preferably represents $C_1$–$C_4$-alkyl and A and A' independently of one another each preferably represent straight-chain or branched $C_1$–$C_6$-alkanediyl.

Y preferably represents a single bond and also the groupings —O—A—, —O—A"—O—, —O—A"—S—, —O—A"—SO—, —O—A"—$SO_2$—, —O—A"—O—A'— or —O—A"—S—A'—, where A and A' are each preferably as defined above.

A" preferably represents straight-chain or branched $C_2$–$C_4$-alkanediyl having at least 2 carbon atoms between the heteroatoms.

The preferred definitions are given with the proviso that for R=CN and $R^2$=H the compounds in which

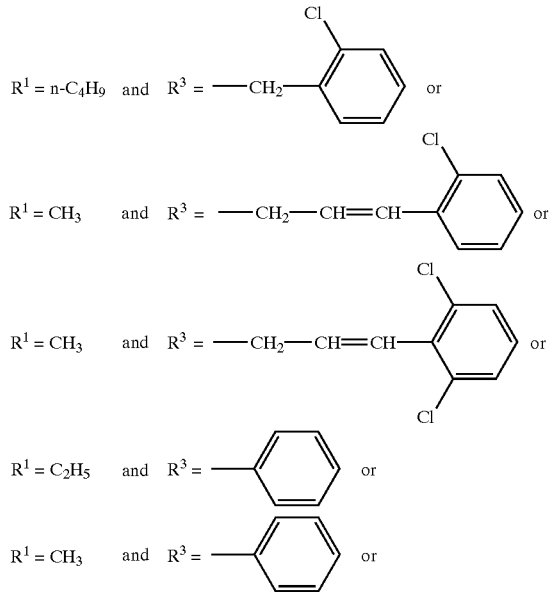

$R^1 = i\text{-}C_3H_7$ and $R^3 =$ 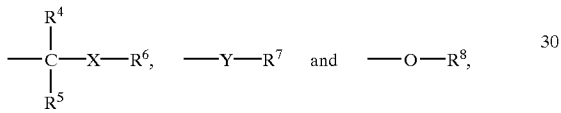—$CH_3$ are excluded.

R particularly preferably represents cyano or nitro.

$R^1$ particularly preferably represents hydrogen, represents in each case optionally cyano-, fluorine-, chlorine-, methoxy- or, ethoxy-substituted methyl, ethyl, n- or i-propyl and n- i-, s- or t-butyl; represents cyclopropyl, cyclopentyl and cyclohexyl, each of which is optionally mono- to trisubstituted by identical or different substituents selected from the group consisting of fluorine, chlorine, bromine, methyl and ethyl or represents phenyl which is optionally mono- to trisubstituted by identical or different substituents, possible substituents being the phenyl substituents mentioned under $R^6$.

$R^2$ particularly preferably represents hydrogen, represents in each case optionally cyano-, fluorine-, chlorine-, methoxy- or ethoxy-substituted methyl, ethyl, n- or i-propyl and n-, i-, s- or t-butyl, or represents cyclopropyl, cyclopentyl and cyclohexyl, each of which is optionally mono- to trisubstituted by identical or different substituents selected from the group consisting of fluorine, chlorine, bromine, methyl and ethyl.

$R^3$ particularly preferably represents the groupings $$-\underset{R^5}{\overset{R^4}{C}}-X-R^6, \quad -Y-R^7 \quad \text{and} \quad -O-R^8,$$

where $R^4$ and $R^5$ independently of one another each particularly preferably represent hydrogen, represent in each case optionally cyano-, fluorine-, chlorine-, methoxy- or ethoxy-substituted methyl, ethyl, n- or i-propyl and n-, i-, s- or t-butyl, or represent cyclopropyl, cyclopentyl and cyclohexyl, each of which is optionally mono- to trisubstituted by identical or different substituents selected from the group consisting of fluorine, chlorine, bromine, methyl and ethyl.

$R^6$ and $R^7$ independently of one another each particularly preferably represent phenyl, naphthyl, dihydronaphthyl and tetrahydronaphthyl, each of which is optionally mono- to trisubstituted by identical or different substituents, possible substituents being:
cyano, nitro, amino, fluorine, chlorine, bromine; in each case optionally fluorine- or chlorine-substituted methyl, ethyl, n- or i-propyl, n-, i-, s- or t-butyl, methoxy, ethoxy, n- or i-propoxy, n-, i-, s- or t-butoxy, methylamino, ethylamino, n- or i-propylamino or dimethylamino; in each case optionally fluorine- and/or chlorine-substituted acetyl, propionyl, methoxycarbonyl, ethoxycarbonyl, n- or i-propoxycarbonyl, methylthio, methylsulphinyl, methylsulphonyl, ethylthio, ethylsulphinyl or ethylsulphonyl; aminocarbonyl, aminothiocarbonyl, methylaminocarbonyl, ethylaminocarbonyl, n- or i-propylaminocarbonyl, dimethylaminocarbonyl, diethyl aminocarbonyl, aminosulphonyl, methylaminosulphonyl, ethylaminosulphonyl, dimethylaminosulphonyl and diethylaminosulphonyl;
and also in each case optionally cyano-, nitro-, fluorine-, chlorine-, methyl-, ethyl-, n- or i-propyl-, n-, i-, s- or t-butyl-, trifluoromethyl-, methoxy-, ethioxy-, n- or i-propoxy-, methylthio-, ethylthio-, n- or i-propylthio-, methylsulphinyl-, ethlylsulphinyl-, n- or i-propylsulphinl-, methylsulphonyl-, ethylsulphonyl-, n- or i-propylsulphonyl-, difluoromethoxy- or trifluoromethoxy-, trifluoromethylthio-, trifluoromethylsulphinyl- or trifluoromethylsulphonyl-substituted phenyl, phenoxy, phenylthio, phenylsulphinyl, phenylsulphonyl, benzyl or phenylamino;
furthermore represent cyclopentane, cyclohexane, cyclopentene and cyclohexene, each of which is optionally mono- to trisubstituted by identical or different substituents selected from the group consisting of fluorine, chlorine, methyl, ethyl, n- or i-propyl, optionally substituted cyclohexyl-$C_1$–$C_4$-alkyl, optionally substituted phenyl-$C_1$–$C_4$-alkyl, methoxy, ethoxy, trifluoromethyl and trifluoromethoxy;
and also represent a saturated or partially unsaturated or unsaturated mono- or bicyclic nitrogen-free heterocycle having 4 to 9 C atoms and 1 to 3 identical or different heteroatoms, such as O and S atoms, which is optionally mono- to pentasubstituted by identical or different substituents, possible substituents being:
cyano, nitro, fluorine, chlorine, bromine, methyl, ethyl, n- or i-propyl, methoxy, ethoxy, trifluoromethyl, trifluoromethoxy, trifluoromethylthio and dimethylamino.

$R^8$ particularly preferably represents methyl, ethyl, n- or i-propyl; n-, i-, s- or t-butyl or represents phenyl which is optionally mono- to trisubstituted by identical or different substituents, possible substituents being the phenyl substituents mentioned under $R^6$.

X particularly preferably represents a single bond and also represents the groupings: —$CH)_2$—, —$(CH_2)_2$—, —$(CH_2)_3$—, —$(CH_2)_4$—, —$H(CH_3)$—, —$CH(C_2H_5)$—, —$CH(CH_3)CH_2$—, —$CH_2CH(CH_3)$—, —$CH(CH_3)CH_2CH_2$—, —$C(CH_3)_2$—, —$CH_2C(CH_3)_2$—, —$CH_2CH(C_3)CH_2$—, —$CH(CH_3)$—$CH(CH_3)$—, —$CH(C_2H_5)CH_2CH_2$—; —$CH_2O$—, —$CH_2S$—, —$(CH_2)_2O$—, —$(CH_2)_2S$—, —$CH(CH_3)CH_2O$—, —$CH(C_2H_5)CH_2O$—; —$CH_2OCH_2$—, $CH_2SCH_2$—, —$CH(CH_3)CH_2OCH_2$—, —$CH(C_2H_5)CH_2OCH_2$—; —$CH=CH$—, —$C(CH_3)=CH$, —$CH_2$—$CH=CH$—, —$CH_2$—$C(CH_3)=CH$—, —$C\equiv C$—, —$CH_2$—$C\equiv C$—, —$CH(CH_3)$—$C\equiv C$—; —$CH_2$—$N(CH_3)$—, —$(CH_2)_2$—$N(CH_3)$—, —$(CH_2)_3$—$N(CH_3)$—, —$CH_2$—$N(C_2H_5)$—, —$(CH_2)_2$—$N(C_2H_5)$—, —$(CH_2)_3$—$N(C_2H_5)$—, —$CH_2$—$N(CH_3)$—$CH_2$—, —$(CH_2)_2$—$N(CH_3)$—$CH_2$—, —$(CH_2)_3$—$N(CH_3)$—$CH_2$—, —$CH_2$—$N(C_2H_5)$—$CH_2$—, —$(CH_2)_2$—$N(C_2H_5)$—$CH_2$—, —$(CH_2)_3$—$N(C_2H_5)$—$CH_2$—.

Y particularly preferably represents a single bond and also represents the groupings —$OCH_2$—, —$O(CH_2)_2$—, —$O(CH_2)_3$—, —$O(CH_2)_4$—, —$OCH(CH_3)$—, —$OCH(C_2H_5)$—, —$OCH(CH_3)CH_2$—, —$OCH_2CH(CH_3)$—, —$OCH(C_2H_5)CH_2$—, —$OCH(CH_3)CH_2CH_2$—, —$OCH(C_2H_5)CH_2CH_2$—, —$OCH_2CH(CH_3)CH_2$—, —$OCH_2CH_2CH(CH_3)$—, —$OCH_2CH_2O$—, —OCH$_2$CH$_2$S—, —OCH$_2$CH$_2$SO—, —OCH$_2$CH$_2$SO$_2$—, —OCH(CH$_3$)CH$_2$O—, —OCH(C$_2$H$_5$)CH$_2$O—, —OCH(CH$_3$)CH$_2$S—, —OCH(C$_2$H$_5$)CH$_2$S—, —OCH$_2$CH$_2$OCH$_2$—, —OCH$_2$CH$_2$SCH$_2$—, —OCH(CH$_3$)CH$_2$OCH$_2$—, —OCH(CH$_3$)CH$_2$SCH$_2$—, —OCH(C$_2$H$_5$)CH$_2$OCH$_2$—, —OCH(C$_2$H$_5$)CH$_2$SCH$_2$—.

The particularly preferred definitions are given with the proviso that for R=CN and R$^2$=H the compounds in which

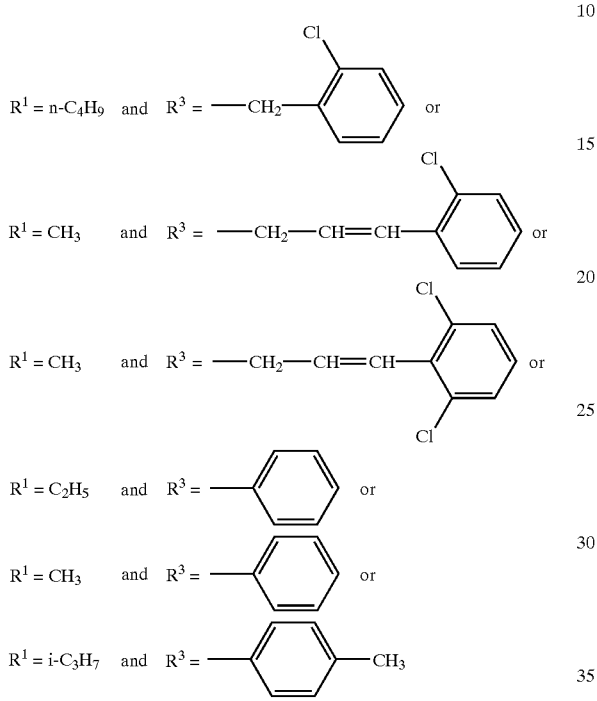

are excluded.

R very particularly preferably represents cyano or nitro.

R$^1$ very particularly preferably represents hydrogen, methyl, ethyl, n- or i-propyl, cyclopropyl or phenyl.

R$^2$ very particularly preferably represents hydrogen, methyl, ethyl, n- or i-propyl or cyclopropyl.

R$^3$ very particularly preferably represents the groupings

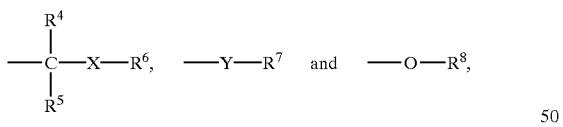

where

R$^4$ and R$^5$ independently of one another each very particularly preferably represent hydrogen, methyl ethyl, n- or i-propyl and also cyclopropyl.

R$^6$ and R$^7$ independently of one another each very particularly preferably represent phenyl or naphthyl, each of which is optionally mono- to trisubstituted by identical or different substituents, possible substituents being:
  cyano, nitro, amino, fluorine, chlorine, bromine, methyl, ethyl, n- or i-propyl, n-, i-, s- or t-butyl, methoxy, ethoxy, n- or i-propoxy, trifluoromethyl, difluoromethyl, trifluoromethoxy, difuoromethoxy, trifluoromethylthio, methylamino, dimethylamino, acetyl, propionyl, methoxycarbonyl, ethoxycarbonyl, methylthio, methylsulphinyl, methylsulphonyl, methylaminocarbonyl, ethylaminocarbonyl, n- or i-propylaminocarbonyl, dimethylaminocarbonyl and diethylaminocarbonyl; and also in each case optionally cyano-, nitro-, fluorine-, chlorine-, methyl-, methoxy-, methylthio-, methylsulphinyl-, methylsulphonyl-, trifluoromethyl- or trifluoromethoxy-, trifluoromethylthio-, trifluoromethylsulphinyl- or trifluoromethylsulphonyl-substituted phenyl, phenoxy, phenylthio, phenylsulphinyl, phenylsulphonyl, benzyl or phenylamino;

furthermore represent cyclopentane or cyclohexane, each of which is optionally mono- to trisubstituted by identical or different substituents selected from the group consisting of fluorine, chlorine, methyl, ethyl, i-propyl, methoxy, ethoxy, trifluoromethyl and trifluoromethoxy;

and also represent the following heterocycles which are optionally mono- to pentasubstituted by identical or different substituents:

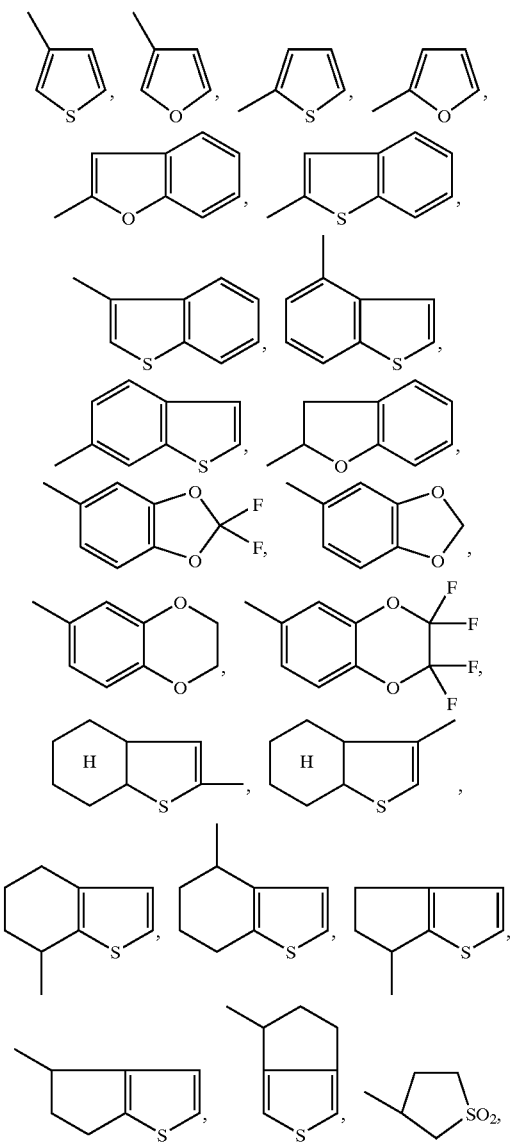

-continued

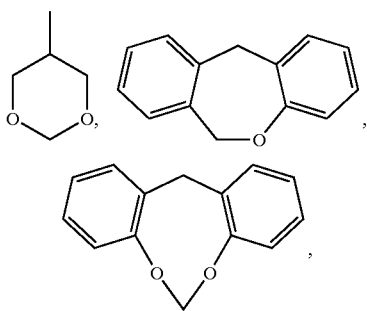

possible (additional) substituents being:

cyano, nitro, fluorine, chlorine, bromine, methyl, ethyl, n- or i-propyl, methoxy, trifluoromethyl or dimethylamino or optionally substituted phenyl, the possible substituents for the phenyl radical being the substituents which have also been mentioned under $R^6$ for the phenyl radical.

$R^8$ very particularly preferably represents methyl, ethyl, n- or i-propyl; n-, i-, s- or t-butyl or represents phenyl which is optionally mono- to trisubstituted by identical or different substituents, possible substituents being the phenyl substituents mentioned under $R^6$.

X very particularly preferably represents a single bond and also represents the groupings, —CH$_2$—, —(CH$_2$)$_2$—, —(CH$_2$)$_3$—, —CH(CH$_3$)—, —C(CH$_3$)$_2$—, —CH$_2$C(CH$_3$)$_2$—, —CH(CH$_3$)CH$_2$—, —CH$_2$—, —CH$_2$S—, —(CH$_2$)$_2$O—, —(CH$_2$)$_2$S—, —CH$_2$OCH$_2$—, CH$_2$SCH$_2$—, —C(CH$_3$)=CH, —C≡C—, —(CH$_2$)$_3$—N(CH$_3$)—, —(CH$_2$)$_3$—N(C$_2$H$_5$)—, —(CH$_2$)$_3$—N(CH$_3$)—CH$_2$—, —(CH$_2$)$_3$—N(C$_2$H$_5$)—CH$_2$—.

Y very particularly preferably represents a single bond and also represents the groupings —OCH$_2$—, —O(CH$_2$)$_2$—, —O(CH$_2$)$_3$—, —O(CH$_2$)$_4$—, —OCH(CH$_3$)—, —OCH(C$_2$H$_5$)—, —OCH(CH$_3$)CH$_2$—, —OCH(CH$_3$)CH$_2$CH$_2$—, —OCH(C$_2$H$_5$)CH$_2$CH$_2$—, —OCH$_2$CH$_2$O—, —OCH$_2$CH$_2$S—, —OCH$_2$CH$_2$SO—, —OCH$_2$CH$_2$SO$_2$—, —OCH(CH$_3$)CH$_2$O—, —OCH(C$_2$H$_5$)CH$_2$O—, —OCH(CH$_3$)CH$_2$S—, —OCH(C$_2$H$_5$)CH$_2$S—, —OCH$_2$CH$_2$OCH$_2$—, —OCH$_2$CH$_2$SCH$_2$—.

The very particularly preferred definitions are given with the proviso that for R=CN and $R^2$=H the compounds in which

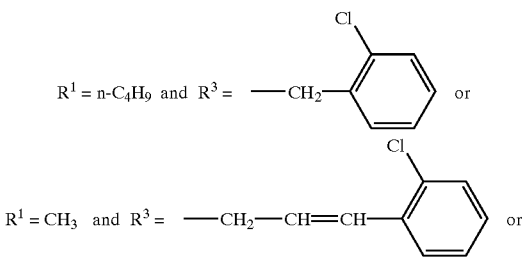

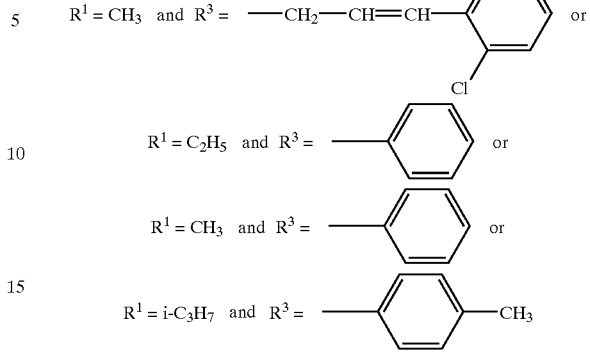

are excluded.

Preferred compounds according to the invention are substances of the formulae (Ia) to (Ih):

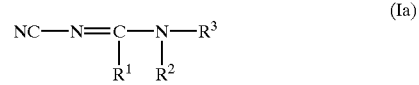 (Ia)

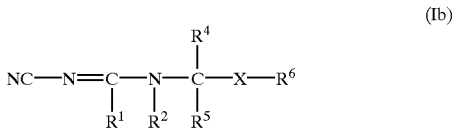 (Ib)

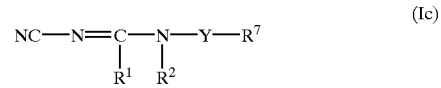 (Ic)

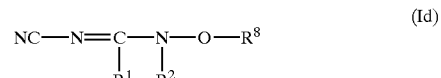 (Id)

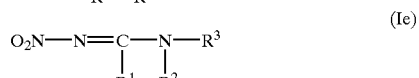 (Ie)

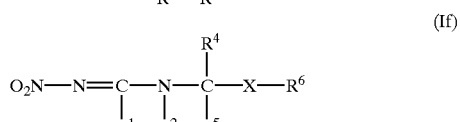 (If)

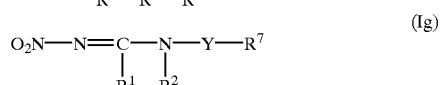 (Ig)

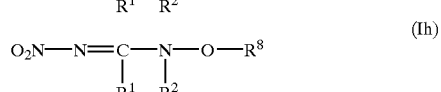 (Ih)

in which $R^1$, $R^2$, $R^3$, $R^4$, $R^5$, $R^6$, $R^7$, $R^8$, X and Y each have the general, preferred, particularly preferred and very particularly preferred meanings mentioned above.

Particular emphasis is here given to the compounds of the above formula (Ib).

Preferred compounds according to the invention are also substances of the formulae (IA) to (IW):

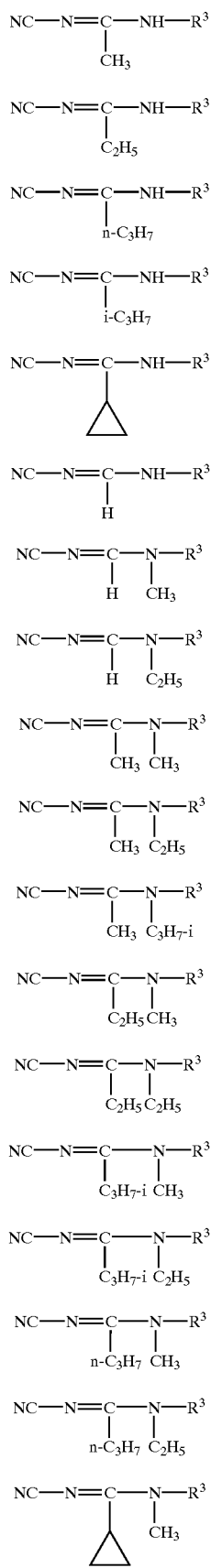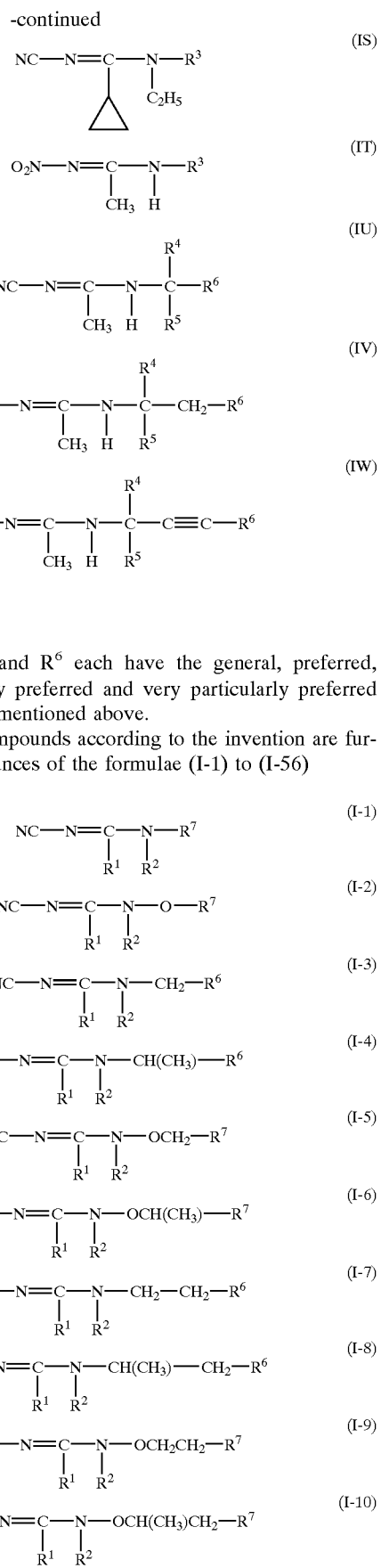
in which
R³, R⁴, R⁵ and R⁶ each have the general, preferred, particularly preferred and very particularly preferred meanings mentioned above.
Preferred compounds according to the invention are furthermore substances of the formulae (I-1) to (I-56)

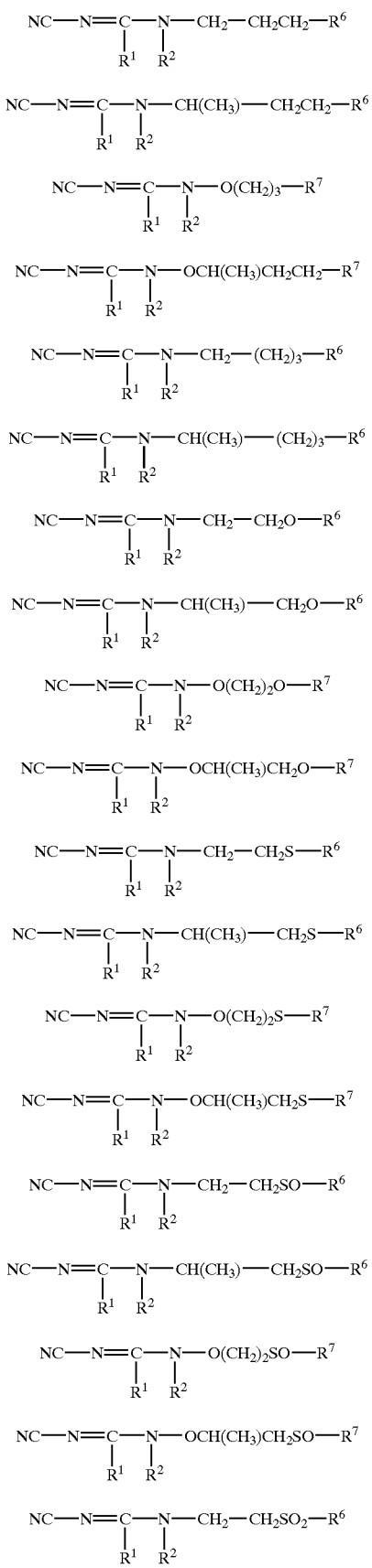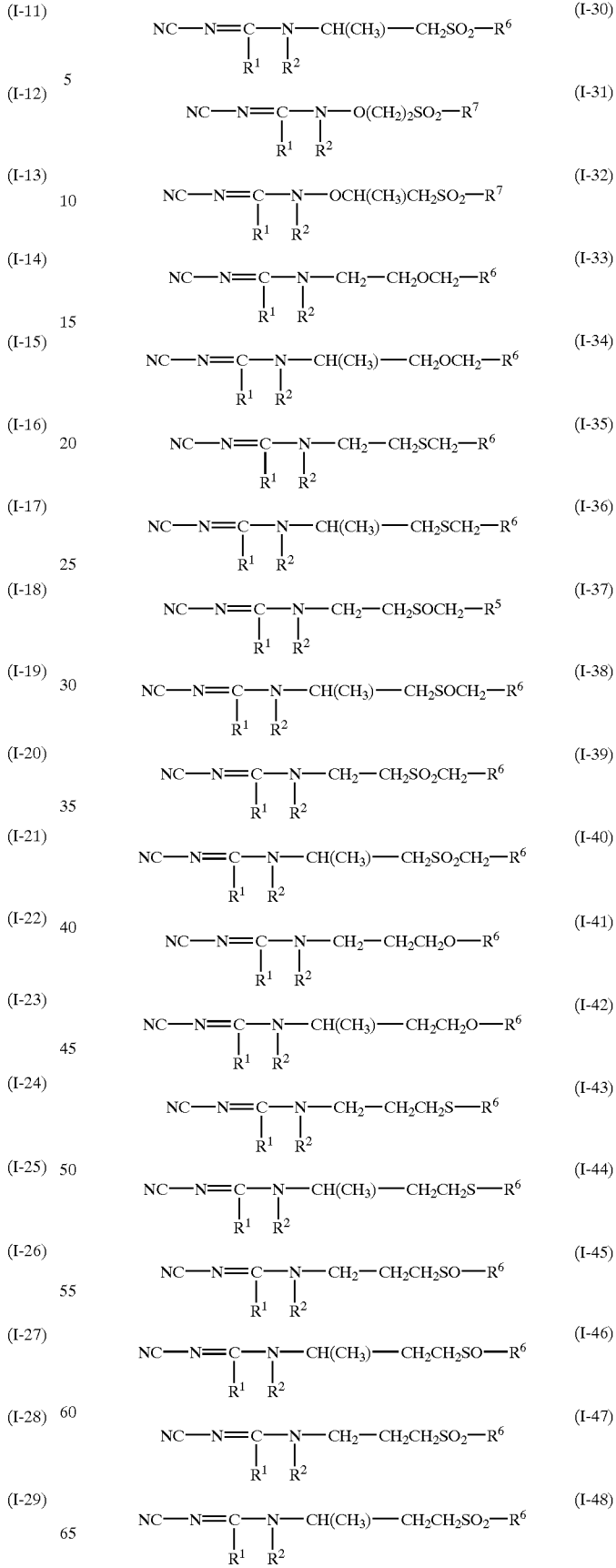

-continued

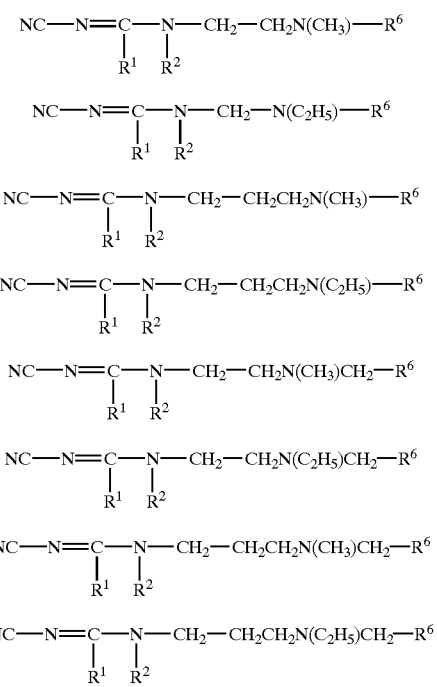

in which
R$^1$, R$^2$, R$^6$ and R$^7$ each have the general; preferred, particularly preferred and very particularly preferred meanings mentioned above.

The abovementioned general or preferred radical definitions or illustrations apply both to the end products and, correspondingly, to the starting materials and intermediates. These radical definitions can be combined with each other as desired, i.e. including combinations between the respective preferred ranges.

Preference according to the invention is given to the compounds of the formula (I) which contain a combination of the meanings mentioned above as being preferred (preferable).

Particular preference according to the invention is given to the compounds of the formula (I) which contain a combination of the meanings given above as being particularly preferred.

Very particular preference according to the invention is given to the compounds of the formula (I) which contain a combination of the meanings listed above as being very particularly preferred.

In the radical definitions listed above and below, hydrocarbon radicals, such as alkyl or alkenyl, are in each case straight-chain or branched as far as this is possible—also in combination with heteroatoms, such as in alkoxy or alkylthio.

Specifically, the following compounds may be mentioned:

TABLE 1

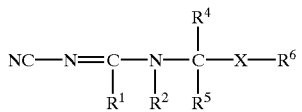
(Ib)

Compounds of Table 1 correspond to the general formula (Ib), in which

R$^1$=CH$_3$
R$^2$=H
C(R$^4$,R$^5$)=CH$_2$
XR$^6$=as listed below:

| XR$^6$ |
|---|
|  |
| 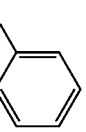 |
| 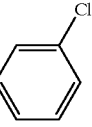 |
|  |
| 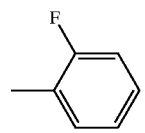 |
| 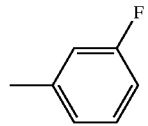 |
|  |
| 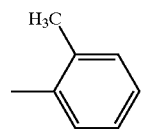 |
| 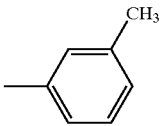 |
| 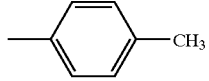 |
| 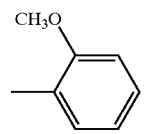 |

-continued
| $XR^6$ | $XR^6$ |
|---|---|
| 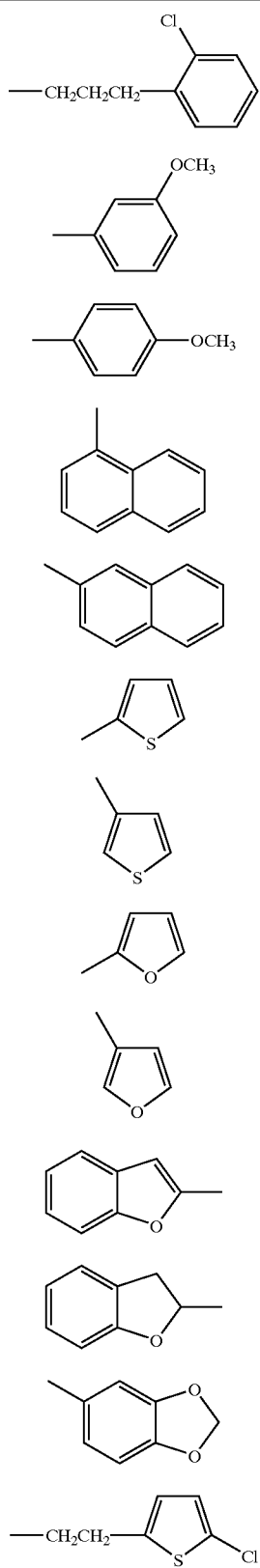 | 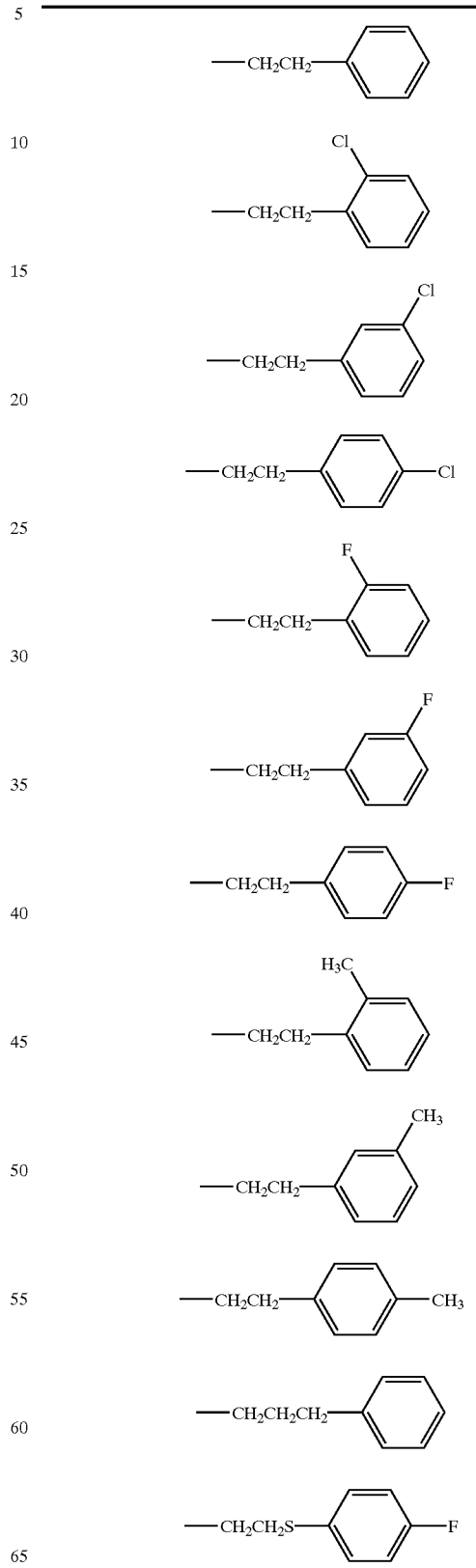 |

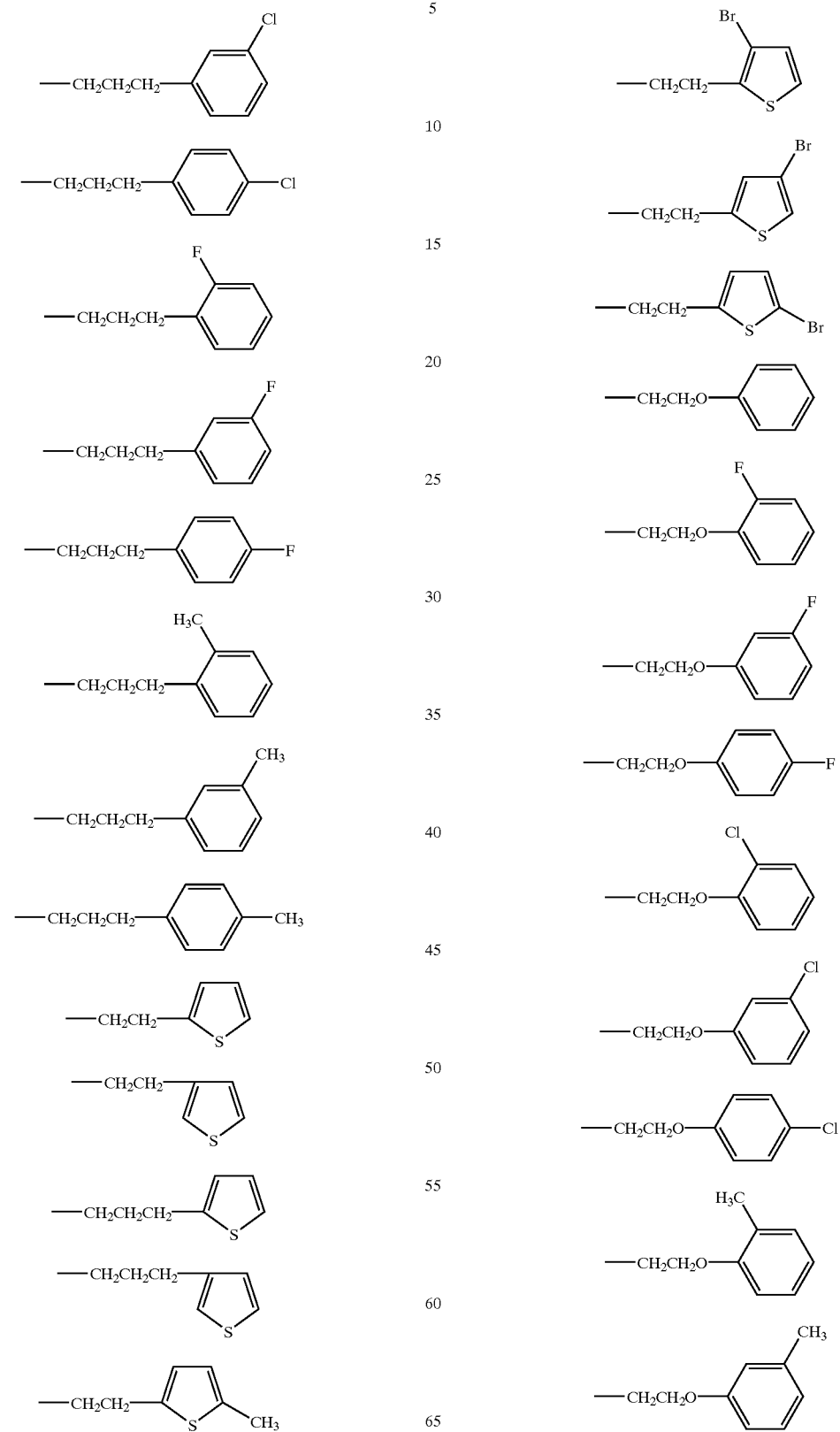

-continued
XR⁶
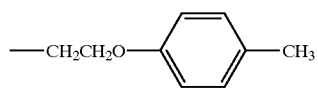
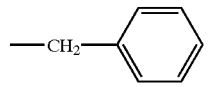
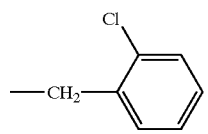
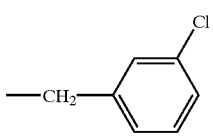
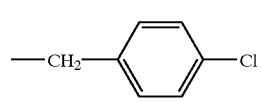
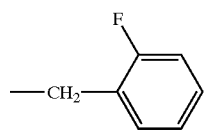
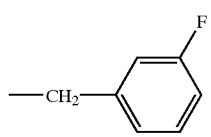
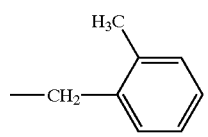
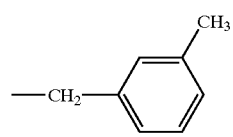
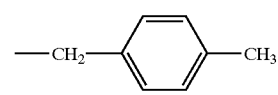
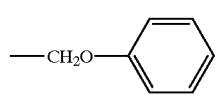
-continued
XR⁶
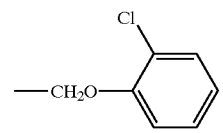
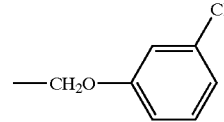
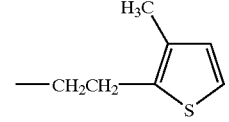
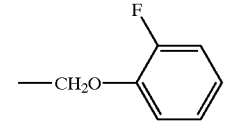
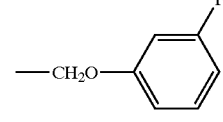
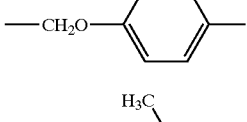
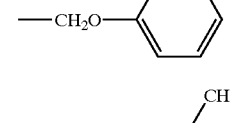
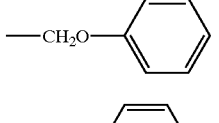
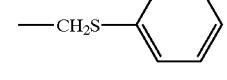
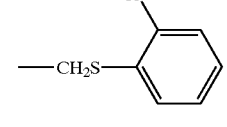
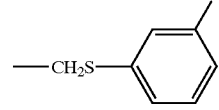

| XR⁶ (continued) |
|---|
| —CH₂S—C₆H₄—Cl (4-) |
| —CH₂CH₂S—C₆H₅ |
| —CH₂S—C₆H₄—F (2-) |
| —CH₂S—C₆H₄—F (3-) |
| —CH₂S—C₆H₄—F (4-) |
| —CH₂S—C₆H₄—CH₃ (2-) |
| —CH₂S—C₆H₄—CH₃ (3-) |
| —CH₂S—C₆H₄—CH₃ (4-) |
| —CH₂OCH₂—C₆H₅ |
| —CH₂OCH₂—C₆H₄—Cl (2-) |
| —CH₂OCH₂—C₆H₄—Cl (3-) |
| —CH₂OCH₂—C₆H₄—Cl (4-) |
| —CH₂O—C₆H₄—Cl (4-) |
| —CH₂OCH₂—C₆H₄—F (2-) |
| —CH₂OCH₂—C₆H₄—F (3-) |
| —CH₂OCH₂—C₆H₄—F (4-) |
| —CH₂OCH₂—C₆H₄—CH₃ (2-) |
| —CH₂OCH₂—C₆H₄—CH₃ (3-) |
| —CH₂OCH₂—C₆H₄—CH₃ (4-) |
| —CH₂SCH₂—C₆H₅ |
| —CH₂SCH₂—(2-thienyl) |
| —CH₂SCH₂—(3-thienyl) |

Table 2
Compounds of Table 2 correspond to the general formula (Ib) in which
$C(R^4,R^5)=CH(CH_3)$
$R^1$, $R^2$ and $XR^6$=as listed in Table 1.

Table 3
Compounds of Table 3 correspond to the general formula (Ib) in which
$C(R^4,R^5)=CH(C_2H_5)$
$R^1$, $R^2$ and $XR^6$=as listed in Table 1.

Table 4
Compounds of Table 4 correspond to the general formula (Ib) in which
$C(R^4,R^5)=CH(C_3H_7\text{-}i)$
$R^1$, $R^2$ and $XR^6$=as listed in Table 1.

Table 5
Compounds of Table 5 correspond to the general formula (Ib) in which
$C(R^4,R^5)=CH(C_3H_7\text{-n})$
$R^1$, $R^2$ and $XR^6$=as listed in Table 1.
Table 6
Compounds of Table 6 correspond to the general formula (Ib) in which
$C(R^4,R^5)=C(CH_3)_2$
$R^1$, $R^2$ and $XR^6$=listed in Table 1.
Tables 7–12
Compounds of Tables 7–12 correspond to the general formula (Ib) in which
$R^1=C_2H_5$
$R^2=H$
$C(R^4,R^5)$=as listed in Tables 1to 6
$XR^6$=as listed in Table 1.
Tables 13–18
Compounds of Tables 13–18 correspond to the general formula (Ib) in which
$R^1=C_3H_7\text{-i}$
$R^2=H$
$C(R^4,R^5)$=as listed in Tables 1to 6
$XR^6$=as listed in Table 1.
Tables 19–24
Compounds of Tables 19–24 correspond to the general formula (Ib) in which
$R^1=C_3H_7\text{-n}$
$R^2=H$
$C(R^4,R^5)$=as listed in Tables 1to 6
$XR^6$=as listed in Table 1.
Tables 25–30
Compounds of Tables 25–30 correspond to the general formula (Ib) in which
$R^1=$—◁
$R^2=H$
$C(R^4,R^5)$=as listed in Tables 1to 6
$XR^6$=as listed in Table 1.
Tables 31–36
Compounds of Tables 31–36 correspond to the general formula (Ib) in which
$R^1=H$
$R^2=H$
$C(R^4,R^5)$=as listed in Tables 1to 6
$XR^6$=as listed in Table 1.
Tables 37–42
Compounds of Tables 37–42 correspond to the general formula (Ib) in which
$R^1=H$
$R^2=CH_3$
$C(R^4,R^5)$=as listed in Tables 1to 6
$XR^6$=as listed in Table 1.
Tables 43–48
Compounds of Tables 43–48 correspond to the general formula (Ib) in which
$R^1=H$
$R^2=C_2H_5$
$C(R^4,R^5)$=as listed in Tables 1to 6
$XR^6$=as listed in Table 1.
Tables 49–54
Compounds of Tables 49–54 correspond to the general formula (Ib) in which
$R^1=CH_3$
$R^2=CH_3$
$C(R^4,R^5)$=as listed in Tables 1to 6
$XR^6$=as listed in Table 1.
Tables 55–60
Compounds of Tables 55–60 correspond to the general formula (Ib) in which
$R^1=CH_3$
$R^2=C_2H_5$
$C(R^4,R^5)$=as listed in Tables 1to 6
$XR^6$=as listed in Table 1.
Tables 61–66
Compounds of Tables 61–66 correspond to the general formula (Ib) in which
$R^1=CH_3$
$R^2=C_3H_7\text{-i}$
$C(R^4,R^5)$=as listed in Tables 1to 6
$XR^6$=as listed in Table 1.
Tables 67–72
Compounds of Tables 67–72 correspond to the general formula (Ib) in which
$R^1=C_2H_5$
$R^2=CH_3$
$C(R^4,R^5)$=as listed in Tables 1 to 6
$XR^6$=as listed in Table 1.
Tables 73–78
Compounds of Tables 73–78 correspond to the general formula (Ib) in which
$R^1=CH_5$
$R^2=C_2H_5$
$C(R^4,R^5)$=as listed in Tables 1to 6
$XR^6$=as listed in Table 1.
Tables 79–84
Compounds of Tables 79–84 correspond to the general formula (Ib) in which
$R^1=C_3H_7\text{-i}$
$R^2=CH_3$
$C(R^4,R^5)$=as listed in Tables 1to 6
$XR^6$=as listed in Table 1.
Tables 85–90
Compounds of Tables 85–90 correspond to the general formula (Ib) in which
$R^1=C_3H_7\text{-i}$
$R^2=C_2H_5$
$C(R^4,R^5)$=as listed in Tables 1to 6
$XR^6$=as listed in Table 1.
Tables 91–96
Compounds of Tables 91–96 correspond to the general formula (Ib) in which
$R^1=C_3H_7\text{-n}$
$R^2=CH_3$
$C(R^4,R^5)$=as listed in Tables 1to 6
$XR^6$=as listed in Table 1.
Tables 97–102
Compounds of Tables 97–102 correspond to the general formula (Ib) in which
$R^1=C_3H_7\text{-n}$
$R^2=C_2H_5$
$C(R^4,R^5)$=as listed in Tables 1 to 6
$XR^6$=as listed in Table 1.

Tables 103–108

Compounds of Tables 103–108 correspond to the general formula (Ib) in which $R^1$=—◁
$R^2$=CH$_3$
C($R^4$,$R^5$)=as listed in Tables 1 to 6
X$R^6$=as listed in Table 1.

Tables 109–114

Compounds of Tables 109–114 correspond to the general formula (Ib) in which $R^1$=—◁
$R^2$=C$_2$H$_5$
C($R^4$,$R^5$)=as listed in Tables 1 to 6
X$R^6$=as listed in Table 1.

TABLE 115

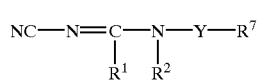
(Ic)

Compounds of Table 115 correspond to the general formula (Ic) in which $R^1$=CH$_3$
$R^2$=H
Y$R^7$=as listed below:

| YR$^7$ |
|---|
| 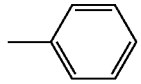 |
| 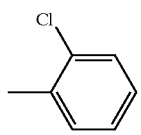 |
| 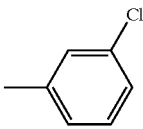 |
|  |
| 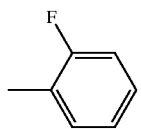 |
| 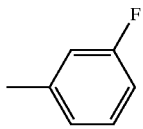 |

-continued

| YR$^7$ |
|---|
|  |
| 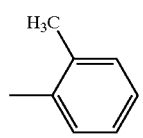 |
| 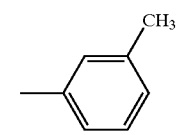 |
| 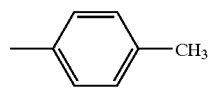 |
| 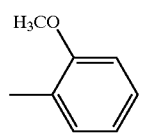 |
| 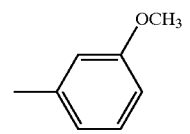 |
| 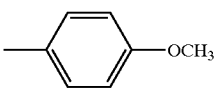 |
| 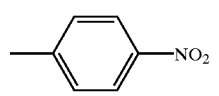 |
| 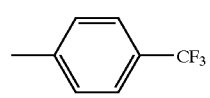 |
| 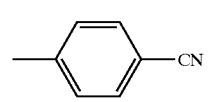 |
| 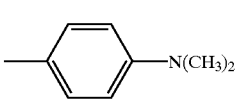 |
| 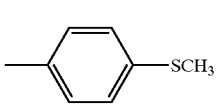 |
| 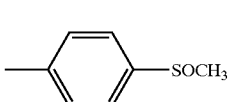 |

| YR⁷ |
|---|
| 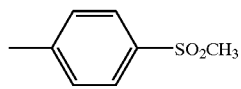 |
| 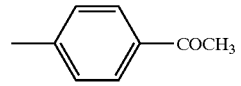 |
| 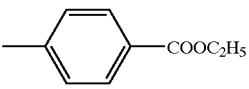 |
| 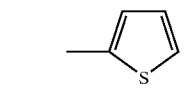 |
| 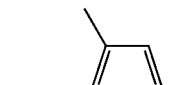 |
| 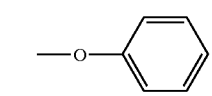 |
| 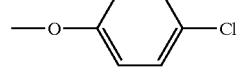 |
| 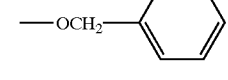 |
| 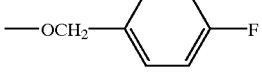 |
| 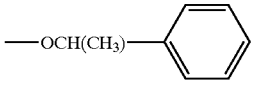 |
| 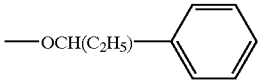 |
| 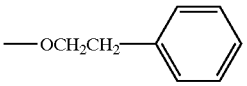 |
| 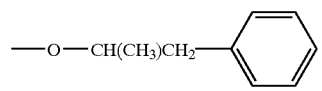 |
| 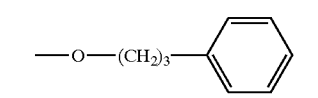 |
| 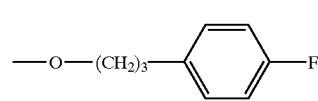 |

| YR⁷ |
|---|
| 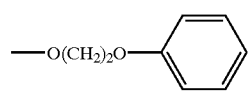 |
| 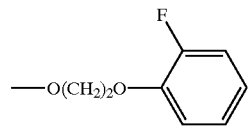 |
| 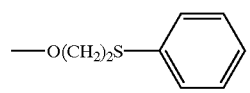 |
| 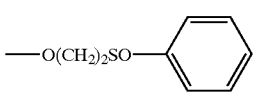 |
| 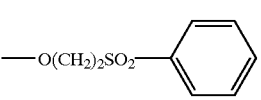 |
| 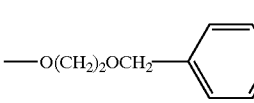 |
| 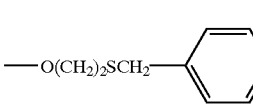 |

Table 116
Compounds of Table 116 correspond to the general formula (Ic) in which
$R^1=C_2H_5$
$R^2=H$
$YR^7$=as listed in Table 115.

Table 117
Compounds of Table 117 correspond to the general formula (Ic) in which
$R^1=C_3H_7\text{-}i$
$R^2=H$
$YR^7$=as listed in Table 115.

Table 118
Compounds of Table 118 correspond to the general formula (Ic) in which
$R^1=C_3H_7\text{-}n$
$R^2=H$
$YR^7$=as listed in Table 115.

Table 119
Compounds of Table 119 correspond to the general formula (Ic) in which
$R^1=$—◁
$R^2=H$
$YR^7$=as listed in Table 115.

Table 120
Compounds of Table 120 correspond to the general formula (Ic) in which
$R^1=H$
$R^2=H$ YR⁷=as listed in Table 115.

Table 121

Compounds of Table 121 correspond to the general formula (Ic) in which
$R^1$=H
$R^2$=CH$_3$
YR⁷=as listed in Table 115.

Table 122

Compounds of Table 122 correspond to the general formula (Ic) in which
$R^1$=H
$R^2$=C$_2$H$_5$
YR⁷=as listed in Table 115.

Table 123

Compounds of Table 123 correspond to the general formula (Ic) in which
$R^1$=H
$R^2$=C$_3$H$_7$-i
YR⁷=as listed in Table 115.

Table 124

Compounds of Table 124 correspond to the general formula (Ic) in which
$R^1$=CH$_3$
$R^2$=CH$_3$
YR⁷=as listed in Table 115.

Table 125

Compounds of Table 125 correspond to the general formula (Ic) in which
$R^1$=CH$_3$
$R^2$=C$_2$H$_5$
YR⁷=as listed in Table 115.

Table 126

Compounds of Table 126 correspond to the general formula (Ic) in which
$R^1$=CH$_3$
$R^2$=C$_3$H$_7$-i
YR⁷ as listed in Table 115.

Table 127

Compounds of Table 127 correspond to the general formula (Ic) in which
$R^1$=C$_2$H$_5$
$R^2$=CH$_3$
YR⁷=as listed in Table 115.

Table 128

Compounds of Table 128 correspond to the general formula (Ic) in which
$R^1$=C$_2$H$_5$
$R^2$=C$_2$H$_5$
YR⁷=as listed in Table 115.

Table 129

Compounds of Table 129 correspond to the general formula (Ic) in which
$R^1$=C$_3$H$_7$-i
$R^2$=CH$_3$
YR⁷=as listed in Table 115.

Table 130

Compounds of Table 130 correspond to the general formula (Ic) in which
$R^1$=C$_3$H$_7$-i
$R^2$=C$_2$H$_5$
YR⁷=as listed in Table 115.

Table 131

Compounds of Table 131 correspond to the general formula (Ic), in which
$R^1$=CH$_3$
$R^2$=◁
YR⁷=as listed in Table 115.

The following compounds may be mentioned as being preferred:

TABLE a (Ib)

$$NC-N=C-N-C-X-R^6$$
with substituents $R^1$, $R^2$, $R^5$ on the chain and $R^4$ on the second C.

| $R^1$ | $R^2$ | $R^4$ | $R^5$ | X | $R^6$ |
|---|---|---|---|---|---|
| CH$_3$ | H | H | CH$_3$ | —CH$_2$CH$_2$— |  |
| CH$_3$ | H | H | CH$_3$ | —CH$_2$CH$_2$— | 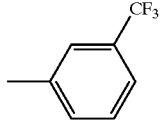 |
| CH$_3$ | H | H | CH$_3$ | —CH$_2$CH$_2$— | 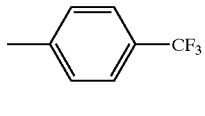 |
| CH$_3$ | H | H | CH$_3$ | —CH$_2$CH$_2$— | 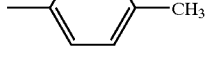 |

TABLE a-continued $$NC-N=\underset{R^1}{\underset{|}{C}}-\underset{R^2}{\underset{|}{N}}-\underset{R^5}{\underset{|}{\overset{R^4}{\overset{|}{C}}}}-X-R^6 \quad \text{(Ib)}$$

| R¹ | R² | R⁴ | R⁵ | X | R⁶ |
|---|---|---|---|---|---|
| CH₃ | H | H | CH₃ | —CH₂CH₂— | 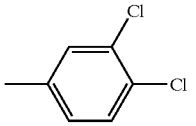 3,4-dichlorophenyl |
| CH₃ | H | H | CH₃ | —CH₂CH₂— | 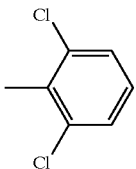 2,6-dichlorophenyl |
| CH₃ | H | CH₃ | CH₃ | —CH₂CH₂— | 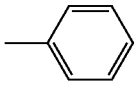 phenyl |
| CH₃ | H | CH₃ | CH₃ | —CH₂CH₂— | 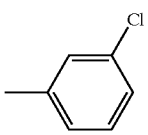 3-chlorophenyl |
| CH₃ | H | CH₃ | CH₃ | —CH₂CH₂— | 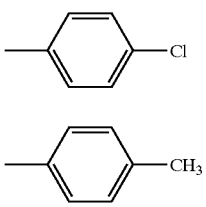 4-chlorophenyl |
| CH₃ | H | CH₃ | CH₃ | —CH₂CH₂— | 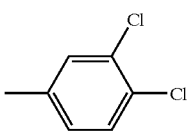 4-methylphenyl |
| CH₃ | H | CH₃ | CH₃ | —CH₂CH₂— | 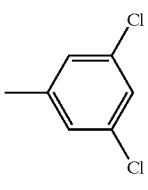 3,4-dichlorophenyl |
| CH₃ | H | CH₃ | CH₃ | —CH₂CH₂— | 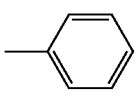 3,5-dichlorophenyl |
| CH₃ | H | H | CH₃ | —CH(CH₃)CH₂— | 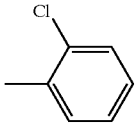 phenyl |
| CH₃ | H | H | CH₃ | —CH(CH₃)CH₂— | 2-chlorophenyl |

TABLE a-continued $$NC-N=\underset{R^1}{\overset{}{C}}-\underset{R^2}{\overset{}{N}}-\underset{R^5}{\overset{R^4}{C}}-X-R^6 \quad (Ib)$$

| R¹ | R² | R⁴ | R⁵ | X | R⁶ |
|---|---|---|---|---|---|
| CH₃ | H | H | CH₃ | —CH(CH₃)CH₂— | 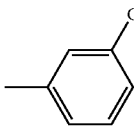 3-Cl-C₆H₄ |
| CH₃ | H | H | CH₃ | —CH(CH₃)CH₂— | 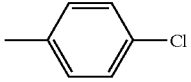 4-Cl-C₆H₄ |
| CH₃ | H | H | CH₃ | —CH(CH₃)CH₂— |  4-F-C₆H₄ |
| CH₃ | H | H | CH₃ | —CH(CH₃)CH₂— |  4-Br-C₆H₄ |
| CH₃ | H | H | CH₃ | —CH(CH₃)CH₂— | 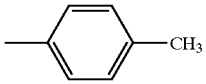 4-CH₃-C₆H₄ |
| CH₃ | H | H | CH₃ | —CH(CH₃)CH₂— | 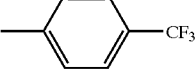 4-CF₃-C₆H₄ |
| CH₃ | H | H | H | —CH(CH₃)CH₂— | 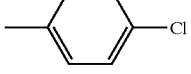 4-Cl-C₆H₄ |
| CH₃ | H | H | H | —CH(CH₃)CH₂— | 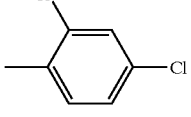 2,4-Cl₂-C₆H₃ |
| CH₃ | H | H | CH₃ | —(CH₂)₃N(CH₃)— |  C₆H₅ |
| CH₃ | H | H | CH₃ | —(CH₂)₃N(C₂H₅)— |  C₆H₅ |
| CH₃ | H | H | H | —CH(CH₃)— |  C₆H₅ |
| CH₃ | H | H | H | —CH(CH₃)— | 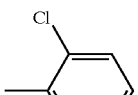 2-Cl-C₆H₄ |

TABLE a-continued
$$NC-N=\underset{R^1}{\overset{}{C}}-\underset{R^2}{\overset{R^4}{N}}-\underset{R^5}{\overset{}{C}}-X-R^6 \qquad (Ib)$$
| R¹ | R² | R⁴ | R⁵ | X | R⁶ |
|---|---|---|---|---|---|
| CH₃ | H | H | H | —CH(CH₃)— | 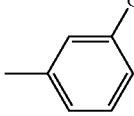 |
| CH₃ | H | H | H | —CH(CH₃)— |  |
| CH₃ | H | H | H | —CH(CH₃)— |  |
| CH₃ | H | H | H | —CH(CH₃)— |  |
| CH₃ | H | H | H | —CH(CH₃)— | 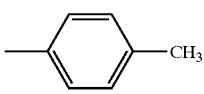 |
| CH₃ | H | H | H | —CH(CH₃)— |  |
| CH₃ | H | CH₃ | CH₃ | —C≡C— | 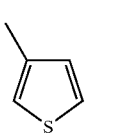 |
| CH₃ | H | H | CH₃ | — | 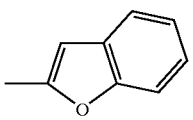 |
| CH₃ | H | H | CH₃ | — | 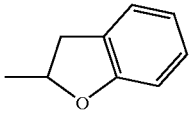 |
| CH₃ | H | H | CH₃ | — | 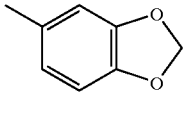 |
| CH₃ | H | H | CH₃ | — | 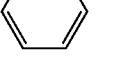 |
| CH₃ | H | H | CH₃ | — | 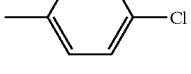 |

TABLE a-continued
(Ib)
$$NC-N=\underset{R^1}{\overset{}{C}}-\underset{R^2}{\overset{}{N}}-\underset{R^5}{\overset{R^4}{C}}-X-R^6$$
| $R^1$ | $R^2$ | $R^4$ | $R^5$ | X | $R^6$ |
|-------|-------|-------|-------|---|-------|
| CH$_3$ | H | H | n-C$_3$H$_7$ | — | 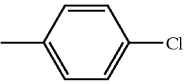 |
| CH$_3$ | H | H | H | —C(CH$_3$)=CH— | 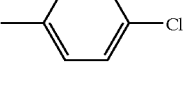 |
| CH$_3$ | H | H | CH$_3$ | —CH$_2$O— |  |
| CH$_3$ | H | H | CH$_3$ | —CH$_2$O— | 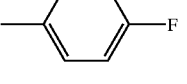 |
| CH$_3$ | H | H | CH$_3$ | —CH$_2$O— | 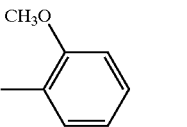 |
| CH$_3$ | H | H | CH$_3$ | —CH$_2$O— | 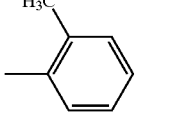 |
| CH$_3$ | H | H | CH$_3$ | —CH$_2$O— | 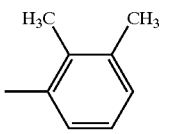 |
| CH$_3$ | H | H | CH$_3$ | —CH$_2$O— | 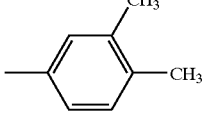 |
| CH$_3$ | H | H | CH$_3$ | —CH$_2$O— | 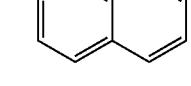 |
| CH$_3$ | H | CH$_3$ | CH$_3$ | —C≡C— | 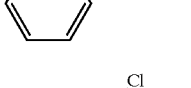 |
| CH$_3$ | H | CH$_3$ | CH$_3$ | —C≡C— | 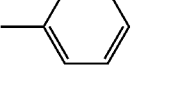 |
| CH$_3$ | H | CH$_3$ | CH$_3$ | —C≡C— | 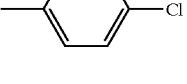 |

TABLE a-continued
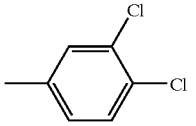
(Ib)
| R¹ | R² | R⁴ | R⁵ | X | R⁶ |
|---|---|---|---|---|---|
| CH₃ | H | CH₃ | CH₃ | —C≡C— | 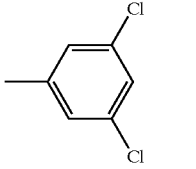 3,4-diCl-phenyl |
| CH₃ | H | CH₃ | CH₃ | —C≡C— | 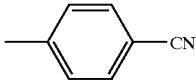 3,5-diCl-phenyl |
| CH₃ | H | CH₃ | CH₃ | —C≡C— | 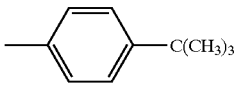 4-CN-phenyl |
| CH₃ | H | CH₃ | CH₃ | —C≡C— | 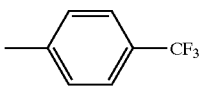 4-C(CH₃)₃-phenyl |
| CH₃ | H | CH₃ | CH₃ | —C≡C— | 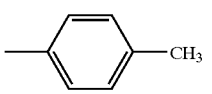 4-CF₃-phenyl |
| CH₃ | H | CH₃ | CH₃ | —C≡C— | 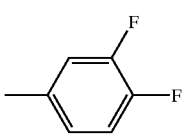 4-CH₃-phenyl |
| CH₃ | H | CH₃ | CH₃ | —C≡C— |  3,4-diF-phenyl |
| CH₃ | H | H | CH₃ | —CH₂— | phenyl |
| CH₃ | H | H | CH₃ | —CH₂— | 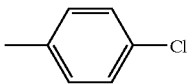 4-Cl-phenyl |

TABLE b
| NC—N=C—N—CH—R⁶ with CH₃ groups (Ib-1) |
|---|
| R⁶ |
| 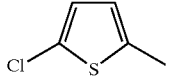 |
| 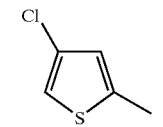 |
| 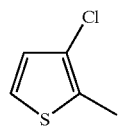 |
| 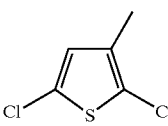 |
| 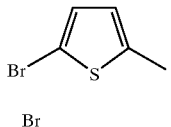 |
| 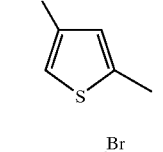 |
| 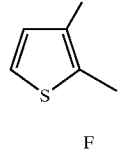 |
| 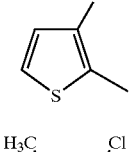 |
| 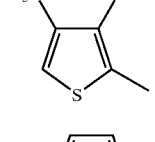 |
| 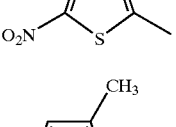 |
| 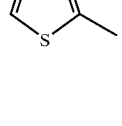 |
TABLE b-continued
| NC—N=C—N—CH—R⁶ with CH₃ groups (Ib-1) |
|---|
| R⁶ |
| 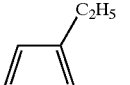 |
| 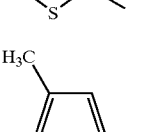 |
| 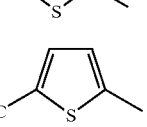 |
| 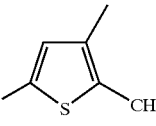 |
| 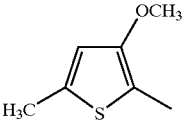 |
| 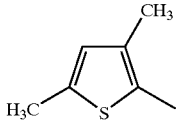 |
| 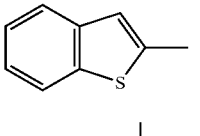 |
| 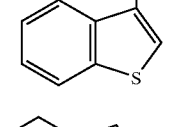 |
| 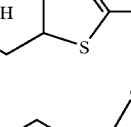 |
| 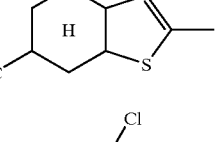 |
| 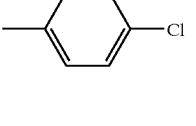 |

TABLE b-continued
$$\text{NC}-\text{N}=\underset{\underset{CH_3}{|}}{\overset{\overset{CH_3}{|}}{C}}-\underset{\underset{H}{|}}{N}-\overset{\overset{CH_3}{|}}{\underset{|}{CH}}-R^6 \quad (Ib-1)$$
R⁶
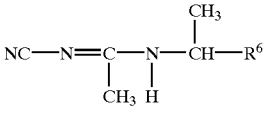
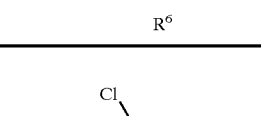
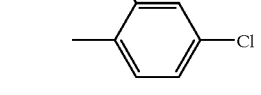
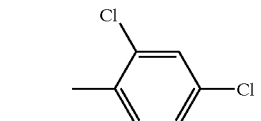
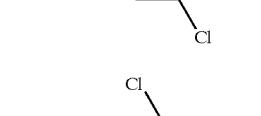
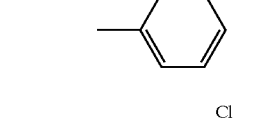
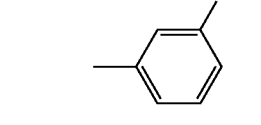
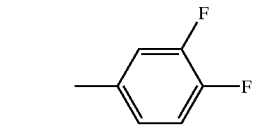
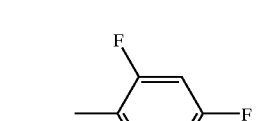
TABLE b-continued
$$\text{NC}-\text{N}=\underset{\underset{CH_3}{|}}{\overset{\overset{CH_3}{|}}{C}}-\underset{\underset{H}{|}}{N}-\overset{\overset{CH_3}{|}}{\underset{|}{CH}}-R^6 \quad (Ib-1)$$
R⁶
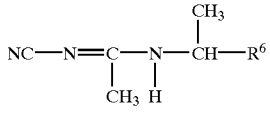
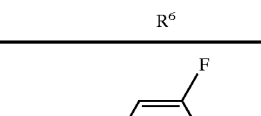
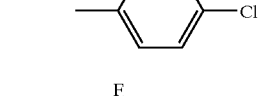
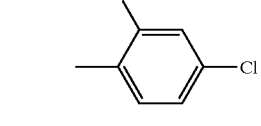
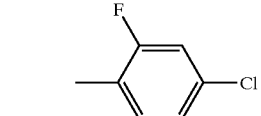
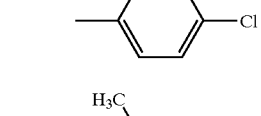
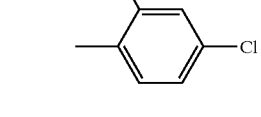
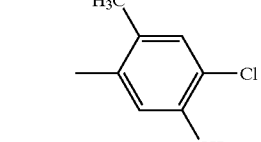

TABLE b-continued
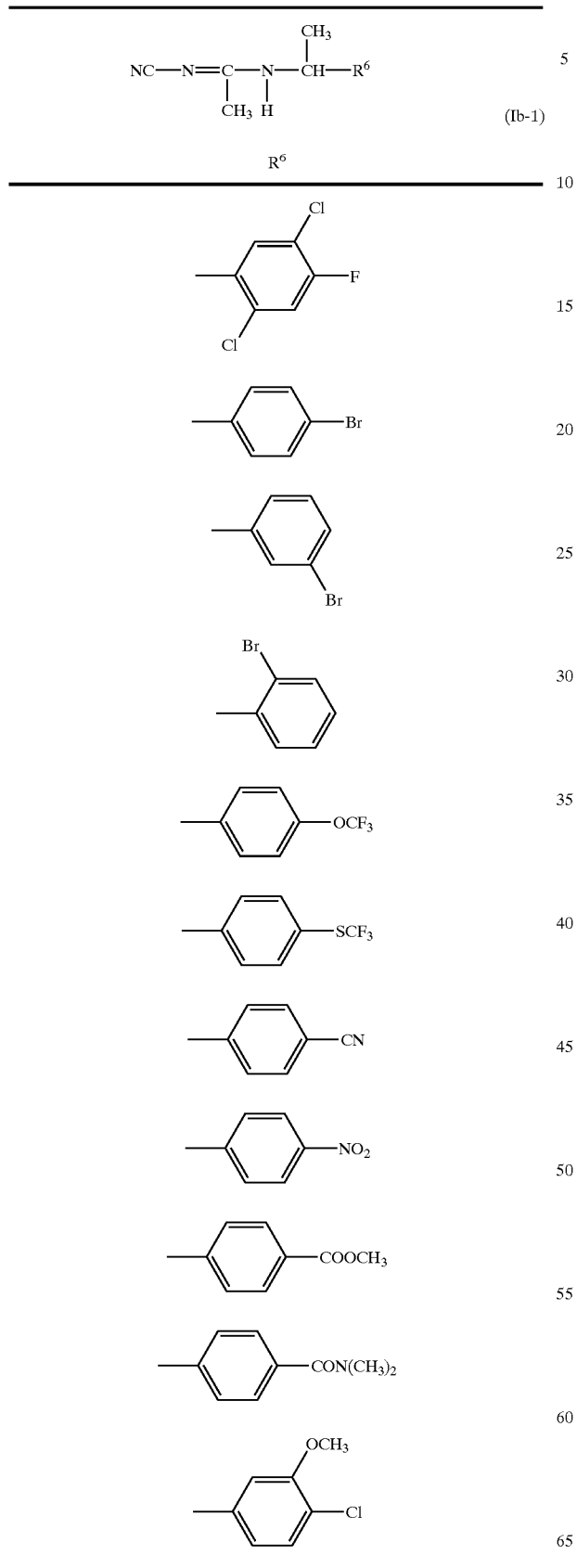
(Ib-1)
TABLE b-continued
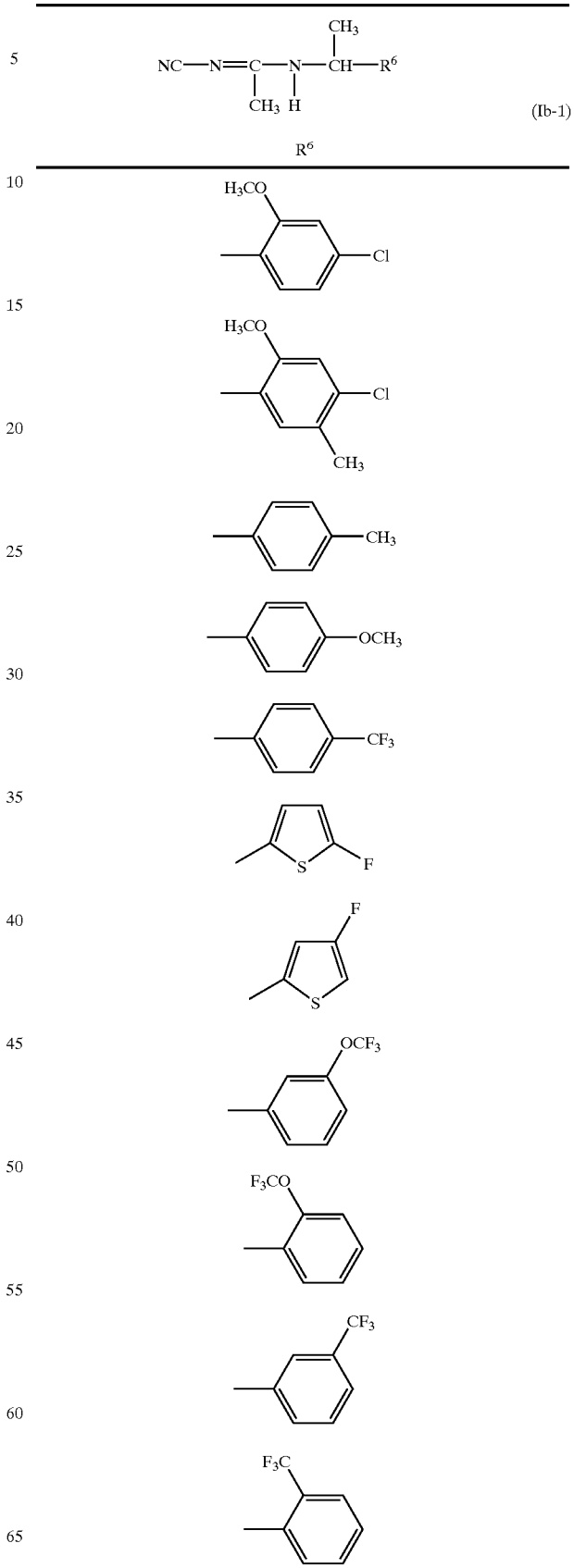
(Ib-1)

TABLE b-continued
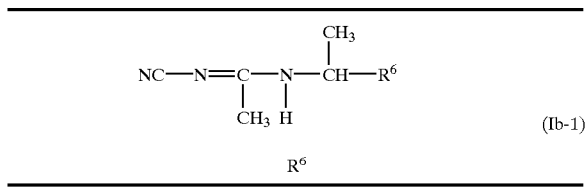
(Ib-1)
R[6]
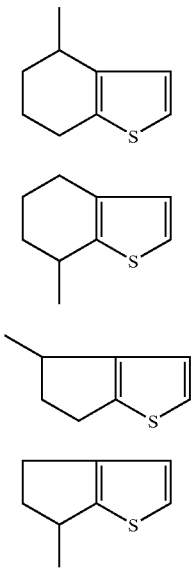
TABLE c
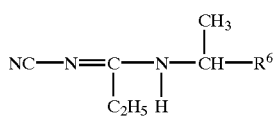
(Ib-2)
R[6]=as listed in Table b, and additionally
R[6]
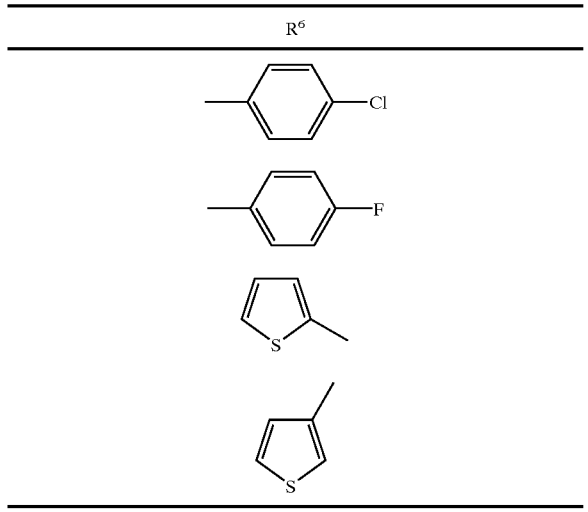
TABLE d
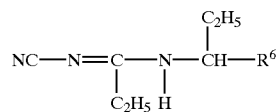
(Ib-3)
R[6]=as listed in Table c.
TABLE e
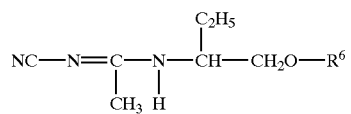
(Ib-4)
R[6]
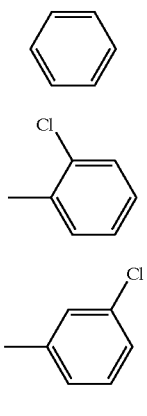

TABLE e-continued (Ib-4)

$$NC-N=C(CH_3)-N(H)-CH(C_2H_5)-CH_2O-R^6$$

| $R^6$ |
|---|
| 3-(i-C₃H₇)-C₆H₄– |
| 3-OCH₃-C₆H₄– |
| 3-F-C₆H₄– |
| 3,4-F₂-C₆H₃– |
| 3-N(CH₃)₂-C₆H₄– |
| 2,4-(CH₃)₂-C₆H₃– |
| 3,4-Cl₂-C₆H₃– |
| 2,4-(CH₃)₂-C₆H₃– |
| 2,4-(CH₃)₂-C₆H₃– |
| 3,5-F₂-C₆H₃– |
| 3-CH₃-4-F-C₆H₃– |
| 2-F-4-CN-C₆H₃– (attached at 4 position via methyl) |
| 2-CN-5-F-C₆H₃– |
| 2-CN-3-F-C₆H₃– |
| 2,3-Cl₂-C₆H₃– |
| 3,5-Cl₂-C₆H₃– |
| 3,5-(OCH₃)₂-C₆H₃– |

TABLE e-continued (Ib-4)

NC—N=C—N—CH(C₂H₅)—CH₂O—R⁶
      |   |
      CH₃ H

R⁶:
- 3,5-dimethylphenyl
- 2-methoxyphenyl
- 2-fluorophenyl
- 4-fluorophenyl
- 4-methoxyphenyl

TABLE f (Ib-5)

NC—N=C—N—CH(CH₃)—CH₂O—R⁶
      |   |
      CH₃ H

R⁶ = as listed in Table e.

TABLE g (Ib-6)

NC—N=C—N—CH₂—R⁶
      |   |
      CH₃ H

R⁶:
- 4-(trifluoromethyl)phenyl

TABLE g-continued (Ib-6)

NC—N=C—N—CH₂—R⁶
      |   |
      CH₃ H

R⁶:
- 3,4,5-trimethoxyphenyl
- 3,4-dimethoxyphenyl
- 2-methoxyphenyl
- 4-fluorophenyl
- 4-chlorophenyl
- 3,4-dichlorophenyl
- 3,4-dichlorophenyl
- 2-chlorophenyl
- 3-methoxyphenyl
- 2,3-dimethylphenyl TABLE g-continued $$\text{NC}-\text{N}=\underset{\underset{H}{|}}{\overset{\overset{CH_3}{|}}{C}}-\text{N}-\text{CH}_2-\text{R}^6 \quad \text{(Ib-6)}$$

R⁶

(structures only; not transcribed)

TABLE g-continued (Ib-6)

NC—N=C—N—CH₂—R⁶
       |   |
      CH₃  H

| R⁶ |
|---|
| 2-nitrophenyl (o-O₂N, methyl) |
| 3-nitrophenyl (methyl, m-NO₂) |
| 4-nitrophenyl (methyl, p-NO₂) |
| 2,6-dichloro-methylphenyl |
| 2,4-dichloro-methylphenyl |
| 2,5-difluoro-methylphenyl |
| 2-trifluoromethyl-methylphenyl |
| 4-amino-2,3-dimethylphenyl |
| 3,5-dimethoxy-2-methyl-4-methoxyphenyl |
| 4-chloro-3-methylphenyl-amino (Cl, NH₂) |
| 2-chloro-6-fluoro-3-methylphenyl |
| 2-chloro-4-(2,2,2-trifluoroethyl)-methylphenyl (CH₂CF₃) |
| 4-(methoxycarbonyl)-methylphenyl (COOCH₃) |
| 4-(N-methylsulfamoyl)-methylphenyl (SO₂NHCH₃) |

TABLE h (Ic)

NC—N=C—N—Y—R⁷
       |  |
       R¹ R²

| R¹  | R² | Y | R⁷ |
|-----|----|----|-----|
| CH₃ | H  | — | 4-chloro-methylphenyl |

The abovementioned compounds according to the invention of the various formulae and in the individual tables can, if appropriate, be present as racemates, R or S isomers. Using, for example, methyl N-cyano-ethaneimidate and 4-chloro-2-methylbenzylamine as starting materials, the course of the process according to the invention can be represented by the following reaction scheme:

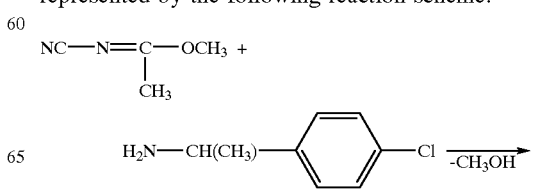

-continued

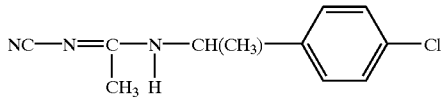

The formula (II) provides a general definition of the ethaneamido esters required as starting materials for carrying out the process according to the invention. In this formula, Z preferably represents $C_1$–$C_4$-alkyl, such as, in particular, methyl or ethyl.

Most of the N-cyano-ethaneamido esters are known (cf., for example, U.S. Pat. No. 5,304,566 or J. Org. Chem. 28, 1963, 1816–1821) and/or they can be obtained by a customary process.

The N-nitro-ethaneamido esters are obtained, for example, by nitrating the corresponding $NO_2$-free ethaneamidoesters of the formula (II) in a customary manner.

The amines of the general formula (III) further to be used as starting materials in the process according to the invention are generally known compounds of organic chemistry, and/or they can be obtained in a generally known manner.

The process according to the invention is preferably carried out in the presence of a diluent. Preference is given to using alcohols, such as methanol and ethanol; nitriles, such as acetonitrile, or esters, such as ethyl acetate. It is also possible, if appropriate, to carry out the process in water or organic-aqueous mixtures.

When carrying out the process according to the invention, the compounds are preferably employed in equimolar amounts; however, it is also possible to employ an excess of one or the other starting material.

When carrying out the process according to the invention, the reaction temperatures can be varied within a relatively wide range. In general, the process is carried out at temperatures between 0° C. and 100° C., preferably between 20° C. and 80° C.

Work-up and isolation of the end products is carried out in a generally known manner.

The active compounds, while being well-tolerated by plants, and having favourable homeotherm toxicity, are suitable for controlling animal pests, in particular insects, arachnids and nematodes, encountered in agriculture, in forests, in the protection of stored products and of materials, and in the hygiene sector. They can preferably be employed as crop protection agents. They are active against normally sensitive and resistant species and against all or some stages of development. The abovementioned pests include:

From the order of Isopoda, for example, *Oniscus asellus, Armadillidium vulgare* and *Porcellio scaber.*

From the order of Diplopoda, for example, *Blaniulus guttulatus.*

From the order of Clilopoda, for example, *Geophilus carpophagus* and Scutigera spp.

From the order of Symphyla, for example, *Scutigerella immiculata.*

From the order of Thysanura, for example, *Lepisma saccharina.*

From the order of Collembola, for example, *Onychitirus armatus.*

From the order of Orthoptera, for example, *Acheta domesticus*, Gryllotalpa spp., *Locusta migratoria migratorioides*, Melanoplus spp. and *Schistocerca gregaria.*

From the order of Blattaria, for example, *Blatta orientalis, Periplaneta americana, Leucophaea maderae* and *Blattella germanica.*

From the order of Dermaptera, for example, *Forficula auricularia.*

From the order of Isoptera, for example, Reticulitermes spp.

From the order of Phthiraptera, for example, *Pediculus humanus corporis*, Haematopinus spp., Linognathus spp., Trichodectes spp. and Damalinia spp.

From the order of Thysanoptera, for example, *Hercinothrips femoralis, Thrips tabaci, Thrips palmi* and *Frankliniella accidentalis.*

From the order of Heteroptera, for example, Eurygaster spp., *Dysdercus intermedius, Piesma quadrata, Cimex lectularius, Rhodnius prolixus* and Triatoma spp.

From the order of Homoptera, for example, *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix*, Pemphigus spp., *Macrosiphum avenae*, Myzus spp., *Phorodon humuli, Rhopalosiphum padi*, Empoasca spp., *Euscelis bilobatus, Nephotettix cincticeps, Lecanium corni, Saissetia oleae, Laodelphax striatellus, Nilaparvata lugens, Aonidiclla aurantii, Aspidiotus hederae*, Pseudococcus spp. and Psylla spp.

From the order of Lepidoptera, for example, *Pectinophora gossypiella, Bupalus piniarius, Cheimatobia brumata, Lithocolletis blancardella, Hyponomeuta padella, Plutella xylustella, Malacosoma neustria, Euproctis chrysorrhoea*, Lymantria spp., *Bucculatrix thurberiella, Phyllocnistis citrella*, Agrotis spp., Euxoa spp., Feltia spp., *Earias insulana*, Heliothis spp., *Mamestra brassicae, Panolis flammea*, Spodoptera spp., *Trichoplusia ni, Carpocapsa pomonella*, Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.*

From the order of Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae*, Diabrotica spp., *Psylliodes chrysocephala, Epilachna varivestis*, Atomaria spp., *Oryzaephilus surinamensis*, Anthonomus spp., Sitophilus spp., *Otiorrhynchus sulcatus, Cosmopolites sordidus, Ceuthorrhynchus assimilis, Hypera postica*, Dermestes spp., Trogoderma spp., Anthrenus spp., Attagenus spp., Lyctus spp., *Meligethes aeneus*, Ptinus spp., *Niptus hololeucus, Gibbium psylloides*, Tribolium spp., *Tenebrio molitor*, Agriotes spp., Conoderus spp., *Melolontha melolontha, Amphimallon solstitialis* and *Costelytra zealandica.*

From the order of Hymenoptera, for example, Diprion spp., Hoplocampa spp., Lasius spp., *Monomorium pharaonis* and Vespa spp.

From the order of Diptera, for example, Aedes spp., Anopheles spp., Culex spp., *Drosophila melanogaster*, Musca spp., Fannia spp., *Calliphora erythrocephala*, Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit.* Phorbia spp., *Pegomyia hyoscyami, Ceratitis capitata, Dacus oleae, Tipula paludosa*, Hylemyia spp. and Liriomyza spp.

From the order of Siphonaptera, for example, *Xenopsylla cheopis* and Ceratophyllus spp.

From the class of the Arachnida, for example, *Scorpio maurus* and *Latrodectus mactans.*

From the order of Acarina, for example, *Acarus siro*, Argas spp., Omrithodoros spp., *Dermanyssus gallinae, Erio-*

*phyes ribis, Phyllocoptruta oleivora*, Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa*, Panonychus spp. and Tetranychus spp.

The phytoparasitic nematodes include, for example, Pratylenchus spp., *Radopholus similtis, Ditylenchus dipsaci, Tylenchulus semipenetrans*, Heterodera spp., Globodera spp., Meloidogyne spp., Aphelenchoides spp., Longidorus spp., Xiphinema spp., Trichodorus spp, and *Bursa phelenchus* spp.

The compounds of the formula (I) according to the invention are distinguished in particular by good nematicidal activity. Thus, they can be employed particularly successfully for controlling, for example, *Meloidogyne incognita*.

The active compounds can be converted into the customary formulations, such as solutions, emulsions, wettable powders, suspensions, powders, dusting agents, pastes, soluble powders, granules, suspo-emulsion concentrates, natural and synthetic materials impregnated with active compound and very fine capsules and polymeric substances.

At the appropriate application rates, Some of the compounds according to the invention have herbicidal activity.

These formulations are prepared in a known manner, for example by mixing the active compounds with extenders, that is liquid solvents and/or solid carriers, if appropriate with the use of surfactants, that is emulsifiers and/or dispersants and/or foam-formers.

If the extender used is water, it is also possible to use, for example, organic solvents as auxiliary solvents. Suitable liquid solvents are essentially: aromatics, such as xylene, toluene, or alkylnaphthalenes, chlorinated aromatics and chlorinated aliphatic hydrocarbons, such as chlorobenzene, chloroethylenes or methylene chloride, aliphatic hydrocarbons, such as cyclohexane, or paraffins, for example mineral oil fractions, mineral or vegetable oils, alcohols, such as butanol or glycol, and also their ethers and esters, ketones, such as acetone, methyl ethyl ketone, methyl isobutyl ketone or cyclohexanone, strongly polar solvents, such as dimethylformamide and dimethyl sulphoxide, and also water.

Suitable solid carriers are:
for example ammonium salts and ground natural minerals, such as kaolins, clays, talc, chalk, quartz, attapulgite, montinorillonite or diatomaceous earth, and ground synthetic minerals, such as finely divided silica, alumina and silicates; suitable solid carriers for granules are: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; suitable emulsifiers and/or foam-formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates: suitable dispersants are: for example linin-sulphite waste liquors and methycellulose.

Tackifiers such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95% by weight of active compound, preferably between 0.5 and 90%.

The active compound according to the invention can be present in its commercially available formulations and in the use forms, prepared from these formulations, as a mixture with other active compounds, such as insecticides, attractants, sterilizing agents, bactericides, acaricides, nematicides, fungicides, growth-regulating substances or herbicides. The insecticides include, for example, phosphates, carbamates, carboxylates, chlorinated hydrocarbons, phenylureas and substances produced by microorganisms, inter alia.

Examples of particularly advantageous mixing components are the following:

Fungicides:
  aldimorph, ampropylfos, ampropylfos potassium, andoprim, anilazine, azaconazole, azoxystrobin,
  benalaxyl, benodanil, benomyl, benzamacril, benzamacril-isobutyl, bialaphos, binapacryl, biphenyl, bitertanol, blasticidin-S, bromuconazole, bupirimate,
  calcium polysulphide, capsimycin, captafol, captan, carbendazim, carboxin, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram,
  debacarb, dichlorophen, diclobutrazole, diclofluanid, diclomezine, dicloran, diethofencarb, difenoconazole, dimethirimol, dimethomorph, diniconazole, diniconazole-M, dinocap, diphenylamine, dipyrithione, ditalimfos, dithianon, dodemorph, dodine, drazoxolon,
  edifenphos, epoxiconazole, etaconazole, ethirimol, etridiazole,
  famoxadon, fenapanil, fenarimol, fenbuconazole, fenfuram, fenitropan, fenpiclonil, fenpropidin, fenpropimorph, fentin acetate, fentin hydroxide, ferbam, ferimzone, fluazinam, flumetover, fluoromide, fluquinconazole, flurprimidol, flusilazole, flusulfamide, flutolanil, flutriafol, folpet, fosetyl-aluminium, fosetyl-sodium, fthalide, fuberidazole, furalaxyl, furametpyr, furcarbonil, furconazole, furconazole-cis, furmecyclox, guazatine,
  hexachlorobenzene, hexaconazole, hymexazole,
  imazalil, imibenconazole, iminoctadine, iminoctadine albesilate, iminoctadine triacetate, iodocarb, ipconazole, iprobenfos (IBP), iprodione, irumamycin, isoprothiolane, isovaledione,
  kasugamycin, kresoxim-methyl, copper preparations, such as: copper hydroxide, copper naphthenate, copper oxychloride, copper sulphate, copper oxide, oxine-copper and Bordeaux mixture,
  mancopper, mancozeb, maneb, meferimzone, mepanipyrim, mepronil, metalaxyl, metconazole, methasulfocarb, methfuroxam, metiram, metomeclam, metsulfovax, mildiomycin, myclobutanil, myclozolin,
  nickel dimethyldithiocarbamate, nitrothal-isopropyl, nuarimol,
  ofurace, oxadixyl, oxamocarb, oxolinic acid, oxycarboxim, oxyfenthiin, paclobutrazole, pefurazoate, penconazole, pencycuron, phosdiphen, pimaricin, piperalin, polyoxin, polyoxorim, probenazole, prochloraz, procymidone, propamocarb, propanosine-sodium, propiconazole, propineb, pyrazophos, pyrifenox, pyrimethanil, pyroquilon, pyroxyfur, quinconazole, quintozene (PCNB), sulphur and sulphur preparations, tebuconazole, tecloftalam, tecnazene, tetcyclacis, tetraconazole, thiabendazole, thicyofen, thifluzamide, thiophanate-methyl, thiram, tioxymid, tolclofos-methyl, tolylfluanid, triadimefon, triadimenol, triazbutil, triazoxide, trichiamide, tricyclazole, tridemorph, triflumizole, triforine, triticonazole, uniconazole, validamycin A, vinclozolin, viniconazole, zarilamide, zineb, ziram and also Dagger G,

OK-8705,

OK-8801,

α-(1,1-dimethylethyl)-β-(2-phenoxyethyl)-1H-1,2,4-triazole-1-ethanol,

α-(2,4-dichlorophenyl)-β-fluoro-β-propyl-1H-1,2,4-triazole-1-ethanol,

α-(2,4-dichlorophenyyl)-β-methoxy-α-methyl-1H-1,2,4-triazole-1-ethanol,

α-(5-methyl-1,3-dioxan-5-yl)-β-[[4-(trifluoromethyl)-phenyl]-methylene]-1H-1,2,4-triazole-1-ethanol, (5RS,6RS)-6-hydroxy-2,2,7,7-tetramethyl-5-(1H-1,2,4-triazol-1-yl)-3-octanone, (E)-α-(methoxylmino)-N-methyl-2-phenoxy-phenylacetamide, isopropyl{2-methyl-1-[[[1-(4-methylphenyl)-ethyl]-amino]-carbonyl]-propyl}-carbamate, 1-(2,4-dichlorophenyl)-2-(1H-1,2,4-triazol-1-yl)-ethanone O-(phenylmethyl)-oxime, 1-(2-methyl-1-naphthalenyl)-1H-pyrrol-2,5-dione, 1-(3,5-dichlorophenyl)-3-(2-propenyl)-2,5-pyrrolidinedione, 1-[(diiodomethyl)-sulphonyl]-4-methyl-benzene, 1-[[2-(2,4-dichlorophenyl)-1,3-dioxolan-2-yl]-methyl]-1H-imidazole, 1-[[2-(4-chlorophenyl)-3-phenyloxiranyl]-methyl]-1H-1,2,4-triazole, 1-[1-[2-[(2,4-dichlorophenyl)-methoxy]-phenyl]-ethenyl]-1H-imidazole, 1-methyl-5-nonyl-2-(phenylmethyl)-3-pyrrolidinole, 2',6'-dibromo-2-methyl-4'-trifluoromethoxy-4'-trifluoro-methyl-1,3-thiazole-5-carboxanilide, 2,2-dichloro-N-[1-(4-chlorophenyl)-ethyl]-1-ethyl-3-methyl-cyclopropane-carboxamide.

2,6-dichloro-5-(methylthio)-4-pyrinidinyl-thiocyanate, 2,6-dichloro-N(4-trifluoromethylbenzyl)-benzamide, 2,6-dichloro-N-[[4-(trifluoromethyl)-phenyl]-methyl]-benzamide, 2-(2,3,3-triiodo-2-propenyl)-2H-tetrazole, 2-[(1-methylethyl)sulphonyl]-5-(trichloromethyl)-1,3,4-thiadiazole, 2-[[6-deoxy-4-O-(4-O-methyl-β-D-glycopyranosyl)-a-D-glycopyranosyl]-amino]-4-methoxy-1H-pyrrolo[2,3-d]pyrimidine-5-carbonitrile, 2-aminobutane, 2-bromo-2-(bromomethyl)-pentanedinitrile, 2-chloro-N-(2,3-dihydro-1,3-trimethyl-1H-inden-4-yl)-3-pyridinecarboxamide, 2-chloro-N-(2,6-dimethylphenyl)-N-(isothiocyanatomethyl)-acetamide, 2-phenylphenol (OPP), 3,4-dichloro-1-[4-(difluoromethoxy)-phenyl]-1H-pyrrol-2,5-dione, 3,5-dichloro-N-[cyano-[(1-methyl-2-propynyl)-oxy]-methyl]-benzamide, 3-(1,1-dimethylpropyl-1-oxo-1H-indene-2-carbonitrile, 3-[2-(4-chlorophenyl)-5-ethoxy-3-isoxazolidinyl]-pyridine, 4-chloro-2-cyano-N,N-dimethyl-5-(4-methylphenyl)-1H-imidazole-1-sulphonamide, 4-methyl-tetrazolo[1,5-a]quinazolin-5(4H)-one, 8-(1,1-dimethylethyl)-N-ethyl-N-propyl-1,4-dioxaspiro[4,5]decane-2-methanamine, 8-hydroxyquinoline sulphate, 9H-xanthene-2-[(phenylamino)-carbonyl]-9-carboxylic hydrazide, bis-(1-methylethyl)-3-methyl-4-[(3-methylbenzoyloxy]-2,5-thiophenedicarboxylate, cis-1-(4-chlorophenyl)-2-(1H-1,2,4-triazol-1-yl)-cycloheptanol, cis-4-[3-[4-(1,1-dimethylpropyl)-phenyl-2-methylpropyl]-2,6-dimethyl-morpholinehydrochloride, ethyl[(4-chlorophenyl)-azo]-cyanoacetate, potassium hydrogen carbonate, methanetetrathiol sodium salt, methyl 1-(2,3-dihydro-2,2-dimethyl-1H-inden-1-yl)-1H-imidazole-5-carboxylate, methyl N-(2,6-dimethylphenyl)-N-(5-isoxazolylcarbonyl)-DL-alaninate, methyl N-(chloroacetyl)-N-(2,6-dimethylphenyl)-DL-alaninate, N-(2,3-dichloro-4-hydroxyphenyl)-1-methyl-cyclohexanecarboxamide, N-(2,6-dimethylphenyl)-2-methoxy-N-(tetrahydro-2-oxo-3-furanyl)-acetamide, N-(2,6-dinmethylphenyl)-2-methoxy-N-(tetrahydro-2-oxo-3-thienyl)-acetamide, N-(2-chloro-4-nitrophenyl)-4-methyl-3-nitro-benzenesulphonamide, N-(4-cyclohexylphenyl)-1,4,5,6-tetrahydro-2-pyrimidineamine, N-(4-hexylphenyl)-1,4,5,6-tetrahydro-2-pyrimidineamine, N-(5-chloro-2-methylphenyl)-2-methoxy-N-(2-oxo-3-oxazolidinyl)-acetamide, N-(6-methoxy-3-pyridinyl)-cyclopropanecarboxamide, N-[2,2,2-trichloro-1-[(chloroacetyl)-amino]-ethyl]-benzamide, N-[3-chloro-4,5-bis(2-propinyloxy)-phenyl]-N'-methoxy-methanimidamide, N-formyl-N-hydroxy-DL-alanine-sodium salt, O,O-diethyl[2-(dipropylamino)-2-oxoethyl]-ethylphosphoramidothioate, O-methyl S-phenyl phenylpropylphosphoramidothioate, S-methyl 1,2,3-benzothiadiazole-7-carbothioate,
spiro[2H]-1-benzopyrane-2,1'(3'H)-isobenzofuran]-3'-one, Bactericides:
bronopol, dichlorophen, nitrapyrin, nickel dimethyidithiocarbamate, kasugamycin, octhilinone, furancarboxylic acid, oxytetracyclin, probenazole, streptomycin, tecloftalam, copper sulphate and other copper preparations.

Insecticides/Acaricides/Nematicides:
abamectin, AC303 630, acephate, acrinathrin, alanycarb, aldicarb, alphamethrin, amitraz, avermectin, AZ 60541, azadirachtin, azinphos A, azinphos M, azocyclotin,

*Bacillus thuringiensis*, bendiocarb, benfuracarb, bensultap, betacyfluthrin, bifenthrin, BPMC, brofenprox, bromophos A, bufencarb, buprofezin, butocarboxim, butylpyridaben, cadusafos, carbaryl, carbofuran, carbophenothion, carbosulfan, cartap, CGA 157 419, CGA 184699, chloethocarb, chlorethoxyfos, chlorfenvinphos, chlortluazuron, chlormephos, chlorpyrifos, chlorpyrifos M, cis-resmethrin, clocythrin, clofentezine, cyanophos, cycloprothrin, cyfluthrin, cyhalothrin, cyhexatin, cypermethrin, cyromazine, deltamethrin, demeton M, demeton S, demeton S-methyl, diafenthiuron, diazinon, dichlofenthion, dichlorvos, dicliphos, dicrotophos, diethion, diflubenzuron, dimethoate, dimethylvinphos, dioxathion, disulfoton, edifenphos, emamectin, esfenvalerate, ethiofencarb, ethion, ethofenprox, ethoprophos, etrimphos, fenamiphos, fenazaquin, fenbutatin oxide, fenitrothion, fenobucarb, fenothiocarb, fenoxycarb, fenpiopathrin, fenpyrad, fenpyroximate, fenthion, fenvalerate, fipronil, fluazinam, flucycloxuron, flucythrinate, flufenoxuron, flufenprox, fluvalinate, fonophos, formothion, fosthiazate, fubfenprox, furathiocarb, HCH, heptenophos, hexaflumuron, hexythiazox, imidacloprid, iprobenfos, isazophos, isofenphos, isoprocarb, isoxathion, ivermectin, lambda-cyhalothrin, lufenuron, malathion, inecarbam, mevinphos, mesulfenphos, metaldehyde, methacrifos, methamidophos, methidathion, methiocarb, methomyl, metolcarb, milbemectin, monocrotophos, moxidectin, naled, NC 184, NI 25, nitenpyram, omethoate, oxamyl, oxydemethon M, oxydeprofos, parathion A, parathion M, permethrin, phenthoate, phorate, phosalone, phosmet, phosphamidon, phoxim, pirimicarb, pirimiphos M, pirimiphos A, profenofos, promecarb, propaphos, propoxur, prothiofos, prothoate, pymetrozin, pyrachlophos, pyridaphenthion, pyresmethrin, pyrethrum, pyridaben, pyrimidifen, pyriproxifen, quinalphos,

RH 5992 salithion, sebufos, silafluofen, sulfotep, suiprofos, spinosad, tebufenozide, tebufenpyrad, tebupirimiphos, teflubenzuron, tefluthrin, temephos, terbam, terbufos, tetrachlorvinphos, thiafenox, thiodicarb, thiofanox, thiomethon, thionazin, thuringiensin, tralomethrin, triarathen, triazophos, triazuron, trichlorfon, triflumuron, trimethacarb, thiamethoxam.

vamidothion, XMC, xylycarb, YI 5301/5302, zetamethirin.

It is also possible to admix other known active compounds, such as herbicides, fertilizers and growth-regulating substances.

When used as insecticides and nematicides, the active compounds according to the invention can furthermore be present in their commercial formulations and in the use forms prepared from these formulations, as a mixture with synergists. Synergists are compounds which increase the activity of the active compounds, without it being necessary for the added synergist to be active itself.

The active compound content of the use forms prepared from the commercial formulations can vary within wide ranges. The active compound concentration of the use form can be from 0.0000001 to 95% by weight of active compound, and is preferably between 0.00001 and 1% by weight.

The application is carried out in a manner which is adapted to the use forms.

When used against hygiene pests and pests of stored products, the active compound is distinguished by excellent residual activity on wood and clay, and by good stability to alkali on limed substrates.

At the appropriate application rates, the compounds according to the invention also have herbicidal properties and/or growth-regulating activity, such as, for example, a defoliant effect.

The active compounds according to the invention act not only against plant, hygiene and stored product pests, but also in the veterinary medicine sector against animal parasites (ectoparasites), such as hard ticks, soft ticks, mange mites, leaf mites, flies (biting and licking), parasitic fly larvae, lice, hair lice, feather lice and fleas. These parasites include:

From the order of the Anoplurida, for example, Haematopinus spp., Linognathus spp., Pediculus spp., Phtirus spp. and Solenopotes spp.

From the order of the Mallophagida and the suborders Amblycerina and Ischnocerina, for example, Trimenopon spp., Menopon spp., Trinoton spp., Bovicola spp., Werneckiella spp., Lepikentron spp., Damalina spp., Trichodectes spp. and Felicola spp.

From the order of the Diptera and the suborders Nematocerina and Brachycerina, for example, Aedes spp., Anopheles spp., Cuiex spp., Simulium spp., Eusimulium spp., Phlebotomus spp., Lutzomyia spp., Culicoides spp., Chrysops spp., Hybomitra spp., Atylotus spp., Tabanus spp., Haematopota spp., Philipomyia spp., Braula spp., Musca spp., Hydrotaca spp., Stomoxys spp., Haematobia spp., Morellia spp., Fannia spp., Glossina spp., Calliphora spp., Lucilia spp., Chrysomyia spp., Wohifahrtia spp., Sarcophaga spp., Oestrus spp., Hypoderma spp., Gasterophilus spp., Hippobosca spp., Lipoptena spp. and Melophagus spp.

From the order of the Siphonapterida, for example Pulex spp., Ctenocephalides spp., Xenopsylla spp. and Ceratophyllus spp.

From the order of the Heteropterida, for example, Cimex spp., Triatoma spp., Rhodnius spp. and Panstrongylus spp.

From the order of the Blattarida, for example *Blatta orientalis, Periplaneta americana, Blattela germanica* and Supella spp.

From the subclass of the Acaria (Acarida) and the orders of the Meta- and Mesostigmata, for example, Argas spp., Ornithodorus spp., Otobius spp., Ixodes spp., Amblyomma spp., Boophilus spp., Dermacentor spp., Haemophysalis spp., Hyalomma spp., Rhipicephalus spp., Dermanyssus spp., Raillietia spp., Pneumonyssus spp., Sternostoma spp. and Varroa spp.

From the order of the Actinedida (Prostigmata) und Acaridida (Astigmata), for example, Acarapis spp., Cheyletiella spp., Ornithocheyletia spp., Myobia spp., Psorergates spp., Demodex spp., Trombicula spp., Listrophorus spp., Acarus spp., Tyophagus spp., Caloglyphus spp., Hypodectes spp., Perolichus spp., Psoroptes spp., Chorioptes spp., Otodectes spp., Sarcoptes spp., Notoedres spp., Knemioidcoptes spp., Cytodites spp. and Laminosioptes spp.

The active compounds of the formula (I) according to the invention are also suitable for controlling arthropods which infest agricultural productive livestock, such as, for example, cattle, sheep, goats, horses, pigs, donkeys, camels, buffalo, rabbits, chickens, turkeys, ducks, geese and bees, other pets, such as, for example, dogs, cats, caged birds and aquarium fish, and also so-called test animals, such as, for example, hamsters, guinea pigs, rats and mice. By controlling, these arthropods, cases of death and reduction in productivity (for meat, milk, wool, hides, eggs, honey etc.) should be diminished, so that more economic and easier animal husbandry is possible by use of the active compounds according to the invention.

The active compounds according to the invention are used in the veterinary sector in a known manner by enteral administration in the form of, for example, tablets, capsules, potions, drenches, granules, pastes, boluses, the feed-through process and suppositories, by parenteral administration, such as, for example, by injection (intramuscular, subcutaneous, intravenous, intraperitoneal and the like), implants by nasal administration, by dermal use in the form, for example, of dipping or bathing, spraying, pouring on and spotting on, washing and powdering, and also with the aid of molded articles containing the active compound, such as collars, ear marks, tail marks, limb bands, halters, marking devices and the like.

When used for cattle, poultry, pets and the like, the active compounds of the formula (I) can be used as formulations (for example powders, emulsions, free-flowing compositions), which comprise the active compounds in an amount of 1to 80% by weight, directly or after 100 to 10,000-fold dilution, or they can be used as a chemical bath.

It has furthermore been found that the compounds of the formula (I) according to the invention also have a strong insecticidal action against insects which destroy industrial materials.

The following insects may be mentioned as examples and as preferred—but without a limitation:

Beetles, such as
  *Hylotrupes bajulus, Chlorophorus pilosis, Anobium punctatum, Xestobium rufovillosum, Ptilinus pecticomis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis,* Xyleborus spec., Tryptodendron spec., *Apate monachus, Bostrychus capucins, Heterobostrychus brunneus,* Sinoxylon spec., *Dinoderus minutus.*

Hymenopterons, such as
  *Sirex juvencus, Urocerus gigas, Urocerus gigas taignus, Urocerus augur*

Termites, such as
  *Kalotermes flavicollis, Cryptotermes brevis, Heterotermes indicola, Reticulitermes flavipcs, Reticulitermes santonensis, Reticulitermes lucifugus, Mastotermes darwiniensis, Zootermopsis nevadensis, Coptotermes formosanus.*

Bristletails, such as
  *Lepisma saccarina.*

Industrial materials in the present connection are to be understood as meaning non-living materials, such as, preferably, plastics, adhesives, sizes, papers and cards, leather, wood and processed wood products and coating compositions.

Wood and processed wood products are materials to be protected, especially preferably, from insect infestation.

Wood and processed wood products which can be protected by the agents according to the invention or mixtures comprising these are to be understood as meaning, for example: building timber, wooden beams, railway sleepers, bridge components, boat jetties, wooden vehicles, boxes, pallets, containers, telegraph poles, wood panelling, wooden windows and doors, plywood, chipboard, joinery or wooden products which are used quite generally in house-building or in building joinery.

The active compounds can be used as such, in the form of concentrates or in generally customary formulations, such as powders, granules, solutions, suspensions, emulsions or pastes.

The formulations mentioned can be prepared in a manner known per se, for example by mixing the active compounds with at least one solvent or diluent, emulsifier, dispersing agent and/or binder or fixing agent, a water repellent, if appropriate siccatives and UV stabilizers and if appropriate dyestuffs and pigments, and also other processing auxiliaries.

The insecticidal compositions or concentrates used for the preservation of wood and tlimiber products comprise the active compound according to the invention in a concentration of 0.0001 to 95% by weight, in particular 0.001 to 60% by weight.

The amount of the compositions or concentrates employed depends on the nature and occurrence of the insects and on the medium. The optimum amount employed can be determined for the use in each case by a series of tests. In general, however, it is sufficient to, employ 0.0001 to 20% by weight, preferably 0.001 to 10% by weight, of the active compound, based on the material to be preserved.

Solvents and/or diluents which are used are an organic chemical solvent or solvent mixture and/or an oily or oil-like organic chemical solvent or solvent mixture of low volatility and/or a polar organic chemical solvent or solvent mixture and/or water, and if appropriate an emulsifier and/or wetting agent.

Organic chemical solvents which are preferably used are oily or oil-like solvents having an evaporation number above 35 and a flash point above 30° C., preferably above 45° C. Substances which are used as such oily or oil-like water-insoluble solvents of low volatility are appropriate mineral oils or aromatic fractions thereof, or solvent mixtures containing mineral oils, preferably white spirit, petroleum and/or alkylbenzene.

Mineral oils having a boiling range from 170 to 220° C., white spirit having a boiling range from 170 to 220° C., spindle oil having a boiling range from 250 to 350° C., petroleum and aromatics having a boiling range from 160 to 280° C., terpentine oil and the like, are advantageously employed.

In a preferred embodiment, liquid aliphatic hydrocarbons having a boiling range from 180 to 210° C. or high-boiling mixtures of aromatic and aliphatic hydrocarbons having a boiling range from 180 to 220° C. and/or spindle oil and/or monochloronaphthalene, preferably α-monochloronaphthalene, are used.

The organic oily or oil-like solvents of low volatility which have an evaporation number above 35 and a flash point above 30° C., preferably above 45° C., can be replaced in part by organic chemical solvents of high or medium volatility, providing that the solvent mixture likewise has an evaporation number above 35 and a flash point above 30° C., preferably above 45° C., and that the insecticide/fungicide mixture is soluble or emulsifiable in this solvent mixture.

According to a preferred embodiment, some of the organic chemical solvent or solvent mixture is replaced by an aliphatic polar organic chemical solvent or solvent mixture. Aliphatic organic chemical solvents containing hydroxyl and/or ester and/or ether groups, such as, for example, glycol ethers, esters or the like, are preferably used.

Organic chemical binders which are used in the context of the present invention are the synthetic resins and/or binding drying oils which are known per se, are water-dilutable and/or are soluble or dispersible or emulsifiable in the organic chemical solvents employed, in particular binders consisting of or comprising an acrylate resin, a vinyl resin, for example polyvinyl acetate, polyester resin, polycondensation or polyaddition resin, polyurethane resin, alkyd resin or modified alkyd resin, phenolic resin, hydrocarbon resin, such as indene-cumarone resin, silicone resin, drying coetable oils and/or drying oils and/or physically drying binders based on a natural and/or synthetic resin.

The synthetic resin used as the binder can be employed in the form of an emulsion, dispersion or solution. Bitumen or bituminous substances can also be used as binders in an amount of up to 10% by weight. Dyestuffs, pigments, water-repelling agents, odour correctants and inhibitors or anticorrosive agents and the like which are known per se can additionally be employed.

It is preferred according to the invention for the composition or concentrate to comprise, as the organic chemical binder, at least one alkyd resin or modified alkyd resin and/or one drying vegetable oil. Alkyd resins having an oil content of more than 45% by weight, preferably 50 to 68% by weight, are preferably used according to the invention.

All or some of the binder mentioned can be replaced by a fixing agent (mixture) or a plasticizer (mixture). These additives are intended to prevent evaporation of the active compounds and crystallization or precipitation. They preferably replace 0.01 to 30% of the binder (based on 100% of the binder employed).

The plasticizers originate from the chemical classes of phthalic acid esters, such as dibutyl, dioctyl or benzyl butyl phthalate, phosphoric acid esters, such as tributyl phosphate, adipic acid esters, such as di-(2-ethylhexyl) adipate, stearates, such as butyl stearate or amyl stearate, oleates, such as butyl oleate, glycerol ethers or higher molecular weight glycol ethers, glycerol esters and p-toluenesulphonic acid esters.

Fixing agents are based chemically on polyvinyl alkyl ethers, such as, for example, polyvinyl methyl ether or ketones, such as benzophenone or ethylenebenzophenone.

Possible solvents or diluents are, in particular, also water, if appropriate as a mixture with one or more, of the above-mentioned organic chemical solvents or diluents, emulsifiers and dispersing agents.

Pairticularly effective preservation of wood is achieved by impregnation processes on a large industrial scale, for example vacuum, double vacuum or pressure processes.

The ready-to-use compositions can also comprise other insecticides, if appropriate, and also one or more fungicides, if appropriate.

Possible additional mixing components are, preferably, the insecticides and fungicides mentioned in WO 94/29 268. The compounds mentioned in this document are an explicit constituent of the present application.

Especially preferred mixing partners which may be mentioned are insecticides, such as chlorpyriphos, phoxim, silafluofin, alphamethrin, cyiluthrin, cypermethrin, deltamethrin, permethrin, imidacloprid, NI-25, flufenoxuron, hexaflumuron and triflumuron, and also fungicides, such as epoxyconazole, hexaconazole, azaconazole, propiconazole, tebuconazole, cyproconazole, metconazole, imazalil, dichlorfluanid, tolylfluanid, 3-iodo-2-propinyl-butyl carbamate, N-octyl-isothiazolin-3-one and 4,5-dichloro-N-octylisothiazolin-3-one.

The preparation and the use of the active compounds according to the invention are illustrated by the examples below.

PREPARATION EXAMPLES

Example 1

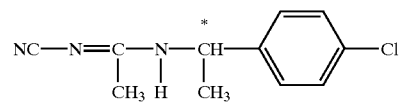

5.0 g (0.05 mol) of methyl N-cyano-ethaneimidate are added to 7.8 g (0.05 mol) of [R]-4-chloro-2-methylbenzylamine in 30 ml of methanol, and the reaction mixture is stirred at room temperature for 2 hours. The mixture is subsequently mixed with water and the precipitate is filtered off and dried.

This gives 7.0 g (63% of theory) of [R]-N-cyano-N'-(4-chlorophenyl-eth-1-yl)-ethaneimidamide of melting point of 125° C. and with an optical rotation $[\alpha]_D^{20}$=+252.5° ($CH_3OH$).

Analogously, and/or in accordance with the general process procedures, the following compounds according to the invention are obtained:

TABLE A

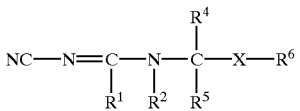
(Ib)

| Ex. No. | R¹ | R² | R⁴ | R⁵ | X | R⁶ | Physical const. |
|---|---|---|---|---|---|---|---|
| 2 | H | H | CH₃ | H | — | 5-methyl-1,3-benzodioxole | viscous |
| 3 | CH₃ | H | C₂H₅ | H | — | 4-methoxyphenyl | m.p. 134° C. |
| 4 | CH₃ | H | H | CH₃ | —CH₂CH₂— | 3-thienyl | m.p. 72° C. |
| 5 | CH₃ | H | H | C₂H₅ | —CH₂CH₂— | 3-thienyl | viscous |
| 6 | CH₃ | H | H | CH₃ | —CH₂CH₂— | 2-thienyl | m.p. 92° C. |
| 7 | CH₃ | H | H | C₂H₅ | —CH₂CH₂— | phenyl | m.p. 90° C. |
| 8 | CH₃ | H | H | CH₃ | —CH₂CH₂— | 4-(SCH₃)phenyl | m.p. 154° C. |
| 9 | CH₃ | H | H | CH₃ | —CH₂CH₂— | 4-(SOCH₃)phenyl | oil |
| 10 | CH₃ | H | H | CH₃ | —CH₂CH₂— | 4-(SO₂CH₃)phenyl | m.p. 74° C. |
| 11 | CH₃ | H | H | n-C₃H₇ | —CH₂CH₂— | 4-chlorophenyl | $n^{20}_D = 1.5476$ |
| 12 | CH₃ | H | H | i-C₃H₇ | —CH₂CH₂— | 4-chlorophenyl | m.p. 142° C. |
| 13 | CH₃ | H | H | C₂H₅ | —CH₂CH₂— | 3-bromo-2-methylthienyl | $n^{20}_D = 1.5760$ |

TABLE A-continued (Ib)

| Ex. No. | R¹ | R² | R⁴ | R⁵ | X | R⁶ | Physical const. |
|---|---|---|---|---|---|---|---|
| 14 | $CH_3$ | H | H | $CH_3$ | —$CH_2CH_2$— |  | m.p. 124° C. (R isomer) |
| 15 | $CH_3$ | H | H | $CH_3$ | —$CH_2CH_2$— | 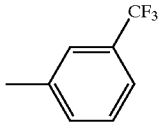 | m.p. 121° C. (S isomer) |
| 16 | $CH_3$ | H | H | $C_2H_5$ | —$CH_2CH_2$— |  | viscous |
| 17 | $CH_3$ | H | H | $CH_3$ | — |  | m.p. 137° C. (S isomer) |
| 18 | $CH_3$ | H | H | $CH_3$ | —$CH_2CH_2$— |  | m.p. 112° C. (R isomer) |
| 19 | $CH_3$ | H | H | $CH_3$ | —$CH_2CH_2$— |  | m.p. 140° C. (S isomer) |
| 20 | $CH_3$ | H | H | $C_2H_5$ | —$CH_2CH_2$— | 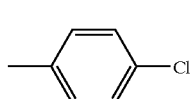 | m.p. 127° C. |
| 21 | $CH_3$ | H | H | $C_2H_5$ | —$CH_2CH_2$— | 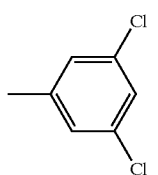 | viscous |
| 22 | $CH_3$ | H | $CH_3$ | $CH_3$ | — |  | m.p. 135° C. |
| 23 | $CH_3$ | H | H | $CH_3$ | — |  | m.p. 135° C. |
| 24 | $CH_3$ | H | H | $C_2H_5$ | — |  | m.p. 108° C. (S isomer) |
| 25 | $CH_3$ | H | H | $C_2H_5$ | — |  | m.p. 117° C. (R isomer) |

TABLE A-continued
(Ib)
NC—N=C(R¹)—N(R²)—C(R⁴)(R⁵)—X—R⁶
| Ex. No. | R¹ | R² | R⁴ | R⁵ | X | R⁶ | Physical const. |
|---|---|---|---|---|---|---|---|
| 26 | CH₃ | H | H | i-C₃H₇ | — |  | $n^{20}_D$ = 1.5517 |
| 27 | CH₃ | H | H | n-C₃H₇ | — |  | $n^{20}_D$ = 1.5522 |
| 28 | CH₃ | H | H | CH₃ | — | 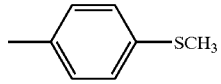 | m.p. 90° C. |
| 29 | CH₃ | H | H | CH₃ | — | 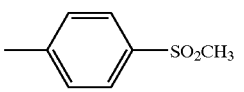 | m.p. 130° C. |
| 30 | CH₃ | H | H | CH₃ | — | 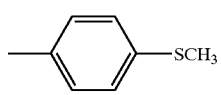 | m.p. 103° C. (S isomer) |
| 31 | CH₃ | H | H | CH₃ | — | 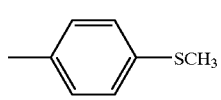 | m.p. 130° C. (R isomer) |
| 32 | CH₃ | H | H | CH₃ | — | 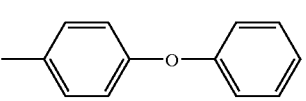 | $n^{20}_D$ = 1.5861 |
| 33 | CH₃ | H | H | CH₃ | — |  | viscous |
| 34 | CH₃ | H | H | CH₃ | — |  | oil |
| 35 | CH₃ | H | H | CH₃ | — | 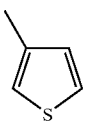 | $n^{20}_D$ = 1.5572 |
| 36 | CH₃ | H | H | CH₃ | — | 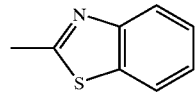 | m.p. 131° C. |
| 37 | CH₃ | H | H | C₂H₅ | — | 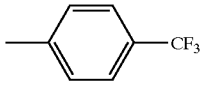 | viscous |
| 38 | CH₃ | H | H | CH₃ | — |  | m.p. 68° C. |

TABLE A-continued (Ib)
$$NC-N=C(R^1)-N(R^2)-C(R^4)(R^5)-X-R^6$$

| Ex. No. | R¹ | R² | R⁴ | R⁵ | X | R⁶ | Physical const. |
|---|---|---|---|---|---|---|---|
| 39 | CH₃ | H | H | C₂H₅ | — | 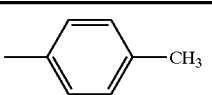 4-CH₃-C₆H₄ | viscous |
| 40 | CH₃ | H | H | CH₃ | — | 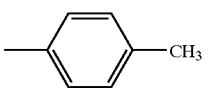 4-CH₃-C₆H₄ | viscous |
| 41 | CH₃ | H | H | CH₃ | — | 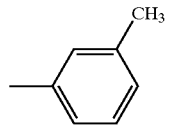 3-CH₃-C₆H₄ | m.p. 72° C. |
| 42 | CH₃ | H | H | C₂H₅ | — | 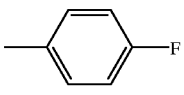 4-F-C₆H₄ | viscous |
| 43 | CH₃ | H | H | C₂H₅ | —CH₂O— | 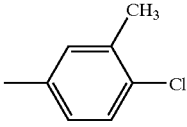 2-CH₃-4-Cl-C₆H₃ | viscous |
| 44 | CH₃ | H | H | CH₃ | — | 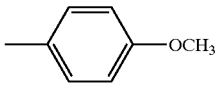 4-OCH₃-C₆H₄ | m.p. 108–10° C. |
| 45 | CH₃ | H | H | CH₃ | — | 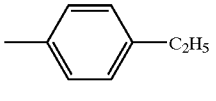 4-C₂H₅-C₆H₄ | oil |
| 46 | CH₃ | H | H | CH₃ | — | 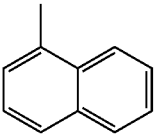 1-naphthyl | m.p. 95° C. |
| 47 | CH₃ | H | H | CH₃ | — | 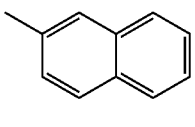 2-naphthyl | m.p. 134° C. |
| 48 | CH₃ | H | H | C₂H₅ | — | 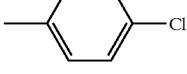 4-Cl-C₆H₄ | m.p. 117° C. (R isomer) |
| 49 | CH₃ | H | H | CH₃ | — | 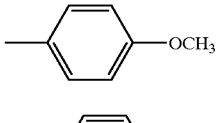 4-OCH₃-C₆H₄ | m.p. 87° C. (R isomer) |
| 50 | CH₃ | H | H | C₂H₅ | — | 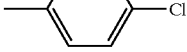 4-Cl-C₆H₄ | m.p. 126° C. (S isomer) |

TABLE A-continued (Ib)

$$NC-N=C(R^1)-N(R^2)-C(R^4)(R^5)-X-R^6$$

| Ex. No. | R¹ | R² | R⁴ | R⁵ | X | R⁶ | Physical const. |
|---|---|---|---|---|---|---|---|
| 51 | CH₃ | H | H | CH₃ | — | 4-methoxyphenyl | m.p. 71° C. (S isomer) |
| 52 | CH₃ | H | H | CH₃ | —CH₂CH₂— | 4-methoxyphenyl | m.p. 87° C. |
| 53 | CH₃ | H | H | CH₃ | —CH₂CH₂— | 4-methoxyphenyl | m.p. 75° C. (R isomer) |
| 54 | CH₃ | H | H | C₂H₅ | —CH₂OCH₂— | phenyl | oil |
| 55 | CH₃ | H | H | C₂H₅ | —CH₂OCH₂— | 2-chlorophenyl | m.p. 83° C. |
| 56 | CH₃ | H | H | C₂H₅ | —CH₂OCH₂— | 2,4-dichlorophenyl | m.p. 95° C. |
| 57 | CH₃ | H | H | C₂H₅ | —CH₂OCH₂— | 5-chloro-2-methylthienyl | oil |
| 58 | CH₃ | H | H | C₂H₅ | —CH₂OCH₂— | 2-methylphenyl | m.p. 86° C. |
| 59 | CH₃ | H | H | C₂H₅ | —CH₂OCH₂— | 3-methoxyphenyl | oil |
| 60 | CH₃ | H | H | C₂H₅ | —CH₂OCH₂— | 2-fluorophenyl | oil |
| 61 | CH₃ | H | H | C₂H₅ | —CH₂OCH₂— | 4-fluorophenyl | oil |

TABLE A-continued (Ib)

$$NC-N=C(R^1)-N(R^2)-C(R^4)(R^5)-X-R^6$$

| Ex. No. | $R^1$ | $R^2$ | $R^4$ | $R^5$ | X | $R^6$ | Physical const. |
|---|---|---|---|---|---|---|---|
| 62 | $CH_3$ | H | H | $C_2H_5$ | —$CH_2OCH_2$— | 3,4-dichlorophenyl | oil |
| 63 | $CH_3$ | H | H | $C_2H_5$ | —$CH_2OCH_2$— | 3-phenoxyphenyl | oil |
| 64 | $CH_3$ | H | H | $C_2H_5$ | —$CH_2OCH_2$— | 2-(trifluoromethyl)phenyl | viscous |
| 65 | $CH_3$ | H | H | $C_2H_5$ | —$CH_2OCH_2$— | 3-chloro-4-methylphenyl | m.p. 79° C. |
| 66 | $CH_3$ | H | H | H | —$CH_2SCH_2$— | 4-chlorophenyl | viscous |
| 67 | $CH_3$ | H | H | H | — | 2,3-dihydro-1,4-benzodioxin-2-yl | oil |
| 68 | $CH_3$ | H | H | H | — | 7-tert-butyl-2,3-dihydro-1,4-benzodioxin-2-yl | oil |
| 69 | $CH_3$ | $CH_3$ | H | H | — | phenyl | oil |
| 70 | $CH_3$ | H | H | H | — | phenyl | m.p. 121° C. |
| 71 | $CH_3$ | H | H | $C_2H_5$ | —$CH_2S$— | 3-chlorophenyl | m.p. 99–102° C. |
| 72 | $CH_3$ | H | H | $CH_3$ | —$CH_2S$— | 3,4-dichlorophenyl | oil |

TABLE A-continued (Ib)
$$NC-N=\underset{\underset{R^1}{|}}{C}-\underset{\underset{R^2}{|}}{N}-\underset{\underset{R^5}{|}}{\overset{\overset{R^4}{|}}{C}}-X-R^6$$

| Ex. No. | R¹ | R² | R⁴ | R⁵ | X | R⁶ | Physical const. |
|---|---|---|---|---|---|---|---|
| 73 | CH₃ | H | H | CH₃ | —CH₂S— |  4-Cl-C₆H₄ | oil |
| 74 | CH₃ | H | H | C₂H₅ | —CH₂S— | 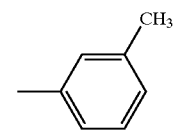 3-CH₃-C₆H₄ | oil |
| 75 | CH₃ | H | H | C₂H₅ | —CH₂S— | 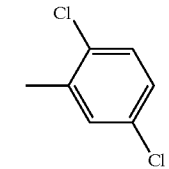 2,5-Cl₂-C₆H₃ | oil |
| 76 | CH₃ | H | H | C₂H₅ | —CH₂SCH₂— | 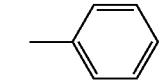 C₆H₅ | oil |
| 77 | CH₃ | H | H | C₂H₅ | —CH₂S— | 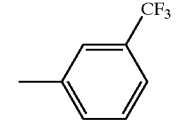 3-CF₃-C₆H₄ | oil |
| 78 | CH₃ | H | H | CH₃ | —CH₂S— | 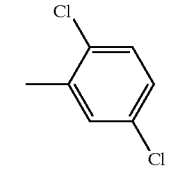 2,5-Cl₂-C₆H₃ | m.p. 145° C. |
| 79 | CH₃ | H | H | C₂H₅ | —CH₂S— | 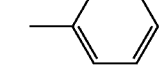 C₆H₅ | oil |
| 80 | CH₃ | H | H | C₂H₅ | —CH₂S— | 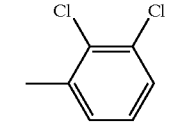 2,3-Cl₂-C₆H₃ | m.p. 135–38° C. |
| 81 | CH₃ | H | H | C₂H₅ | —CH₂S— | 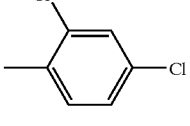 2,4-Cl₂-C₆H₃ | m.p. 240–43° C. |
| 82 | CH₃ | H | H | C₂H₅ | —CH₂S— | 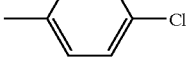 4-Cl-C₆H₄ | oil |

TABLE A-continued
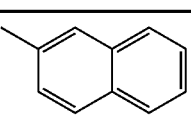
(Ib)
| Ex. No. | R¹ | R² | R⁴ | R⁵ | X | R⁶ | Physical const. |
|---|---|---|---|---|---|---|---|
| 83 | CH₃ | H | H | CH₃ | — | 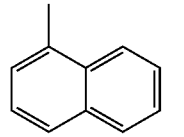 | m.p. 150° C. (S isomer) |
| 84 | CH₃ | H | H | CH₃ | — | 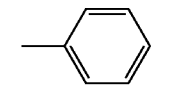 | m.p. 188° C. (S isomer) |
| 85 | CH₃ | H | H | CH₃ | —CH₂CH₂— | 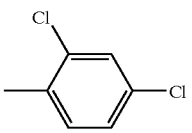 | m.p. 126° C. (S isomer) |
| 86 | CH₃ | H | H | CH₃ | — | 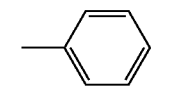 | m.p. 152° C. |
| 87 | CH₃ | H | H | C₂H₅ | —CH₂O— | 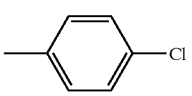 | m.p. 114° C. |
| 88 | CH₃ | H | H | C₂H₅ | —CH₂O— | 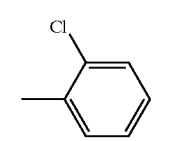 | m.p. 118° C. |
| 89 | CH₃ | H | H | C₂H₅ | —CH₂O— | 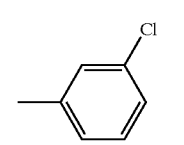 | m.p. 110° C. |
| 90 | CH₃ | H | H | C₂H₅ | —CH₂O— | 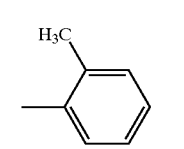 | m.p. 104° C. |
| 91 | CH₃ | H | H | C₂H₅ | —CH₂O— | 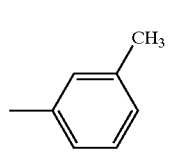 | m.p. 125° C. |
| 92 | CH₃ | H | H | C₂H₅ | —CH₂O— | 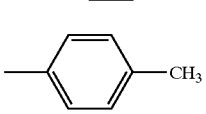 | m.p. 118° C. |
| 93 | CH₃ | H | H | C₂H₅ | —CH₂O— |  | viscous |

TABLE A-continued $$NC-N=C(R^1)-N(R^2)-C(R^4)(R^5)-X-R^6 \quad (Ib)$$

| Ex. No. | $R^1$ | $R^2$ | $R^4$ | $R^5$ | X | $R^6$ | Physical const. |
|---|---|---|---|---|---|---|---|
| 94 | CH$_3$ | H | H | C$_2$H$_5$ | —CH$_2$O— | 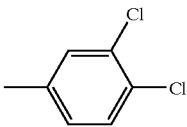 3,4-dichlorophenyl | m.p. 125° C. |
| 95 | CH$_3$ | H | H | C$_2$H$_5$ | —CH$_2$O— | 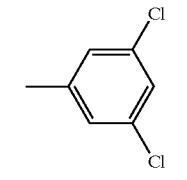 3,5-dichlorophenyl | m.p. 114° C. |
| 96 | CH$_3$ | H | H | H | — |  4-F-phenyl | m.p. 168° C. |
| 97 | CH$_3$ | H | H | H | — | 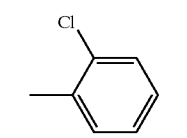 2-Cl-phenyl | m.p. 150° C. |
| 98 | CH$_3$ | H | H | H | — | 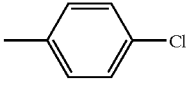 4-Cl-phenyl | m.p. 159° C. |
| 99 | CH$_3$ | H | H | H | — | 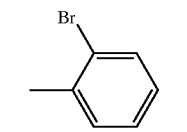 2-Br-phenyl | m.p. 145° C. |
| 100 | CH$_3$ | H | H | H | — | 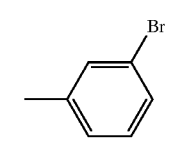 3-Br-phenyl | m.p. 145° C. |
| 101 | CH$_3$ | H | H | H | — | 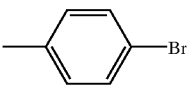 4-Br-phenyl | m.p. 167° C. |
| 102 | CH$_3$ | CH$_3$ | H | H | — | 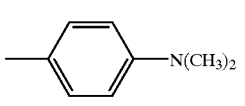 4-N(CH$_3$)$_2$-phenyl | viscous |
| 103 | CH$_3$ | H | H | H | — | 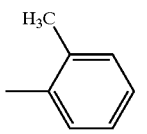 2-CH$_3$-phenyl | m.p. 151° C. |

TABLE A-continued (Ib)
$$NC-N=\underset{R^1}{\overset{}{C}}-\underset{R^2}{\overset{R^4}{N}}-\underset{R^5}{\overset{}{C}}-X-R^6$$

| Ex. No. | R¹ | R² | R⁴ | R⁵ | X | R⁶ | Physical const. |
|---|---|---|---|---|---|---|---|
| 104 | CH₃ | H | H | H | — | 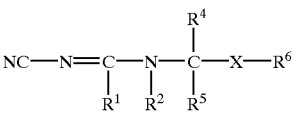 2,3-dimethylphenyl | m.p. 113° C. |
| 105 | CH₃ | H | H | H | — | 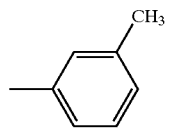 2-OCF₃-phenyl | m.p. 106° C. |
| 106 | CH₃ | H | H | H | — | 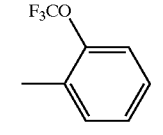 4-OCF₃-phenyl | m.p. 114° C. |
| 107 | CH₃ | H | H | H | — | 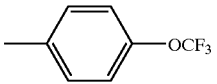 2-NO₂-phenyl | m.p. 192° C. |
| 108 | CH₃ | CH₃ | H | H | — | 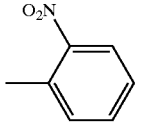 3-NO₂-phenyl | m.p. 124° C. |
| 109 | CH₃ | H | H | H | — | 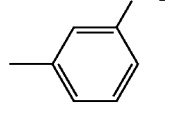 2-OCH₃-phenyl | m.p. 125° C. |
| 110 | CH₃ | H | H | H | — | 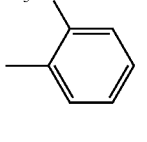 3-OCH₃-phenyl | m.p. 92° C. |
| 111 | CH₃ | H | H | H | — | 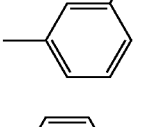 4-OCH₃-phenyl | m.p. 112° C. |
| 112 | CH₃ | H | H | H | — | 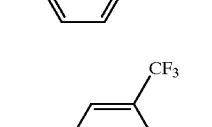 3-CF₃-phenyl | m.p. 111° C. |
| 113 | CH₃ | H | H | H | — | 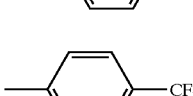 4-CF₃-phenyl | m.p. 130° C. |

TABLE A-continued (Ib)

$$NC-N=C(R^1)-N(R^2)-C(R^4)(R^5)-X-R^6$$

| Ex. No. | R¹ | R² | R⁴ | R⁵ | X | R⁶ | Physical const. |
|---|---|---|---|---|---|---|---|
| 114 | CH₃ | CH₃ | H | H | — | 2,4-dichlorophenyl | m.p. 108° C. |
| 115 | CH₃ | H | H | H | — | 3,4-dichlorophenyl | m.p. 166° C. |
| 116 | CH₃ | H | H | H | — | 2,4-dimethoxyphenyl | m.p. 118° C. |
| 117 | CH₃ | H | H | H | — | 2-(SCF₃)phenyl | m.p. 112° C. |
| 118 | CH₃ | H | H | H | — | 4-(SCF₃)phenyl | m.p. 165° C. |
| 119 | CH₃ | H | H | H | — | 2,4,6-trimethoxyphenyl | m.p. 164° C. |
| 120 | CH₃ | H | H | H | — | 3,4,5-trimethoxyphenyl | m.p. 144° C. |
| 121 | CH₃ | H | H | H | — | 3-chloro-4-fluorophenyl | m.p. 164° C. |
| 122 | CH₃ | H | H | H | — | 2-chloro-6-fluorophenyl | m.p. 160° C. |

TABLE A-continued
(Ib)
$$NC-N=C(R^1)-N(R^2)-C(R^4)(R^5)-X-R^6$$
| Ex. No. | $R^1$ | $R^2$ | $R^4$ | $R^5$ | X | $R^6$ | Physical const. |
|---|---|---|---|---|---|---|---|
| 123 | $CH_3$ | H | H | H | — | 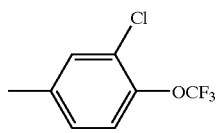 2-Cl, 4-OCF$_3$ phenyl | m.p. 119° C. |
| 124 | $CH_3$ | H | H | H | — | 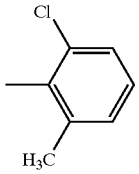 3-Cl, 2-CH$_3$ phenyl | m.p. 174° C. |
| 125 | $CH_3$ | H | H | H | — | 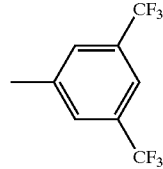 3,5-bis(CF$_3$) phenyl | m.p. 140° C. |
| 126 | $CH_3$ | H | H | H | — | 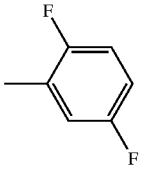 2,5-difluorophenyl | m.p. 148° C. |
| 127 | $CH_3$ | H | H | H | — | 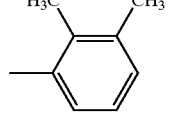 2,3-dimethylphenyl | m.p. 147° C. |
| 128 | $CH_3$ | H | H | H | — | 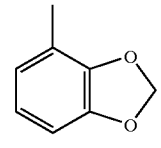 methylenedioxy phenyl | m.p. 154° C. |
| 129 | $CH_3$ | H | H | H | — | 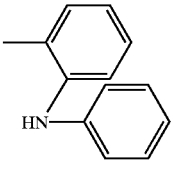 | m.p. 134° C. |
| 130 | $CH_3$ | H | H | $C_3H_7$-i | — | 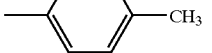 | m.p. 138° C. |
| 131 | $CH_3$ | H | $CH_3$ | $CH_3$ | —C≡C— | 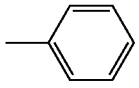 | m.p. 117° C. |

TABLE A-continued (Ib)
$$NC-N=C(R^1)-N(R^2)-C(R^4)(R^5)-X-R^6$$

| Ex. No. | R¹ | R² | R⁴ | R⁵ | X | R⁶ | Physical const. |
|---|---|---|---|---|---|---|---|
| 132 | CH₃ | H | CH₃ | CH₃ | —C≡C— | 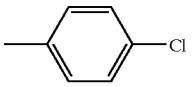 4-Cl-C₆H₄ | m.p. 153° C. |
| 133 | CH₃ | H | CH₃ | CH₃ | —C≡C— | 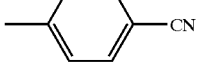 4-CN-C₆H₄ | viscous |
| 134 | CH₃ | H | CH₃ | CH₃ | —C≡C— | 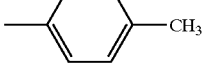 4-CH₃-C₆H₄ | m.p. 138° C. |
| 135 | CH₃ | H | CH₃ | CH₃ | —C≡C— | 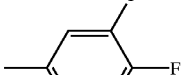 3,4-F₂-C₆H₃ | m.p. 122° C. |
| 136 | CH₃ | H | CH₃ | H | — | 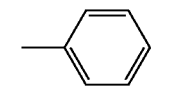 C₆H₅ | m.p. 90° C. |
| 137 | CH₃ | H | CH₃ | H | — | 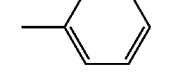 C₆H₅ | m.p. 110° C. (R isomer) |
| 138 | CH₃ | H | CH₃ | H | — | 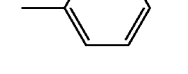 C₆H₅ | m.p. 134° C. (S isomer) |
| 139 | CH₃ | H | CH₃ | H | — | 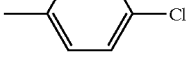 4-Cl-C₆H₄ | viscous |
| 140 | CH₃ | H | CH₃ | H | — | 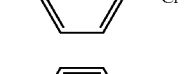 4-Cl-C₆H₄ | m.p. 131° C. (R isomer) |
| 141 | CH₃ | H | CH₃ | H | — | 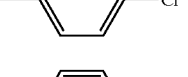 4-Cl-C₆H₄ | viscous (S isomer) |
| 142 | CH₃ | H | C₂H₅ | H | — | 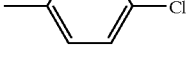 4-Cl-C₆H₄ | viscous |
| 143 | CH₃ | H | C₃H₇-n | H | — | 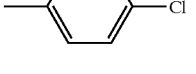 4-Cl-C₆H₄ | m.p. 86° C. |
| 144 | CH₃ | H | CH₃ | H | — | 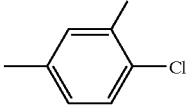 3,4-Cl₂-C₆H₃ | m.p. 156° C. |

TABLE A-continued $$\underset{\underset{R^1}{|}}{NC-N=C}-\underset{\underset{R^2}{|}}{N}-\underset{\underset{R^5}{|}}{\overset{\overset{R^4}{|}}{C}}-X-R^6 \quad \text{(Ib)}$$

| Ex. No. | R¹ | R² | R⁴ | R⁵ | X | R⁶ | Physical const. |
|---|---|---|---|---|---|---|---|
| 145 | CH₃ | H | CH₃ | H | — | 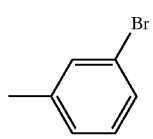 3-Br-C₆H₄ | m.p. 131° C. |
| 146 | CH₃ | H | CH₃ | H | — | 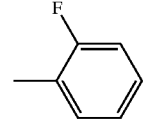 2-F-C₆H₄ | m.p. >250° C. |
| 147 | CH₃ | H | CH₃ | H | — | 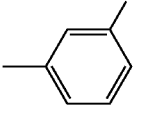 3-CF₃-C₆H₄ | m.p. 105° C. |
| 148 | CH₃ | H | CH₃ | H | — | 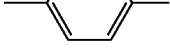 4-F-C₆H₄ | m.p. 115° C. |
| 149 | CH₃ | H | CH₃ | H | — | 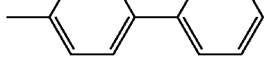 4-biphenyl | m.p. 110° C. |
| 150 | CH₃ | H | CH₃ | H | — | 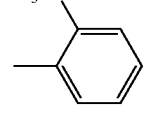 2-OCH₃-C₆H₄ | m.p. 135° C. |
| 151 | CH₃ | H | CH₃ | H | — | 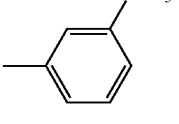 3-OCH₃-C₆H₄ | m.p. 140° C. |
| 152 | CH₃ | H | CH₃ | H | —CH₂CH₂— | 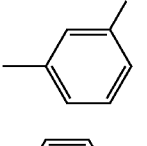 3-CF₃-C₆H₄ | m.p. 95° C. |
| 153 | CH₃ | H | CH₃ | H | —CH₂CH₂— | 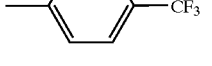 4-CF₃-C₆H₄ | viscous |
| 154 | CH₃ | H | CH₃ | H | —CH₂CH₂— | 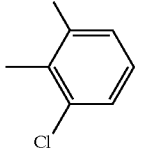 2,6-Cl₂-C₆H₃ | viscous |

TABLE A-continued (Ib)
$$NC-N=C(R^1)-N(R^2)-C(R^4)(R^5)-X-R^6$$

| Ex. No. | R¹ | R² | R⁴ | R⁵ | X | R⁶ | Physical const. |
|---|---|---|---|---|---|---|---|
| 155 | CH₃ | H | H | H | —CH(CH₃)— | phenyl | m.p. 96° C. |
| 156 | CH₃ | H | CH₃ | H | —CH(CH₃)CH₂— | phenyl | viscous |
| 157 | CH₃ | H | CH₃ | H | —CH(CH₃)CH₂— | 3-Cl-phenyl | viscous |
| 158 | CH₃ | H | CH₃ | H | —CH(CH₃)CH₂— | 4-Cl-phenyl | m.p. 108° C. |
| 159 | CH₃ | H | CH₃ | H | —CH(CH₃)CH₂— | 4-F-phenyl | viscous |
| 160 | CH₃ | H | CH₃ | H | —CH(CH₃)CH₂— | 4-Br-phenyl | m.p. 122° C. |
| 161 | CH₃ | H | CH₃ | H | —CH(CH₃)CH₂— | 4-CH₃-phenyl | viscous |
| 162 | CH₃ | H | CH₃ | H | —CH(CH₃)CH₂— | 4-CF₃-phenyl | m.p. 120° C. |
| 163 | CH₃ | H | CH₃ | H | — | benzofuran-2-yl | m.p. 134° C. |
| 164 | CH₃ | H | CH₃ | H | — | 2,3-dihydrobenzofuran-2-yl | viscous |
| 165 | CH₃ | H | H | H | —C(CH₃)=CH— | 4-Cl-phenyl | m.p. 79° C. |
| 166 | CH₃ | H | H | H | —C(CH₃)₂— | 4-Cl-phenyl | m.p. 169° C. |
| 167 | CH₃ | H | CH₃ | H | —CH₂C(CH₃)₂— | 4-Cl-phenyl | viscous |

TABLE A-continued (Ib)

$$NC-N=\underset{\underset{R^1}{|}}{C}-\underset{\underset{R^2}{|}}{N}-\underset{\underset{R^5}{|}}{\overset{\overset{R^4}{|}}{C}}-X-R^6$$

| Ex. No. | R¹ | R² | R⁴ | R⁵ | X | R⁶ | Physical const. |
|---|---|---|---|---|---|---|---|
| 168 | CH₃ | H | CH₃ | H | — | 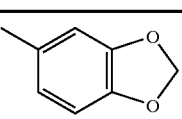 | viscous |
| 169 | CH₃ | H | C₂H₅ | H | —CH₂— | 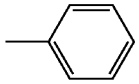 | viscous |
| 170 | CH₃ | H | CH₃ | H | —CH₂CH₂— |  | viscous |
| 171 | CH₃ | H | CH₃ | H | —CH₂— | 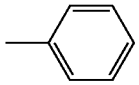 | m.p. 84° C. |
| 172 | CH₃ | H | H | H | —CH(CH₃)CH₂— |  | viscous |
| 173 | CH₃ | H | H | H | —CH(CH₃)CH₂— | 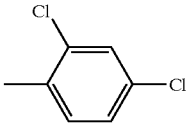 | viscous |
| 174 | CH₃ | H | CH₃ | H | —CH₂O— | 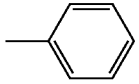 | viscous |
| 175 | CH₃ | H | CH₃ | H | —CH₂O— | 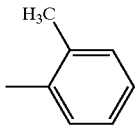 | viscous |
| 176 | CH₃ | H | CH₃ | H | —CH₂O— | 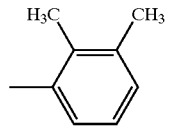 | m.p. 118° C. |
| 177 | CH₃ | H | CH₃ | H | —CH₂O— | 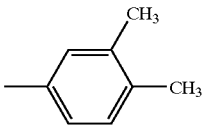 | viscous |
| 178 | CH₃ | H | CH₃ | H | —(CH₂)₃—N(C₂H₅)—CH₂— | 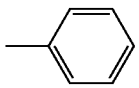 | viscous |
| 179 | H | H | CH₃ | CH₃ | —CH₂CH₂— | 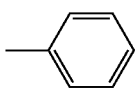 | m.p. 74° C. |

TABLE A-continued $$\text{NC}-\text{N}=\underset{\underset{R^1}{|}}{C}-\underset{\underset{R^2}{|}}{N}-\underset{\underset{R^5}{|}}{\overset{\overset{R^4}{|}}{C}}-X-R^6 \qquad (Ib)$$

| Ex. No. | R¹ | R² | R⁴ | R⁵ | X | R⁶ | Physical const. |
|---|---|---|---|---|---|---|---|
| 180 | H | H | CH₃ | H | —CH₂CH₂— | 3-CF₃-phenyl | m.p. 76° C. |
| 181 | H | H | CH₃ | H | —CH₂CH₂— | 4-CF₃-phenyl | viscous |
| 182 | H | H | CH₃ | H | —CH₂CH₂— | 2,6-dichlorophenyl | viscous |
| 183 | H | H | H | H | —CH(CH₃)— | phenyl | viscous |
| 184 | H | H | CH₃ | H | —CH(CH₃)CH₂— | phenyl | viscous |
| 185 | H | H | CH₃ | CH₃ | —C≡C— | phenyl | m.p. 75° C. |
| 186 | H | H | CH₃ | CH₃ | —C≡C— | 4-Cl-phenyl | m.p. 114° C. |
| 187 | H | H | CH₃ | CH₃ | —C≡C— | 4-CF₃-phenyl | m.p. 80° C. |
| 188 | H | H | CH₃ | CH₃ | —C≡C— | 4-CH₃-phenyl | m.p. 100° C. |
| 189 | H | H | CH₃ | CH₃ | —C≡C— | 3,4-difluorophenyl | viscous |
| 190 | H | H | CH₃ | CH₃ | —C≡C— | 3-thienyl | m.p. 104° C. |
| 191 | H | H | CH₃ | H | — | phenyl | viscous |

TABLE A-continued
(Ib)
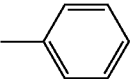
| Ex. No. | R¹ | R² | R⁴ | R⁵ | X | R⁶ | Physical const. |
|---|---|---|---|---|---|---|---|
| 192 | H | H | CH₃ | H | — | 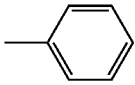 | m.p. 66° C. (R isomer) |
| 193 | H | H | CH₃ | H | — | 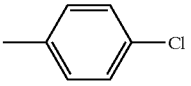 | m.p. 68° C. (S isomer) |
| 194 | H | H | CH₃ | H | — | 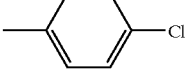 | viscous |
| 195 | H | H | C₂H₅ | H | — | | viscous |
| 196 | H | H | C₃H₇-n | H | — | | viscous |
| 197 | H | H | CH₃ | H | —CH₂CH₂— | 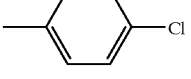 | viscous |
| 198 | H | H | H | H | —CH(CH₃)CH₂— | | m.p. 95° C. |
| 199 | H | H | CH₃ | H | — | 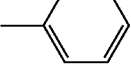 | m.p. 78° C. |
| 200 | H | H | H | H | —C(CH₃)₂— | 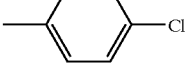 | m.p. 84° C. |
| 201 | H | H | CH₃ | H | —CH₂—C(CH₃)₂— | | viscous |
| 202 | CH₃ | H | H | H | —CH₂— | 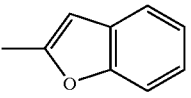 | m.p. 153° C. |
| 203 | CH₃ | CH₃ | H | CH₃ | — | | log P (pH 2.3) 2.32 |
| 204 | CH₃ | H | H | CH₃ | | 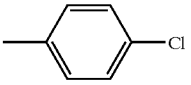 | log P (pH 2.3) 1.63 |

TABLE A-continued $$NC-N=C(R^1)-N(R^2)-C(R^4)(R^5)-X-R^6 \quad (Ib)$$

| Ex. No. | R¹ | R² | R⁴ | R⁵ | X | R⁶ | Physical const. |
|---|---|---|---|---|---|---|---|
| 205 | CH₃ | H | H | C₂H₅ | — | 4-F-C₆H₄- | m.p. 143° C. (S isomer) |
| 206 | CH₃ | H | H | C₂H₅ | — | 2,5-F-C₆H₃- | m.p. 135° C. (R isomer) |
| 207 | CH₃ | H | H | C₂H₅ | —CH₂—CH₂— | 2,5-dimethylthiophen-yl | wax |
| 208 | CH₃ | H | H | CH₃ | — | 4-F-C₆H₄- | log P (pH 2.3) 1.71 (R isomer) |
| 209 | C₃H₇-n | H | H | CH₃ | — | C₆H₅- | oil |
| 210 | C₃H₇-n | H | H | CH₃ | — | 4-Cl-C₆H₄- | m.p. 135° C. |
| 211 | H | H | H | CH₃ | — | 4-Cl-C₆H₄- | oil (R isomer) |
| 212 | H | H | H | CH₃ | — | 3,4-Cl₂-C₆H₃- | oil |
| 213 | H | H | H | H | —CH₂CH₂— | C₆H₅- | oil |
| 214 | H | H | H | H | —(CH₂)₂—N(C₄H₉-i)—CH₂— | C₆H₅- | oil |
| 215 | H | H | H | CH₃ | —(CH₂)₃—N(C₂H₅)—CH₂— | C₆H₅- | oil |
| 216 | H | H | H | CH₃ | — | 2,3-dihydrobenzofuran-2-yl | oil |
| 217 | H | H | H | CH₃ | —CH₂C(CH₃)₂— | 4-Cl-C₆H₄- | oil |

TABLE A-continued
$$NC-N=C(R^1)-N(R^2)-C(R^4)(R^5)-X-R^6 \quad (Ib)$$
| Ex. No. | R¹ | R² | R⁴ | R⁵ | X | R⁶ | Physical const. |
|---|---|---|---|---|---|---|---|
| 218 | H | H | H | CH₃ | —CH₂CH₂— |  phenyl | oil |
| 219 | H | H | H | CH₃ | —CH(CH₃)CH₂— | 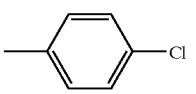 4-Cl-phenyl | oil |
| 220 | H | H | CH₃ | CH₃ | —C≡C— | 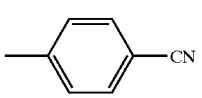 4-CN-phenyl | oil |
| 221 | H | H | H | CH₃ | — | 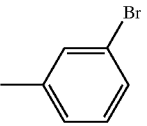 3-Br-phenyl | oil |
| 222 | H | H | H | CH₃ | — | 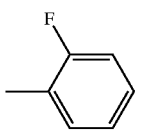 2-F-phenyl | oil |
| 223 | H | H | H | CH₃ | — | 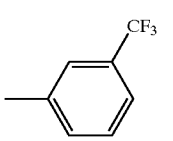 3-CF₃-phenyl | oil |
| 224 | H | H | H | CH₃ | — | 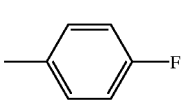 4-F-phenyl | oil |
| 225 | H | H | H | CH₃ | — | 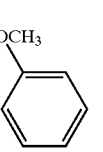 2-OCH₃-phenyl | oil |
| 226 | H | H | H | CH₃ | — | 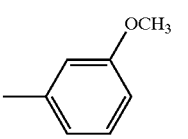 3-OCH₃-phenyl | oil |
| 227 | C₂H₅ | H | H | CH₃ | — |  phenyl | oil |
| 228 | C₂H₅ | H | H | CH₃ | — | 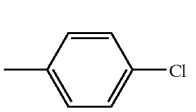 4-Cl-phenyl | m.p. 111° C. |

TABLE A-continued
(Ib)
$$NC-N=C(R^1)-N(R^2)-C(R^4)(R^5)-X-R^6$$
| Ex. No. | $R^1$ | $R^2$ | $R^4$ | $R^5$ | X | $R^6$ | Physical const. |
|---|---|---|---|---|---|---|---|
| 229 | $C_2H_5$ | H | H | $C_2H_5$ | — | 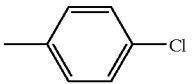 4-Cl-C6H4 | oil |
| 230 | $C_2H_5$ | H | H | $C_3H_7$-n | — | 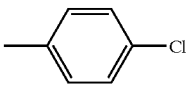 4-Cl-C6H4 | oil |
| 231 | $C_2H_5$ | H | H | $CH_3$ | — | 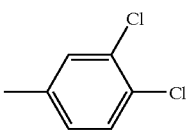 3,4-diCl-C6H3 | m.p. 109° C. |
| 232 | $C_2H_5$ | H | H | $CH_3$ | — | 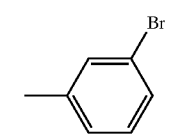 3-Br-C6H4 | oil |
| 233 | $C_2H_5$ | H | H | $CH_3$ | — | 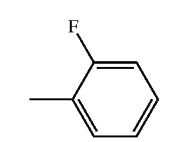 2-F-C6H4 | m.p. 87° C. |
| 234 | $C_2H_5$ | H | H | $CH_3$ | — | 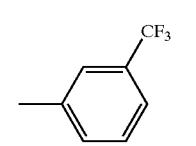 3-CF3-C6H4 | m.p. 81° C. |
| 235 | $C_2H_5$ | H | H | $CH_3$ | — | 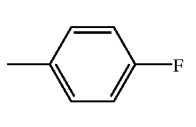 4-F-C6H4 | oil |
| 236 | $C_2H_5$ | H | H | $CH_3$ | — | 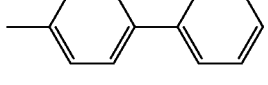 4-biphenyl | m.p. 163° C. |
| 237 | $C_2H_5$ | H | H | $CH_3$ | — | 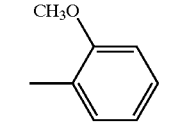 2-OCH3-C6H4 | m.p. 115° C. |
| 238 | $C_2H_5$ | H | H | $CH_3$ | — | 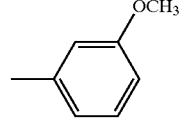 3-OCH3-C6H4 | oil |
| 239 | $C_2H_5$ | H | H | $CH_3$ | — | 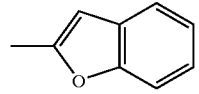 2-benzofuryl | oil |

TABLE A-continued
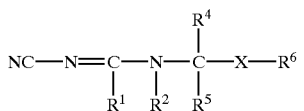
(Ib)
| Ex. No. | R¹ | R² | R⁴ | R⁵ | X | R⁶ | Physical const. |
|---|---|---|---|---|---|---|---|
| 240 | CH₃ | H | H | H | —CH₂— | 2-thienyl | m.p. 107° C. |
| 241 | CH₃ | H | H | H | — | 2-thienyl | m.p. 113° C. |
| 242 | CH₃ | H | H | H | — | 2-furyl | m.p. 101° C. |
| 243 | CH₃ | H | H | H | —CH₂— | phenyl | m.p. 138° C. |
| 244 | CH₃ | H | H | H | —CH₂CH₂— | phenyl | m.p. 67° C. |
| 245 | CH₃ | H | H | H | — | 2,3-dimethoxyphenyl | oil |
| 246 | CH₃ | H | H | H | — | 2,6-dimethoxyphenyl | m.p. 86° C. |
| 247 | CH₃ | H | H | H | — | 3,5-dimethoxyphenyl | m.p. 132° C. |
| 248 | CH₃ | H | H | H | —CH₂ | 4-fluorophenyl | m.p. 133° C. |
| 249 | CH₃ | H | H | CH₃ | —CH₂O— | 4-fluorophenyl | oil |
| 250 | H | H | CH₃ | CH₃ | —CH₂CH₂— | 4-chlorophenyl | m.p. 107° C. |

TABLE A-continued (Ib)
$$NC-N=C(R^1)-N(R^2)-C(R^4)(R^5)-X-R^6$$

| Ex. No. | R¹ | R² | R⁴ | R⁵ | X | R⁶ | Physical const. |
|---|---|---|---|---|---|---|---|
| 251 | H | H | H | CH₃ | —CH(CH₃)CH₂— | 4-Br-C₆H₄ | oil |
| 252 | H | H | H | CH₃ | —CH(CH₃)CH₂— | 2,5-(CH₃)₂-C₆H₃ | oil |
| 253 | H | H | H | H | —CH(CH₃)CH₂— | 2,4-Cl₂-C₆H₃ | oil |
| 254 | H | H | H | CH₃ | —CH₂O— | 2-naphthyl | m.p. 126° C. |
| 255 | H | H | H | CH₃ | —CH₂O— | C₆H₅ | oil |
| 256 | H | H | H | CH₃ | —CH₂O— | 4-F-C₆H₄ | oil |
| 257 | H | H | H | CH₃ | —CH₂O— | 2-CH₃-C₆H₄ | oil |
| 258 | H | H | H | CH₃ | —CH₂O— | 2,3-(CH₃)₂-C₆H₃ | m.p. 108° C. |
| 259 | H | H | H | CH₃ | —CH₂O— | 2,4-(CH₃)₂-C₆H₃ | m.p. 112° C. |
| 260 | C₃H₇-n | H | H | CH₃ | — | 2-benzofuryl | oil |
| 261 | H | H | H | H | —CH₂— | 2-thienyl | oil |

TABLE A-continued
(Ib)
$$NC-N=C(R^1)-N(R^2)-C(R^4)(R^5)-X-R^6$$
| Ex. No. | R¹ | R² | R⁴ | R⁵ | X | R⁶ | Physical const. |
|---|---|---|---|---|---|---|---|
| 262 | H | H | H | H | — | 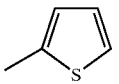 2-thienyl | oil |
| 263 | H | H | H | H | — | 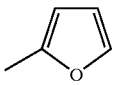 2-furyl | oil |
| 264 | H | H | H | H | —CH₂— |  phenyl | oil |
| 265 | H | H | H | H | — | 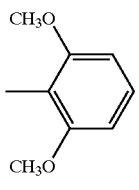 2,6-dimethoxyphenyl | m.p. 69° C. |
| 266 | H | H | H | H | —CH₂— |  4-F-phenyl | oil |
| 267 | H | H | H | H | — | 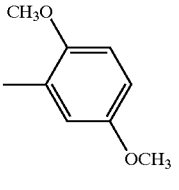 2-methoxy,5-OCH₃ | m.p. 77° C. |
| 268 | CH₃ | H | H | H | — | 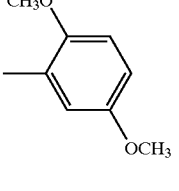 | m.p. 135° C. |
| 269 | CH₃ | H | H | H | —(CH₂)₃— |  phenyl | m.p. 106° C. |
| 270 | H | H | H | H | —(CH₂)₃— |  pyridyl | oil |
| 271 | C₂H₅ | H | H | CH₃ | — | 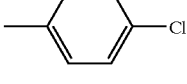 4-Cl-phenyl | m.p. 136° C. ((+)-Isomer) |
| 272 | C₂H₅ | H | H | CH₃ | — | 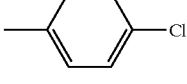 4-Cl-phenyl | m.p. 125° C. ((−)-isomer) |

TABLE A-continued
(Ib)
$$NC-N=C(R^1)-N(R^2)-C(R^4)(R^5)-X-R^6$$
| Ex. No. | $R^1$ | $R^2$ | $R^4$ | $R^5$ | X | $R^6$ | Physical const. |
|---|---|---|---|---|---|---|---|
| 273 | $C_3H_7$-n | H | H | $CH_3$ | | 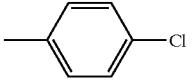 | m.p. 79° C. |
| 274 | $C_3H_7$-n | H | H | $CH_3$ | — | 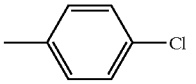 | m.p. 118° C. ((+)-isomer) |
| 275 | $C_3H_7$-n | H | H | $CH_3$ | |  | m.p. 116° C. ((−)-isomer) |
| 276 | $CH_3$ | H | H | $C_2H_5$ | —$CH_2OCH_2$— | 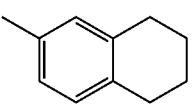 | oil |
| 277 | $CH_3$ | H | H | $C_2H_5$ | —$CH_2OCH_2$— | 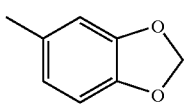 | oil |
| 278 | $CH_3$ | H | H | $C_2H_5$ | —$CH_2OCH_2$— | 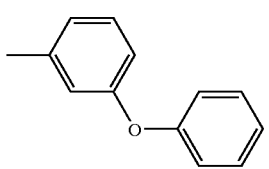 | oil (R isomer) |
| 279 | $CH_3$ | H | H | $C_2H_5$ | — | 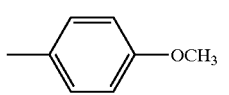 | m.p. 134° C. |
| 280 | $CH_3$ | H | H | $C_2H_5$ | | 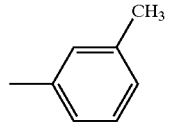 | m.p. 62° C. |
| 281 | $CH_3$ | H | H | $C_2H_5$ | — | 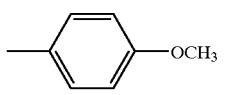 | wax (S isomer) |
| 282 | $CH_3$ | H | H | $C_2H_5$ | — | 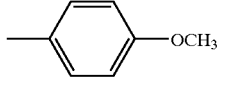 | m.p. 134° C. (R isomer) |
| 283 | $CH_3$ | H | H | $C_2H_5$ | | 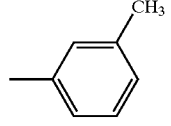 | m.p. 98° C. (R isomer) |

TABLE A-continued

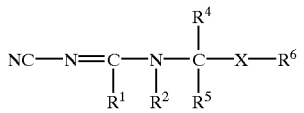
(Ib)

| Ex. No. | R¹ | R² | R⁴ | R⁵ | X | R⁶ | Physical const. |
|---|---|---|---|---|---|---|---|
| 284 | CH₃ | H | H | C₂H₅ | — | 3-methylphenyl (with CH₃) | m.p. 98° C. (S isomer) |
| 285 | CH₃ | H | H | C₂H₅ | — | 2-methoxyphenyl (CH₃O) | m.p. 103° C. (S isomer) |
| 286 | CH₃ | H | H | C₂H₅ | — | 2-methoxyphenyl (CH₃O) | log P(pH 2.3) 2.05 (R isomer) |
| 287 | CH₃ | H | H | CH₃ | | 4-methylphenyl (CH₃) | log P (pH 2.3) 1.93 (S isomer) |
| 288 | CH₃ | H | H | CH₃ | — | 4-fluorophenyl (F) | log P (pH 2.3) 1.71 (S isomer) |
| 289 | CH₃ | H | H | CH₃ | — | 3-chlorophenyl (Cl) | m.p. 148° C. (S isomer) |
| 290 | CH₃ | H | H | CH₃ | | 3-chlorophenyl (Cl) | m.p. 139° C. (R isomer) |
| 291 | CH₃ | H | H | C₂H₅ | | 3-chlorophenyl (Cl) | m.p. 134° C. |
| 292 | CH₃ | H | H | C₂H₅ | | 3-chlorophenyl (Cl) | m.p. 113° C. (S isomer) |
| 293 | CH₃ | H | H | CH₃ | — | 4-methylphenyl (CH₃) | log P (pH 2.3) 1.94 (R isomer) |

TABLE A-continued (Ib)
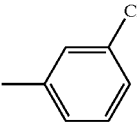

| Ex. No. | R¹ | R² | R⁴ | R⁵ | X | R⁶ | Physical const. |
|---|---|---|---|---|---|---|---|
| 294 | CH₃ | H | H | C₂H₅ | — | 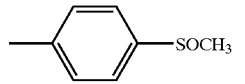 3-Cl-C₆H₄ | m.p. 118° C. (R isomer) |
| 295 | CH₃ | H | H | CH₃ | — | 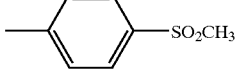 4-SOCH₃-C₆H₄ | wax |
| 296 | CH₃ | H | H | CH₃ | — | 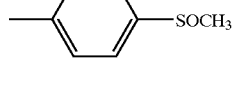 4-SO₂CH₃-C₆H₄ | m.p. 148° C. (S isomer) |
| 297 | CH₃ | H | H | CH₃ | — | 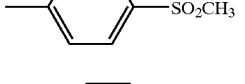 4-SOCH₃-C₆H₄ | log P (pH 2.3) 0.78 (R isomer) |
| 298 | CH₃ | H | H | CH₃ | — | 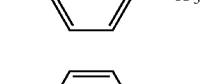 4-SO₂CH₃-C₆H₄ | m.p. 149° C. (R isomer) |
| 299 | CH₃ | H | H | CH₃ | — | 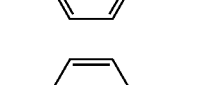 4-CF₃-C₆H₄ | m.p. 140° C. |
| 300 | CH₃ | H | H | CH₃ | — | 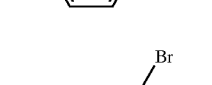 4-CF₃-C₆H₄ | m.p. 138° C. (S isomer) |
| 301 | CH₃ | H | H | CH₃ | — | 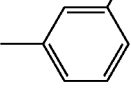 4-CF₃-C₆H₄ | m.p. 133° C. (R isomer) |
| 302 | CH₃ | H | H | CH₃ | — | 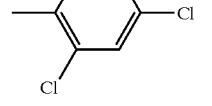 3-Br-C₆H₄ | m.p. 141° C. |
| 303 | CH₃ | H | H | CH₃ | — | 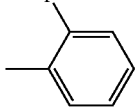 2,4-Cl₂-C₆H₃ | m.p. 193° C. |
| 304 | CH₃ | H | H | CH₃ | — | 2-F-C₆H₄ | m.p. 132° C. |

TABLE A-continued (Ib)

NC—N=C(R¹)—N(R²)—C(R⁴)(R⁵)—X—R⁶

| Ex. No. | R¹ | R² | R⁴ | R⁵ | X | R⁶ | Physical const. |
|---|---|---|---|---|---|---|---|
| 305 | CH₃ | H | H | CH₃ | — | 2,4-dimethylphenyl | m.p. 158° C. |
| 306 | CH₃ | H | H | C₃H₇-i | — | 4-chlorophenyl | log P (pH 2.3) 2.58 |
| 307 | CH₃ | H | H | CH₃ | — | 2,4-dimethylphenyl | m.p. 133° C. |
| 308 | CH₃ | H | H | CH₃ | — | 2,3-dimethylphenyl | m.p. 147° C. |
| 309 | CH₃ | H | H | CH₃ | — | 2-methyl-3,6-dimethoxyphenyl | m.p. 126° C. |
| 310 | CH₃ | H | H | C₂H₅ | —CH₂CH₂ | 2,5-dimethylthien-3-yl | wax |
| 311 | CH₃ | H | H | CH₃ | — | 4-tert-butylphenyl | m.p. 133° C. |
| 312 | CH₃ | H | H | CH₃ | — | cyclohex-2-enyl | viscous |
| 313 | CH₃ | H | H | CH₃ | — | 2,3,4,6-tetramethylphenyl | m.p. 136° C. |
| 314 | CH₃ | H | H | CH₃ | —CH₂CH₂— | 2,5-dimethylthien-3-yl | |

TABLE A-continued
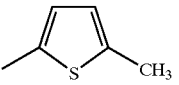
(Ib)
| Ex. No. | R¹ | R² | R⁴ | R⁵ | X | R⁶ | Physical const. |
|---|---|---|---|---|---|---|---|
| 315 | $C_2H_5$ | H | H | $CH_3$ | —$CH_2CH_2$— | 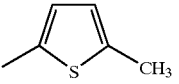 | |
| 316 | $C_3H_7$-n | H | H | $CH_3$ | —$CH_2CH_2$— | 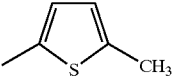 | |
| 317 | $C_3H_7$-i | H | H | $CH_3$ | —$CH_2CH_2$— | 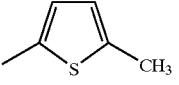 | |
| 318 | $C_2H_5$ | H | H | $C_2H_5$ | —$CH_2CH_2$— | 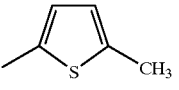 | |
| 319 | $C_3H_7$-n | H | H | $C_2H_5$ | —$CH_2CH_2$— | 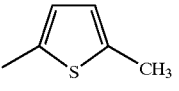 | |
| 320 | $C_3H_7$-i | H | H | $C_2H_5$ | —$CH_2CH_2$— | 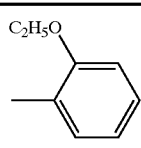 | |
TABLE B
$$NC-N=C-N-Y-R^7$$
$$\phantom{NC-N=}\overset{|}{R^1}\ \overset{|}{R^2}$$
(Ic)
| Ex. No. | R¹ | R² | Y | R⁷ | Physical const. |
|---|---|---|---|---|---|
| B1 | $CH_3$ | H | — | 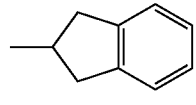 | m.p. 121° C. |
| B2 | H | H | — | 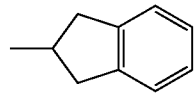 | m.p. 137° C. |
| B3 | $CH_3$ | H | — | 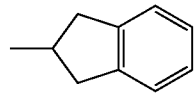 | m.p. 205° C. |

TABLE B-continued $$NC-N=C-N-Y-R^7$$
$$\quad\quad\quad | \quad |$$
$$\quad\quad\quad R^1 \; R^2$$
(Ic)

| Ex. No. | R¹ | R² | Y | R⁷ | Physical const. |
|---|---|---|---|---|---|
| B4 | $C_3H_7$-n | H | — | 2-indanyl (methyl-substituted) | m.p. 128° C. |
| B5 | $C_2H_5$ | H | — | 1-indanyl (methyl-substituted) | m.p. 136° C. |
| B6 | $C_3H_7$-n | H | — | 1-indanyl (methyl-substituted) | m.p. 82° C. |
| B7 | $C_2H_5$ | H | — | 2-indanyl (methyl-substituted) | m.p 148° C. |
| B8 | $CH_3$ | H | — | cyclohexyl-C(CH$_3$)$_2$-phenyl | m.p. 181° C. |
| B9 | $CH_3$ | H | — | tetrahydrothiophene-1,1-dioxide (methyl-substituted) | m.p. 151° C. (decomp.) |
| B10 | $CH_3$ | H | — | 5-methyl-4-phenyl-1,3-dioxane | m.p. 213° C. |
| B11 | $CH_3$ | H | — | cyclohexyl-CH$_2$-cyclohexyl-N(pyrrolidin-2-one) | viscous |
| B12 | $CH_3$ | H | — | dibenz[b,f]oxepine (methyl-substituted) | m.p. 179° C. |
| B13 | $CH_3$ | H | — | dibenzo dioxepine (methyl-substituted) | m.p. 84° C. |

USE EXAMPLES

Example A

Critical Concentration Test

| | |
|---|---|
| Test nematode: | Meloidogyne incognita |
| Solvent: | 4 parts by weight of acetone |
| Emulsifier: | 1 part by weight of alkylaryl polyglycol ether |

To produce a suitable preparation of active compound, 1 part by weight of active compound is mixed with the stated amount of solvent, the stated amount of emulsifier is added and the concentrate is diluted to the desired concentration.

The preparation of active compound is intimately mixed with the soil which is contaminated with the test nematodes. The concentration of the active compound in the preparation is here virtually unimportant, only the amount of active compound per volume unit of soil, which is stated in ppm (=mg/l), is decisive. The treated soil is filled into pots, lettuce is sown in and the pots are kept at a greenhouse temperature of 25° C.

After three weeks, the roots of the lettuces are examined for infestation by nematodes (root galls), and the efficacy of the active compound in % is determined. The efficacy is 100% when infestation is avoided completely and 0% when the infestation level is just as high as in the control plants in untreated, but equally infested, soil.

In this test a kill of 100% was effected, for example, by the compound of Preparation Example 1 at an exemplary active compound concentration of 20 ppm.

What is claimed is:

1. A compound of formula (Ib)

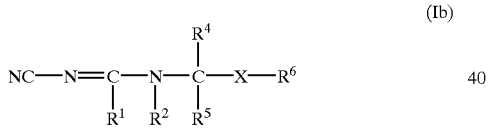

(Ib)

wherein $R^1$ represents (i) hydrogen; (ii) optionally halogen-, cyano-, or $C_1$–$C_4$-alkoxy-substituted $C_1$–$C_4$-alkyl; (iii) $C_3$–$C_6$-cycloalkyl that is optionally mono- to trisubstituted by identical or different substituents selected from the group I;, consisting of halogen and $C_1$–$C_4$-alkyl; or (iv) phenyl that is mono- to trisubstituted by identical or different substituents selected from the group consisting of hydroxyl; amino; cyano; nitro; halogen; optionally hydroxyl-, cyano-, or halogen-substituted $C_1$–$C_4$-alkyl, $C_1$–$C_4$-alkoxy, $C_1$–$C_4$-alkylamino, or di($C_1$–$C_4$-alkyl)amino; optionally halogen-substituted $C_1$–$C_4$-alkyl-carbonyl, $C_1$–$C_4$-alkoxycarbonyl, $C_1$–$C_4$-alkyl-carbonyl-amino, $C_1$–$C_4$-alkylthio, $C_1$–$C_4$-alkylsulphinyl, or $C_1$–$C_4$-alkylsulphonyl; aminocarbonyl; aminothiocarbonyl; $C_1$–$C_4$-alkylaminocarbonyl; di($C_1C_4$-alkyl)aminocarbonyl; aminosulphonyl; $C_1$–$C_4$-alkylaminosulphonyl; di($C_1$–$C_4$-alkyl)aminosulphonyl; and phenyl, phenoxy, phenylthio, phenylsulphinyl, phenylsulphonyl, benzyl, or phenylamino, wherein each such phenyl, phenoxy, phenylthio, phenylsulphinyl, phenylsulphonyl, benzyl, or phenylamino is optionally substituted by one or more hydroxyl, cyano, nitro, halogen, $C_1$–$C_4$-alkyl, $C_1$–$C_4$-alkoxy, $C_1$–$C_4$-alkylthio, $C_1$–$C_4$-alkylthio, $C_1$–$C_4$-alkylsulphinyl, or $C_1$–$C_4$-alkylsulphonyl, or by one or more $C_1$–$C_4$-halogenoalkyl, $C_1$–$C_4$-halogenoalkoxy, $C_1$–$C_4$-halogenoalkylthio, $C_1$–$C_4$-halogenoalkylsulphinyl, or $C_1$–$C_4$-halogenoalkylsulphonyl having 1 to 5 identical or different halogen atoms selected from the series consisting of chlorine, fluorine, and bromine, $R^2$ represents (i) hydrogen; (ii) optionally halogen-, cyano-, or $C_1$–$C_4$-alkoxy-substituted $C_1$–$C_4$-alkyl; or (iii) $C_3$–$C_6$-cycloalkyl that is optionally mono- or trisubstituted by identical or different substituents selected from the group consisting of halogen and $C_1$–$C_4$-alkyl, $R^4$ and $R^5$ independently of one another represent (i) hydrogen; (ii) optionally halogen-, cyano-, or $C_1$–$C_4$-alkoxy-substituted $C_1$–$C_4$-alkyl; or (iii) $C_3$–$C_6$-cycloalkyl that is optionally mono- to trisubstituted by identical or different substituents selected from the group consisting of halogen and $C_1$–$C_4$-alkyl, $R^6$ represents (i) phenyl or naphthyl, each of which is optionally mono- to trisubstituted by identical or different substituents selected from the group consisting of cyano; nitro; amino; fluorine; chlorine; bromine; methyl; ethyl; n- or i-propyl; n-, i-, s-, or t-butyl; methoxy; ethoxy; n- or i-propoxy; trifluoromethyl; difluoromethyl; trifluoromethoxy; difluoromethoxy; trifluoromethylthio; methylamino; dimethylamino; acetyl; propionyl; methoxycarbonyl; ethoxycarbonyl; methylthio; methylsulphinyl; methylsulphonyl; methylaminocarbonyl; ethylaminocarbonyl; n- or i-propylaminocarbonyl; dimethylaminocarbonyl; diethylaminocarbonyl; optionally cyano-, nitro-, fluorine-, chlorine-, methyl-, methoxy-, methylthio-, methylsulphinyl-, methylsulphonyl-, trifluoromethyl-, trifluoromethoxy-, trifluoromethylthio-, trifluoromethylsulphinyl-, or trifluoromethylsulphonyl-substituted phenyl, phenoxy, phenylthio, phenylsulphinyl, phenylsulphonyl, benzyl, or phenylamino; (ii) cyclopentane, or cyclohexane, each of which is optionally mono- to trisubstituted by identical or different substituents selected from the group consisting of fluorine, chlorine, methyl, ethyl, i-propyl, methoxy, ethoxy, trifluoromethyl, and trifluoromethoxy; or (iii) heterocycles having the formulas

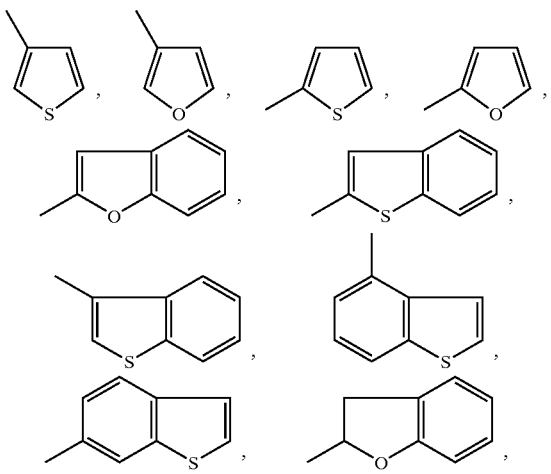

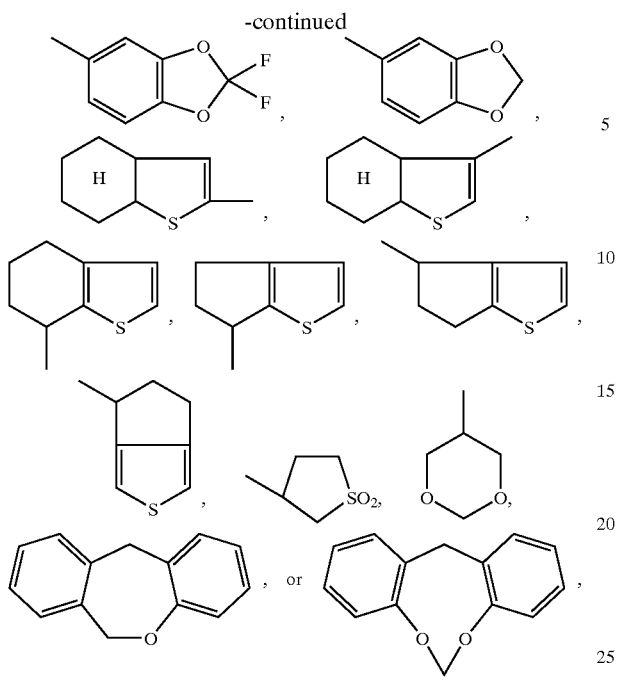

each of which is optionally mono- to pentasubstituted by identical or different substituents selected from the group consisting of cyano; nitro; fluorine; chlorine; bromine; methyl; ethyl; n- or i-propyl; methoxy; trifluoromethyl; dimethylamino; phenyl that is optionally substituted with substituents selected from the group consisting of cyano; nitro; amino; fluorine; chlorine; bromine; methyl; ethyl; n- or i-propyl; n-, i-, s-, or t-butyl; methoxy; ethoxy; n- or i-propoxy; trifluoromethyl; difluoromethoxy; trifluoromethoxy; difluoromethoxy; trifluoromethylthio; methylamino; dimethylamino; acetyl; propionyl; methoxycarbonyl; ethoxycarbonyl; methylthio; methylsulphinyl; methylsulphonyl; methylaminocarbonyl; ethylaminocarbonyl; n- or i-propylaminocarbonyl; dimethylaminocarbonyl; diethylaminocarbonyl; and optionally cyano-, nitro-, fluorine-, chlorine-, methyl-, methoxy-, methylthio-, methylsulphinyl-, methylsulphonyl-, trifluoromethyl-, trifluoromethoxy-, trifluoromethylthio-, trifluoromethylsulphinyl-, or trifluoromethylsulphonyl-substituted phenyl, phenoxy, phenylthio, phenylsulphinyl, phenylsulphonyl, benzyl, or phenylamino, X represents (i) a single bond or (ii) a grouping selected from the group consisting of —CH$_2$—, —(CH$_2$)$_2$—, —(CH$_2$)$_3$—, —CH(CH$_3$)—, —C(CH$_3$)$_2$—, —CH$_2$C(CH$_3$)$_2$—, —CH(CH$_3$)CH$_2$—, —CH$_2$O—, —CH$_2$S—, —(CH$_2$)$_2$O—, —(CH$_2$)$_2$S—, —CH$_2$OCH$_2$—, —CH$_2$SCH$_2$—, —C(CH$_3$)=CH—, —C≡C—, —(CH$_2$)$_3$—N(CH$_3$)—, —(CH$_2$)$_3$—N(C$_2$H$_5$)—, —(CH$_2$)$_3$—N(CH$_3$)—CH$_2$—, and —(CH$_2$)$_3$—N(C$_2$H$_5$)—CH$_2$—.

2. A compound of the formula (Ib) according to claim 1 wherein

R$^1$ represents (i) hydrogen; (ii) optionally cyano-, fluorine, chlorine-, methoxy-, or ethoxy-substituted methyl, ethyl, n- or i-propyl, or n-, i-, s-, or t-butyl; (iii) cyclopropyl, cyclopentyl, or cyclohexyl, each of which is optionally mono- to trisubstituted by identical or different substituents selected from the group consisting of fluorine, chlorine, bromine, methyl, and ethyl; or (iv) phenyl that is optionally mono- to trisubstituted by identical or different substituents selected from the group of cyano; nitro; amino; fluorine; chlorine; bromine; optionally fluorine- or chlorine-substituted methyl, ethyl, n- or i-propyl, n-, i-, s-, or t-butyl, methoxy, ethoxy, n- or i-propoxy, n-, i-, s-, or t-butoxy, methylamino, ethylamino, n- or i-propylamino, or dimethylamino; optionally fluorine- and/or chlorine-substituted acetyl, propionyl, methoxycarbonyl, ethoxycarbonyl, n- or i-propoxycarbonyl, methylthio, methylsulphinyl, methylsulphonyl, ethylthio, ethylsulphinyl, or ethylsulphonyl; aminocarbonyl; aminothiocarbonyl; methylaminocarbonyl; ethylaminocarbonyl; n- or i-propylaminocarbonyl; dimethylaminocarbonyl; diethylaminocarbonyl; aminosulphonyl; methylaminosulphonyl; ethylaminosulphonyl; dimethylaminosulphonyl; diethylaminosulphonyl; optionally cyano-, nitro-, fluorine-, chlorine-, methyl-, ethyl-, n- or i-propyl-, n-, i-, s-, or t-butyl-, trifluoromethyl-, methoxy-, ethoxy-, n- or i-propoxy-, methylthio-, ethylthio-, n- or i-propylthio-, methylsulphinyl-, ethylsulphinyl-, n- or i-propylsulphinyl-, methylsulphonyl-, ethylsulphonyl-, n- or i-propylsulphonyl-, difluoromethoxy-, trifluoromethoxy-, trifluoromethylthio-, trifluoromethylsulphinyl-, or trifluoromethylsulphonyl-substituted phenyl, phenoxy, phenylthio, phenylsulphinyl, phenylsulphonyl, benzyl, or phenylamino, R$^2$ represents (i) hydrogen; (ii) optionally cyano-, fluorine-, chlorine-, methoxy-, or ethoxy-substituted methyl, ethyl, n- or i-propyl and n-, i-, s-, or t-butyl; or (iii) cyclopropyl, cyclopentyl, or cyclohexyl, each or which is optionally mono- to trisubstituted by identical or different substituents selected from the group consisting of fluorine, chlorine, bromine, methyl, and ethyl, and R$^4$ and R$^5$ independently of one another represent (i) hydrogen; (ii) optionally cyano-, fluorine-, chlorine-, methoxy-, or ethoxy-substituted methyl, ethyl, n- or i-propyl, or n-, i-, s-, or t-butyl; or (iii) cyclopropyl, cyclopentyl, or cyclohexyl, each of which is optionally mono- to trisubstituted by identical or different substituents selected from the group consisting of fluorine, chlorine, bromine, methyl, and ethyl.

3. A compound of the formula (KIb) according to claim 1 wherein R$^2$ represents hydrogen, methyl, ethyl, n- or i-propyl, or cyclopropyl.

4. A process for preparing a compound of the formula (Ib) according to claim 1 comprising reacting a compound of the formula (II)

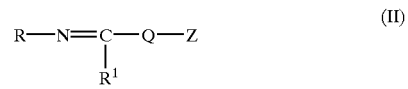

wherein

R represents CN,

R$^1$ is as defined for formula (Ib) of claim 1,

Q represents oxygen or sulphur, and

Z represents C$_1$–C$_4$-alkyl, with a compound of the formula (III)

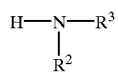
(III)

wherein

R² is as defined in claim 1, and

R³ represents

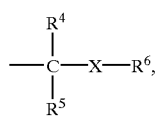

wherein R⁴, R⁵, and R⁶ are each as defined for formula (Ib) of claim 1, in the presence of a diluent.

5. A pesticide comprising one or more of the compounds of claim 1 and a member selected from the group consisting of liquid solvents, solid carriers, surfactants and mixtures thereof.

6. A process for preparing pesticides comprising mixing one or more of the compounds of claim 1 with a member selected from the group consisting of liquid solvents, solid carriers, surfactants and mixtures thereof.

7. A method of controlling pests selected from the group consisting of insects, arachnids, nematodes and ectoparasites comprising allowing an effective amount of one or more of the compounds of claim 1 to act on said pests and/or their habitat.

* * * * *